US011479768B2

(12) United States Patent
Plank et al.

(10) Patent No.: US 11,479,768 B2
(45) Date of Patent: Oct. 25, 2022

(54) ATP-BINDING CASSETTE FAMILY CODING POLYRIBONUCLEOTIDES AND FORMULATIONS THEREOF

(71) Applicant: Ethris GmbH, Planegg (DE)

(72) Inventors: Christian Plank, Wessling (DE); Carsten Rudolph, Krailing (DE); Manish Kumar Aneja, Munich (DE); Ludwig Weiss, Kissing (DE); Mehrije Ferizi, Munich (DE); Johannes Geiger, Munich (DE)

(73) Assignee: Ethris GmbH, Planegg (DE)

( * ) Notice: Subject to any disclaimer, the term of this patent is extended or adjusted under 35 U.S.C. 154(b) by 0 days.

(21) Appl. No.: 15/739,146

(22) PCT Filed: Jun. 30, 2016

(86) PCT No.: PCT/EP2016/065321
§ 371 (c)(1),
(2) Date: Dec. 21, 2017

(87) PCT Pub. No.: WO2017/001570
PCT Pub. Date: Jan. 5, 2017

(65) Prior Publication Data

US 2018/0371456 A1 Dec. 27, 2018

(30) Foreign Application Priority Data

Jun. 30, 2015 (EP) .................................... 15174677

(51) Int. Cl.

| | |
|---|---|
| ***C12N 15/113*** | (2010.01) |
| ***C12N 15/63*** | (2006.01) |
| ***A61K 48/00*** | (2006.01) |
| ***A61K 38/16*** | (2006.01) |
| ***C07K 14/47*** | (2006.01) |
| ***C12N 15/62*** | (2006.01) |
| *A61K 9/107* | (2006.01) |
| *A61K 9/127* | (2006.01) |
| *A61K 9/51* | (2006.01) |

(52) U.S. Cl.
CPC ............ *C12N 15/113* (2013.01); *A61K 38/16* (2013.01); *A61K 48/0066* (2013.01); *A61K 48/0083* (2013.01); *C07K 14/4705* (2013.01); *C12N 15/62* (2013.01); *A61K 9/1075* (2013.01); *A61K 9/1271* (2013.01); *A61K 9/51* (2013.01)

(58) Field of Classification Search
None
See application file for complete search history.

(56) References Cited

U.S. PATENT DOCUMENTS

| | | | | |
|---|---|---|---|---|
| 2011/0035819 A1* | 2/2011 | Cooper | A61K 48/005 | 800/14 |
| 2011/0143397 A1* | 6/2011 | Kariko | A61K 48/0041 | 435/70.3 |
| 2012/0195936 A1* | 8/2012 | Rudolph | A61K 48/0066 | 424/400 |
| 2016/0168227 A1* | 6/2016 | Kallen | A61K 39/0011 | 424/185.1 |

FOREIGN PATENT DOCUMENTS

| | | | | |
|---|---|---|---|---|
| CN | 102947450 A | | 2/2013 | |
| CN | 104349794 A | | 2/2015 | |
| EP | 3 112 469 A1 | | 1/2017 | |
| WO | WO-2004018633 A2 | * | 3/2004 | C07K 14/705 |
| WO | WO 2009/055760 A1 | | 4/2009 | |
| WO | WO2011/071931 A1 | | 6/2011 | |
| WO | WO 2013/182683 A1 | | 12/2013 | |
| WO | WO2013/182683 A1 | | 12/2013 | |
| WO | WO 2014/130909 A1 | | 8/2014 | |
| WO | WO 2014/207231 A1 | | 12/2014 | |
| WO | WO 2015/024667 A1 | | 2/2015 | |
| WO | WO 2017/001570 | | 1/2017 | |

OTHER PUBLICATIONS

Sharova et al., Database for mRNA Half-Life of 19 977 Genes Obtained by DNA Microarray Analysis of Pluripotent and Differentiating Mouse Embryonic Stem Cells. DNA Res, 2009, 16:45-58 (Year: 2009).*

Debus et al., Delivery of messenger RNA using poly(ethylene imine)-poly(ethylene glycol)-copolymer blends for polyplex formation: biophysical characterization and in vitro transfection properties. J Control Release. Dec. 20, 2010;148(3):334-43 (Year: 2010).*

Kariko et al., Increased Erythropoiesis in Mice Injected With Submicrogram Quantities of Pseudouridine-containing mRNA Encoding Erythropoietin. Mol Therapy. vol. 20, Issue 5, May 2012, pp. 948-953 (Year: 2012).*

Cheong et al., ABCA3 is critical for lamellar body biogenesis in vivo. J Biol Chem. Aug. 17, 2007;282(33):23811-7. (Year: 2007).*

Schwarzer et al., NADPH oxidase-dependent acid production in airway epithelial cells. J Biol Chem. Aug. 27, 2004;279(35):36454-61. Epub Jun. 21, 2004. (Year: 2004).*

NCBI Reference Sequence: NM_000101.4. *Homo sapiens* cytochrome b-245 alpha chain (CYBA), mRNA. p. 1-6, May 2, 2019. (Year: 2019).*

Vishwakarma et al., Human ATP Binding Cassette (ABC) Transporters: A Phylogenetic Investigation. International Journal of Science and Research. vol. 3 Issue 6, Jun. 2014, p. 564-571 (Year: 2014 ).*

(Continued)

*Primary Examiner* — Arthur S Leonard
(74) *Attorney, Agent, or Firm* — Morse, Barnes-Brown & Pendleton, P.C.; Erin E. Bryan, Esq.

(57) ABSTRACT

Polynucleotides encoding peptides, proteins, enzymes, and functional fragments thereof are disclosed. The polynucleotides of the disclosure can be effectively delivered to an organ, such as the lung, and expressed within cells of the organ. The polyribonucleotides of the disclosure can be used to treat a disease or condition associated with a gene of the ATP-binding cassette (ABC) family, such as ABCA3.

16 Claims, 13 Drawing Sheets

Specification includes a Sequence Listing.

(56) References Cited

OTHER PUBLICATIONS

Chen et al., Mutations in the ABCA3 Gene are Associated With CataractMicrocornea Syndrome. Invest Ophthalmol Vis Sci. 2014;55:8031-8043. (Year: 2014).*
Mignone, Flavio, et al. "Untranslated regions of mRNAs." *Genome biology* 3.3 (2002): 4.1-4.10.
Kormann, Michael SD, et al. "Expression of therapeutic proteins after delivery of chemically modified mRNA in mice." *Nature biotechnology* 29.2 (2011): 154-157.
Yoshida, Ichiro, Nobuhiro Ban, and Nobuya Inagaki. "Expression of ABCA3, a causative gene for fatal surfactant deficiency, is up-regulated by glucocorticoids in lung alveolar type II cells." *Biochemical and biophysical research communications* 323.2 (2004): 547-555.
Winter, J., et al. "Neonatal respiratory insufficiency caused by an (homozygous) ABCA3-stop mutation: a systematic evaluation of therapeutic options." *Klinische Pädiatrie* 226.02 (2014): 53-58.
Ferizi, Mehrije, et al. "Stability analysis of chemically modified mRNA using micropattern-based single-cell arrays." *Lab on a Chip* 15.17 (2015): 3561-3571.
International Preliminary Report on Patentability for International Application No. PCT/EP2016/065321, dated Jan. 2, 2018.
Presnyak, Vladimir, et al. "Codon optimality is a major determinant of mRNA stability." Cell 160.6 (2015): 1111-1124.
Dana, Alexandra, and Tamir Tuller. "The effect of tRNA levels on decoding times of mRNA codons." Nucleic acids research 42.14 (2014): 9171-9181.
Wilkens, Stephan. "Structure and mechanism of ABC transporters." F1000prime reports 7.14 (2015).
Gene, 2013, vol. 534, pp. 417-420, URL, http://dx.doi.org/10.1016/j.gene.2013.11.015.

* cited by examiner

SEQUENCE LISTING

<160> NUMBER OF SEQ ID NOS: 19

<210> SEQ ID NO 1
<211> LENGTH: 36
<212> TYPE: DNA
<213> ORGANISM: Artificial
<220> FEATURE:
<223> OTHER INFORMATION: CYBA 5'

<400> SEQUENCE: 1
cgcgcctagc agtgtcccag ccgggttcgt gtcgcc 36

<210> SEQ ID NO 2
<211> LENGTH: 64
<212> TYPE: DNA
<213> ORGANISM: Artificial
<220> FEATURE:
<223> OTHER INFORMATION: CYBA 3'

<400> SEQUENCE: 2
cctcgccccg gacctgccct cccgccaggt gcacccacct gcaataaatg cagcgaagcc 60
ggga 64

<210> SEQ ID NO 3

-continued

<211> LENGTH: 66
<212> TYPE: DNA
<213> ORGANISM: Artificial
<220> FEATURE:
<223> OTHER INFORMATION: alpha-globin 5' UTR (HBA1)

<400> SEQUENCE: 3
cataaaccct ggcgcgctcg cggcccggca ctcttctggt ccccacagac tcagagagaa 60
cccacc 66

<210> SEQ ID NO 4
<211> LENGTH: 66
<212> TYPE: DNA
<213> ORGANISM: Artificial
<220> FEATURE:
<223> OTHER INFORMATION: alpha-globin 5' UTR (HBA2)

<400> SEQUENCE: 4
cataaaccct ggcgcgctcg cgggccggca ctcttctggt ccccacagac tcagagagaa 60
cccacc 66

<210> SEQ ID NO 5
<211> LENGTH: 30
<212> TYPE: DNA
<213> ORGANISM: Artificial
<220> FEATURE:
<223> OTHER INFORMATION: alpha -globin 5' UTR ETH

<400> SEQUENCE: 5
tcttctggtc cccacagact cagagagaac 30

<210> SEQ ID NO 6
<211> LENGTH: 712
<212> TYPE: DNA
<213> ORGANISM: Artificial
<220> FEATURE:
<223> OTHER INFORMATION: ABCA3 5'

<400> SEQUENCE: 6
gcggccgctg cgtccgccag tagcgggttg caggcgcacc ctcccctcca gggcggccac 60
gcagctgtca gtgccgccgc cactgcgagg ctggagcgga gcccgggtgg ccgagggagg 120
ggaccccgcg agagggccgc gcgccggccg ccgccgcccc ggcgcccagg ctcggtgctg 180
gagagtcatg cctgtgagcc ctgggcacct cctgatgtcc tgcgaggtca cggtgttccc 240
aaacctcagg gttgccctgc cccactccag aggctctcag gccccacccc ggagccctct 300
gtgcggagcc gcctcctcct ggccagttcc ccagtagtcc tgaagggaga cctgctgtgt 360
ggagcctctt ctgggaccca gccatgagtg tggagctgag caactgaacc tgaaactctt 420
ccactgtgag tcaaggaggc ttttccgcac atgaaggacg ctgagcggga aggactcctc 480
tctgcctgca gttgtagcga gtggaccagc accaggggct ctctagactg cccctcctcc 540
atcgccttcc ctgcctctcc aggacagagc agccacgtct gcacacctcg ccctctttac 600
actcagtttt cagagcacgt ttctcctatt tcctgcgggt tgcagcgcct acttgaactt 660
actcagacca cctacttctc tagcagcact gggcgtccct ttcagcaaga cg 712

<210> SEQ ID NO 7
<211> LENGTH: 796
<212> TYPE: DNA
<213> ORGANISM: Artificial
<220> FEATURE:
<223> OTHER INFORMATION: ABCA3 3' (ABCA3 5')

<400> SEQUENCE: 7
ggggtggcgg ctgtctcgcc atcaggcagg gacaggacgg gcaagcaggg cccatcttac 60
atcctctctc tccaagttta tctcatcctt tatttttaat cacttttttc tatgatggat 120
atgaaaaatt caaggcagta tgcacagaat ggacgagtgc agcccagccc tcatgcccag 180
gatcagcatg cgcatctcca tgtctgcata ctctggagtt cactttccca gagctggggc 240
aggccgggca gtctgcgggc aagctccggg gtctctgggt ggagagctga cccaggaagg 300
gctgcagctg agctgggggt tgaatttctc caggcactcc ctggagagag gacccagtga 360
cttgtccaag tttacacacg acactaatct cccctgggga ggaagcggga agccagccag 420
gttgaactgt agcgaggccc ccaggccgcc aggaatggac catgcagatc actgtcagtg 480
gagggaagct gctgactgtg attaggtgct ggggtcttag cgtccagcgc agcccggggg 540
catcctggag gctctgctcc ttagggcatg gtagtcaccg cgaagccggg caccgtccca 600
cagcatctcc tagaagcagc cggcacagga gggaaggtgg ccaggctcga agcagtctct 660
gtttccagca ctgcaccctc aggaagtcgc ccgccccagg acacgcaggg accaccctaa 720
gggctgggtg gctgtctcaa ggacacattg aatacgttgt gaccatccag aaaataaatg 780
ctgaggggac acagtc 796

<210> SEQ ID NO 8
<211> LENGTH: 5112
<212> TYPE: RNA
<213> ORGANISM: Homo sapiens

<400> SEQUENCE: 8
auggcugugc ucaggcagcu ggcgcuccuc cucuggaaga acuacacccu gcagaagcgg 60
aagguccugg ugacgguccu ggaacucuuc cugccauugc uguuuucugg gauccucauc 120
uggcuccgcu ugaagauuca gucggaaaau gugcccaacg ccaccaucua cccgggccag 180
uccauccagg agcugccucu guucuucacc uucccuccgc caggagacac cugggagcuu 240
gccuacaucc cuucucacag ugacgcugcc aagaccguca cugagacagu gcgcagggca 300
cuugugauca acaugcgagu gcgcggcuuu ccccuccgaga aggacuuuga ggacuacauu 360
agguacgaca acugcucguc cagcgugcug gccgccgugg ucuucgagca ccccuucaac 420
cacagcaagg agccccugcc gcuggcggug aaauaucacc uacgguucag uuacacacgg 480
agaaauuaca uguggaccca aacaggcucc uuuuuccuga aagagacaga aggcuggcac 540
acuacuuccc uuuucccgcu uuucccaaac ccaggaccaa gggaaccuac auccccugau 600
ggcggagaac cuggguacau ccgggaaggc uuccuggccg ugcagcaugc uguggaccgg 660
gccaucaugg aguaccaugc cgaugccgcc acacgccagc uguuccagag acugacggug 720
accaucaaga gguucccgua cccgccguuc aucgcagacc ccuuccucgu ggccauccag 780
uaccagcugc cccugcugcu gcugcucagc uucaccuaca ccgcgcucac cauugcccgu 840
gcugucgugc aggagaagga aaggaggcug aaggaguaca ugcgcaugau ggggcucagc 900
agcuggcugc acuggagugc cugguucccuc uuguucuucc ucuuccuccu caucgccgcc 960
uccuucauga cccugcucuu cugugucaag gugaagccaa auguagccgu gcugucccgc 1020
agcgaccccu cccuggugcu cgccuuccug cugugcuucg ccaucucuac caucuccuuc 1080
agcuucaugg ucagcaccuu cuucagcaaa gccaacaugg cagcagccuu cggaggcuuc 1140
cucuacuucu ucaccuacau ccccuacuuc uucguggccc cucgguacaa cuggaugacu 1200

-continued

```
cugagccaga agcucugcuc cugccuccug ucuaaugucg ccauggcaau gggagcccag   1260
cucauuggga aauuugaggc gaaaggcaug ggcauccagu ggcgagaccu ccugaguccc   1320
gucaacgugg acgacgacuu cugcuucggg caggugcugg ggaugcugcu gcuggacucu   1380
gugcucuaug gccuggugac cugguacaug gaggccgucu ucccagggca guucggcgug   1440
ccucagcccu gguacuucuu caucaugccc uccuauuggu gugggaagcc aagggcgguu   1500
gcagggaagg aggaagaaga cagugacccc gagaaagcac ucagaaacga guacuuugaa   1560
gccgagccag aggaccuggu ggcggggauc aagaucaagc accuguccaa gguguucagg   1620
gugggaaaua aggacagggc ggccgucaga gaccugaacc ucaaccugua cgagggacag   1680
aucaccgucc ugcugggcca caacggugcc gggaagacca ccacccucuc caugcucaca   1740
ggucucuuuc cccccaccag uggacgggca uacaucagcg gguaugaaau uucccaggac   1800
augguucaga uccggaagag ccugggccug ugcccgcagc acgacauccu guuugacaac   1860
uugacagucg cagagcaccu uuauuucuac gcccagcuga agggccuguc acgucagaag   1920
ugcccugaag aagucaagca gaugcugcac aucaucggcc uggaggacaa guggaacuca   1980
cggagccgcu uccugagcgg gggcaugagg cgcaagcucu ccaucggcau cgcccucauc   2040
gcaggcucca aggugcugau acuggacgag cccaccucgg gcauggacgc caucuccagg   2100
agggccaucu gggaucuucu ucagcggcag aaaagugacc gcaccaucgu gcugaccacc   2160
cacuucaugg acgaggcuga ccugcuggga gaccgcaucg ccaucauggc caagggggag   2220
cugcagugcu gcggguccuc gcuguuccuc aagcagaaau acggugccgg cuaucacaug   2280
acgcugguga aggagccgca cugcaacccg gaagacaucu cccagcuggu ccaccaccac   2340
gugcccaacg ccacgcugga gagcagcgcu ggggccgagc ugucuuucau ccuucccaga   2400
gagagcacgc acagguuuga aggucucuuu gcuaaacugg agaagaagca gaaagagcug   2460
ggcauugcca gcuuuggggc auccaucacc accauggagg aagucuuccu ucgggucggg   2520
aagcuggugg acagcaguau ggacauccag gccauccagc ucccugcccu gcaguaccag   2580
cacgagaggc gcgccagcga cugggcugug gacagcaacc ucuguggggc cauggacccc   2640
uccgacggca uuggagcccu caucgaggag gagcgcaccg cugucaagcu caacacuggg   2700
cucgcccugc acugccagca auucugggcc auguuccuga agaaggccgc auacagcugg   2760
cgcgagugga aaaugguggc ggcacagguc cuggugccuc ugaccugcgu cacccuggcc   2820
cuccuggcca ucaacuacuc cucggagcuc uucgacgacc ccaugcugag gcugaccuug   2880
ggcgaguacg gcagaaccgu cgugcccuuc ucaguucccg ggaccuccca gcugggucag   2940
cagcugucag agcaucugaa agacgcacug caggcugagg gacaggagcc ccgcgaggug   3000
cucggugacc uggaggaguu cuugaucuuc agggcuucug uggagggggg cggcuuuaau   3060
gagcggugcc uuguggcagc guccuucaga gauguggggag agcgcacggu cgucaacgcc  3120
uuguucaaca accaggcgua ccacucucca gccacugccc uggccgucgu ggacaaccuu   3180
cuguucaagc ugcugugcgg gccucacgcc uccauugugg ucuccaacuu cccccagccc   3240
cggagcgccc ugcaggcugc caaggaccag uuuaacgagg gccggaaggg auucgacauu   3300
gcccucaacc ugcucuucgc cauggcauuc uuggccagca cguucuccau ccuggcgguc   3360
agcgagaggg ccgugcaggc caagcaugug caguuuguga guggagucca cguggccagu   3420
uucuggcucu cugcucugcu gugggaccuc aucuccuucc ucaucccccag ucugcugcug  3480
cugguggugu uuaaggccuu cgacgugcgu gccuucacgc gggacggcca cauggcugac   3540
acccugcugc ugcuccugcu cuacggcugg gccaucaucc cccucaugua ccugaugaac   3600
```

uucuucuucu ugggggcggc cacugccuac acgaggcuga ccaucuucaa cauccuguca 3660
ggcaucgcca ccuuccugau ggucaccauc augcgcaucc cagcuguaaa acuggaagaa 3720
cuuuccaaaa cccuggauca cguguuccug gugcugccca accacugucu ggggauggca 3780
gucagcaguu ucuacgagaa cuacgagacg cggagguacu gcaccuccuc cgaggucgcc 3840
gcccacuacu gcaagaaaua uaacauccag uaccaggaga acuucuaugc cuggagcgcc 3900
ccgggggucg gccgguuugu ggccuccaug gccgccucag ggugcgccua ccucauccug 3960
cucuuccuca ucgagaccaa ccugcuucag agacucaggg gcauccucug cgcccuccgg 4020
aggaggcgga cacugacaga auuauacacc cggaugccug ugcuuccuga ggaccaagau 4080
guagcggacg agaggacccg cauccuggcc cccagcccgg acucccugcu ccacacaccu 4140
cugauuauca aggagcucuc caagguguac gagcagcggg ugccccuccu ggccguggac 4200
aggcucuccc ucgcggugca gaaaggggag ugcuucggcc ugcugggcuu caauggagcc 4260
gggaagacca cgacuuucaa aaugcugacc ggggaggaga gccucacuuc uggggaugcc 4320
uuugucgggg gucacagaau cagcucugau gucggaaagg ugcggcagcg gaucggcuac 4380
ugcccgcagu uugaugccuu gcuggaccac augacaggcc gggagaugcu ggucauguac 4440
gcucggcucc ggggcauccc ugagcgccac aucggggccu gcguggagaa cacucugcgg 4500
ggccugcugc uggagccaca ugccaacaag cuggucagga cguacagugg ugguaacaag 4560
cggaagcuga gcaccggcau cgcccugauc ggagagccug cugucaucuu ccuggacgag 4620
ccguccacug gcauggaccc cguggcccgg cgccugcuuu gggacaccgu ggcacgagcc 4680
cgagagucug gcaaggccau caucaucacc ucccacagca uggaggagug ugaggcccug 4740
ugcacccggc uggccaucau ggugcagggg caguucaagu gccugggcag cccccagcac 4800
cucaagagca aguucggcag cggcuacucc cugcgggcca aggugcagag ugaagggcaa 4860
caggaggcgc uggaggaguu caaggccuuc guggaccuga ccuuuccagg cagcguccug 4920
gaagaugagc accaaggcau gguccauuac caccugccgg gccgugaccu cagcugggcg 4980
aagguuuucg guauucugga gaaagccaag gaaaaguacg gcguggacga cuacuccgug 5040
agccagaucu cgcuggaaca ggucuuccug agcuucgccc accugcagcc gcccaccgca 5100
gaggaggggc ga 5112

<210> SEQ ID NO 9
<211> LENGTH: 5112
<212> TYPE: DNA
<213> ORGANISM: Homo sapiens

<400> SEQUENCE: 9
atggctgtgc tcaggcagct ggcgctcctc ctctggaaga actacaccct gcagaagcgg 60
aaggtcctgg tgacggtcct ggaactcttc ctgccattgc tgttttctgg gatcctcatc 120
tggctccgct tgaagattca gtcggaaaat gtgcccaacg ccaccatcta cccgggccag 180
tccatccagg agctgcctct gttcttcacc ttccctccgc caggagacac ctgggagctt 240
gcctacatcc cttctcacag tgacgctgcc aagaccgtca ctgagacagt gcgcagggca 300
cttgtgatca acatgcgagt gcgcggcttt ccctccgaga aggactttga ggactacatt 360
aggtacgaca actgctcgtc cagcgtgctg gccgccgtgg tcttcgagca ccccttcaac 420
cacagcaagg agcccctgcc gctggcggtg aaatatcacc tacggttcag ttacacacgg 480
agaaattaca tgtggaccca aacaggctcc tttttcctga aagagacaga aggctggcac 540

-continued

```
actacttccc ttttcccgct tttcccaaac ccaggaccaa gggaacctac atcccctgat    600
ggcggagaac ctgggtacat ccgggaaggc ttcctggccg tgcagcatgc tgtggaccgg    660
gccatcatgg agtaccatgc cgatgccgcc acacgccagc tgttccagag actgacggtg    720
accatcaaga ggttcccgta cccgccgttc atcgcagacc ccttcctcgt ggccatccag    780
taccagctgc ccctgctgct gctgctcagc ttcacctaca ccgcgctcac cattgcccgt    840
gctgtcgtgc aggagaagga aaggaggctg aaggagtaca tgcgcatgat ggggctcagc    900
agctggctgc actggagtgc ctggttcctc ttgttcttcc tcttcctcct catcgccgcc    960
tccttcatga ccctgctctt ctgtgtcaag gtgaagccaa atgtagccgt gctgtcccgc   1020
agcgacccct ccctggtgct cgccttcctg ctgtgcttcg ccatctctac catctccttc   1080
agcttcatgg tcagcacctt cttcagcaaa gccaacatgg cagcagcctt cggaggcttc   1140
ctctacttct tcacctacat cccctacttc ttcgtggccc ctcggtacaa ctggatgact   1200
ctgagccaga agctctgctc ctgcctcctg tctaatgtcg ccatggcaat gggagcccag   1260
ctcattggga aatttgaggc gaaaggcatg ggcatccagt ggcgagacct cctgagtccc   1320
gtcaacgtgg acgacgactt ctgcttcggg caggtgctgg ggatgctgct gctggactct   1380
gtgctctatg gcctggtgac ctggtacatg gaggccgtct tcccagggca gttcggcgtg   1440
cctcagccct ggtacttctt catcatgccc tcctattggt gtgggaagcc aagggcggtt   1500
gcagggaagg aggaagaaga cagtgacccc gagaaagcac tcagaaacga gtactttgaa   1560
gccgagccag aggacctggt ggcggggatc aagatcaagc acctgtccaa ggtgttcagg   1620
gtgggaaata aggacagggc ggccgtcaga gacctgaacc tcaacctgta cgagggacag   1680
atcaccgtcc tgctgggcca caacggtgcc gggaagacca ccaccctctc catgctcaca   1740
ggtctctttc cccccaccag tggacgggca tacatcagcg ggtatgaaat ttcccaggac   1800
atggttcaga tccggaagag cctgggcctg tgcccgcagc acgacatcct gtttgacaac   1860
ttgacagtcg cagagcacct ttatttctac gcccagctga agggcctgtc acgtcagaag   1920
tgccctgaag aagtcaagca gatgctgcac atcatcggcc tggaggacaa gtggaactca   1980
cggagccgct tcctgagcgg gggcatgagg cgcaagctct ccatcggcat cgccctcatc   2040
gcaggctcca aggtgctgat actggacgag cccacctcgg gcatggacgc catctccagg   2100
agggccatct gggatcttct tcagcggcag aaaagtgacc gcaccatcgt gctgaccacc   2160
cacttcatgg acgaggctga cctgctggga gaccgcatcg ccatcatggc caagggggag   2220
ctgcagtgct gcgggtcctc gctgttcctc aagcagaaat acggtgccgg ctatcacatg   2280
acgctggtga aggagccgca ctgcaacccg gaagacatct cccagctggt ccaccaccac   2340
gtgcccaacg ccacgctgga gagcagcgct ggggccgagc tgtctttcat ccttcccaga   2400
gagagcacgc acaggtttga aggtctcttt gctaaactgg agaagaagca gaaagagctg   2460
ggcattgcca gctttggggc atccatcacc accatggagg aagtcttcct tcgggtcggg   2520
aagctggtgg acagcagtat ggacatccag gccatccagc tccctgccct gcagtaccag   2580
cacgagaggc gcgccagcga ctgggctgtg gacagcaacc tctgtggggc catggacccc   2640
tccgacggca ttggagccct catcgaggag gagcgcaccg ctgtcaagct caacactggg   2700
ctcgccctgc actgccagca attctgggcc atgttcctga agaaggccgc atacagctgg   2760
cgcgagtgga aaatggtggc ggcacaggtc ctggtgcctc tgacctgcgt caccctggcc   2820
ctcctggcca tcaactactc ctcggagctc ttcgacgacc ccatgctgag gctgaccttg   2880
ggcgagtacg gcagaaccgt cgtgcccttc tcagttcccg ggacctccca gctgggtcag   2940
```

-continued

```
cagctgtcag agcatctgaa agacgcactg caggctgagg gacaggagcc ccgcgaggtg   3000
ctcggtgacc tggaggagtt cttgatcttc agggcttctg tggagggggg cggctttaat   3060
gagcggtgcc ttgtggcagc gtccttcaga gatgtgggag agcgcacggt cgtcaacgcc   3120
ttgttcaaca accaggcgta ccactctcca gccactgccc tggccgtcgt ggacaacctt   3180
ctgttcaagc tgctgtgcgg gcctcacgcc tccattgtgg tctccaactt cccccagccc   3240
cggagcgccc tgcaggctgc caaggaccag tttaacgagg gccggaaggg attcgacatt   3300
gccctcaacc tgctcttcgc catggcattc ttggccagca cgttctccat cctggcggtc   3360
agcgagaggg ccgtgcaggc caagcatgtg cagtttgtga gtggagtcca cgtggccagt   3420
ttctggctct ctgctctgct gtgggacctc atctccttcc tcatccccag tctgctgctg   3480
ctggtggtgt ttaaggcctt cgacgtgcgt gccttcacgc gggacggcca catggctgac   3540
accctgctgc tgctcctgct ctacggctgg gccatcatcc ccctcatgta cctgatgaac   3600
ttcttcttct tgggggcggc cactgcctac acgaggctga ccatcttcaa catcctgtca   3660
ggcatcgcca ccttcctgat ggtcaccatc atgcgcatcc cagctgtaaa actggaagaa   3720
ctttccaaaa ccctggatca cgtgttcctg gtgctgccca accactgtct ggggatggca   3780
gtcagcagtt tctacgagaa ctacgagacg cggaggtact gcacctcctc cgaggtcgcc   3840
gcccactact gcaagaaata taacatccag taccaggaga acttctatgc ctggagcgcc   3900
ccgggggtcg gccggtttgt ggcctccatg gccgcctcag ggtgcgccta cctcatcctg   3960
ctcttcctca tcgagaccaa cctgcttcag agactcaggg gcatcctctg cgccctccgg   4020
aggaggcgga cactgacaga attatacacc cggatgcctg tgcttcctga ggaccaagat   4080
gtagcggacg agaggacccg catcctggcc cccagcccgg actccctgct ccacacacct   4140
ctgattatca aggagctctc caaggtgtac gagcagcggg tgcccctcct ggccgtggac   4200
aggctctccc tcgcggtgca gaaaggggag tgcttcggcc tgctgggctt caatggagcc   4260
gggaagacca cgactttcaa aatgctgacc ggggaggaga gcctcacttc tggggatgcc   4320
tttgtcgggg gtcacagaat cagctctgat gtcggaaagg tgcggcagcg gatcggctac   4380
tgcccgcagt ttgatgcctt gctggaccac atgacaggcc gggagatgct ggtcatgtac   4440
gctcggctcc ggggcatccc tgagcgccac atcggggcct gcgtggagaa cactctgcgg   4500
ggcctgctgc tggagccaca tgccaacaag ctggtcagga cgtacagtgg tggtaacaag   4560
cggaagctga gcaccggcat cgccctgatc ggagagcctg ctgtcatctt cctggacgag   4620
ccgtccactg gcatggaccc cgtggcccgg cgcctgcttt gggacaccgt ggcacgagcc   4680
cgagagtctg gcaaggccat catcatcacc tcccacagca tggaggagtg tgaggccctg   4740
tgcacccggc tggccatcat ggtgcagggg cagttcaagt gcctgggcag cccccagcac   4800
ctcaagagca agttcggcag cggctactcc ctgcgggcca aggtgcagag tgaagggcaa   4860
caggaggcgc tggaggagtt caaggccttc gtggacctga cctttccagg cagcgtcctg   4920
gaagatgagc accaaggcat ggtccattac cacctgccgg gccgtgacct cagctgggcg   4980
aaggttttcg gtattctgga gaaagccaag gaaaagtacg gcgtggacga ctactccgtg   5040
agccagatct cgctggaaca ggtcttcctg agcttcgccc acctgcagcc gcccaccgca   5100
gaggaggggc ga                                                       5112
```

<210> SEQ ID NO 10
<211> LENGTH: 5437
<212> TYPE: DNA

-continued

<213> ORGANISM: Artificial
<220> FEATURE:
<223> OTHER INFORMATION: native ABCA3 DNA sequence with a 5' CYBA UTR
and a 3' CYBA UTR

<400> SEQUENCE: 10
cgcgcctagc agtgtcccag ccgggttcgt gtcgccgcca ccatggctgt gctcaggcag 60
ctggcgctcc tcctctggaa gaactacacc ctgcagaagc ggaaggtcct ggtgacggtc 120
ctggaactct tcctgccatt gctgttttct gggatcctca tctggctccg cttgaagatt 180
cagtcggaaa atgtgcccaa cgccaccatc tacccgggcc agtccatcca ggagctgcct 240
ctgttcttca ccttccctcc gccaggagac acctgggagc ttgcctacat cccttctcac 300
agtgacgctg ccaagaccgt cactgagaca gtgcgcaggg cacttgtgat caacatgcga 360
gtgcgcggct ttccctccga gaaggacttt gaggactaca ttaggtacga caactgctcg 420
tccagcgtgc tggccgccgt ggtcttcgag cacccettca accacagcaa ggagcccctg 480
ccgctggcgg tgaaatatca cctacggttc agttacacac ggagaaatta catgtggacc 540
caaacaggct cctttttcct gaaagagaca gaaggctggc acactacttc cctttcccg 600 cttttcccaa acccaggacc aagggaacct acatcccctg atggcggaga acctgggtac 660
atccgggaag gcttcctggc cgtgcagcat gctgtggacc gggccatcat ggagtaccat 720
gccgatgccg ccacacgcca gctgttccag agactgacgg tgaccatcaa gaggttcccg 780
tacccgccgt tcatcgcaga ccccttcctc gtggccatcc agtaccagct gcccctgctg 840
ctgctgctca gcttcaccta caccgcgctc accattgccc gtgctgtcgt gcaggagaag 900
gaaaggaggc tgaaggagta catgcgcatg atggggctca gcagctggct gcactggagt 960
gcctggttcc tcttgttctt cctcttcctc ctcatcgccg cctccttcat gaccctgctc 1020
ttctgtgtca aggtgaagcc aaatgtagcc gtgctgtccc gcagcgaccc ctccctggtg 1080
ctcgccttcc tgctgtgctt cgccatctct accatctcct tcagcttcat ggtcagcacc 1140
ttcttcagca aagccaacat ggcagcagcc ttcggaggct tcctctactt cttcacctac 1200
atcccctact tcttcgtggc ccctcggtac aactggatga ctctgagcca gaagctctgc 1260
tcctgcctcc tgtctaatgt cgccatggca atgggagccc agctcattgg gaaatttgag 1320
gcgaaaggca tgggcatcca gtggcgagac ctcctgagtc ccgtcaacgt ggacgacgac 1380
ttctgcttcg ggcaggtgct ggggatgctg ctgctggact ctgtgctcta tggcctggtg 1440
acctggtaca tggaggccgt cttcccaggg cagttcggcg tgcctcagcc ctggtacttc 1500
ttcatcatgc cctcctattg gtgtgggaag ccaagggcgg ttgcagggaa ggaggaagaa 1560
gacagtgacc ccgagaaagc actcagaaac gagtactttg aagccgagcc agaggacctg 1620
gtggcgggga tcaagatcaa gcacctgtcc aaggtgttca gggtgggaaa taaggacagg 1680
gcggccgtca gagacctgaa cctcaacctg tacgagggac agatcaccgt cctgctgggc 1740
cacaacggtg ccgggaagac caccaccctc tccatgctca caggtctctt tcccccccacc 1800 agtggacggg catacatcag cgggtatgaa atttcccagg acatggttca gatccggaag 1860
agcctgggcc tgtgcccgca gcacgacatc ctgtttgaca acttgacagt cgcagagcac 1920
ctttatttct acgcccagct gaagggcctg tcacgtcaga agtgccctga agaagtcaag 1980
cagatgctgc acatcatcgg cctggaggac aagtggaact cacggagccg cttcctgagc 2040
gggggcatga ggcgcaagct ctccatcggc atcgccctca tcgcaggctc caaggtgctg 2100
atactggacg agcccacctc gggcatggac gccatctcca ggagggccat ctgggatctt 2160

-continued

```
cttcagcggc agaaaagtga ccgcaccatc gtgctgacca cccacttcat ggacgaggct   2220
gacctgctgg gagaccgcat cgccatcatg gccaaggggg agctgcagtg ctgcgggtcc   2280
tcgctgttcc tcaagcagaa atacggtgcc ggctatcaca tgacgctggt gaaggagccg   2340
cactgcaacc cggaagacat ctcccagctg gtccaccacc acgtgcccaa cgccacgctg   2400
gagagcagcg ctggggccga gctgtctttc atccttccca gagagagcac gcacaggttt   2460
gaaggtctct ttgctaaact ggagaagaag cagaaagagc tgggcattgc cagctttggg   2520
gcatccatca ccaccatgga ggaagtcttc cttcgggtcg ggaagctggt ggacagcagt   2580
atggacatcc aggccatcca gctccctgcc ctgcagtacc agcacgagag gcgcgccagc   2640
gactgggctg tggacagcaa cctctgtggg gccatggacc cctccgacgg cattggagcc   2700
ctcatcgagg aggagcgcac cgctgtcaag ctcaacactg ggctcgccct gcactgccag   2760
caattctggg ccatgttcct gaagaaggcc gcatacagct ggcgcgagtg gaaaatggtg   2820
gcggcacagg tcctggtgcc tctgacctgc gtcaccctgg ccctcctggc catcaactac   2880
tcctcggagc tcttcgacga ccccatgctg aggctgacct tgggcgagta cggcagaacc   2940
gtcgtgccct tctcagttcc cgggacctcc cagctgggtc agcagctgtc agagcatctg   3000
aaagacgcac tgcaggctga gggacaggag ccccgcgagg tgctcggtga cctggaggag   3060
ttcttgatct tcagggcttc tgtggagggg ggcggcttta atgagcggtg ccttgtggca   3120
gcgtccttca gagatgtggg agagcgcacg gtcgtcaacg ccttgttcaa caaccaggcg   3180
taccactctc cagccactgc cctggccgtc gtggacaacc ttctgttcaa gctgctgtgc   3240
gggcctcacg cctccattgt ggtctccaac ttcccccagc cccggagcgc cctgcaggct   3300
gccaaggacc agtttaacga gggccggaag ggattcgaca ttgccctcaa cctgctcttc   3360
gccatggcat tcttggccag cacgttctcc atcctggcgg tcagcgagag ggccgtgcag   3420
gccaagcatg tgcagtttgt gagtggagtc cacgtggcca gtttctggct ctctgctctg   3480
ctgtgggacc tcatctcctt cctcatcccc agtctgctgc tgctggtggt gtttaaggcc   3540
ttcgacgtgc gtgccttcac gcgggacggc cacatggctg acaccctgct gctgctcctg   3600
ctctacggct gggccatcat cccccctcatg tacctgatga acttcttctt cttgggggcg   3660
gccactgcct acacgaggct gaccatcttc aacatcctgt caggcatcgc caccttcctg   3720
atggtcacca tcatgcgcat cccagctgta aaactggaag aactttccaa aaccctggat   3780
cacgtgttcc tggtgctgcc caaccactgt ctggggatgg cagtcagcag tttctacgag   3840
aactacgaga cgcggaggta ctgcacctcc tccgaggtcg ccgcccacta ctgcaagaaa   3900
tataacatcc agtaccagga gaacttctat gcctggagcg ccccgggggt cggccggttt   3960
gtggcctcca tggccgcctc agggtgcgcc tacctcatcc tgctcttcct catcgagacc   4020
aacctgcttc agagactcag gggcatcctc tgcgccctcc ggaggaggcg gacactgaca   4080
gaattataca cccggatgcc tgtgcttcct gaggaccaag atgtagcgga cgagaggacc   4140
cgcatcctgg cccccagccc ggactccctg ctccacacac ctctgattat caaggagctc   4200
tccaaggtgt acgagcagcg ggtgcccctc ctggccgtgg acaggctctc cctcgcggtg   4260
cagaaagggg agtgcttcgg cctgctgggc ttcaatggag ccgggaagac cacgactttc   4320
aaaatgctga ccggggagga gagcctcact tctggggatg cctttgtcgg ggggtcacaga   4380
atcagctctg atgtcggaaa ggtgcggcag cggatcggct actgcccgca gtttgatgcc   4440
ttgctggacc acatgacagg ccgggagatg ctggtcatgt acgctcggct ccggggcatc   4500
cctgagcgcc acatcggggc ctgcgtggag aacactctgc ggggcctgct gctggagcca   4560
```

```
catgccaaca agctggtcag gacgtacagt ggtggtaaca agcggaagct gagcaccggc   4620

atcgccctga tcggagagcc tgctgtcatc ttcctggacg agccgtccac tggcatggac   4680

cccgtggccc ggcgcctgct ttgggacacc gtggcacgag cccgagagtc tggcaaggcc   4740

atcatcatca cctcccacag catggaggag tgtgaggccc tgtgcacccg gctggccatc   4800

atggtgcagg ggcagttcaa gtgcctgggc agcccccagc acctcaagag caagttcggc   4860

agcggctact ccctgcgggc caaggtgcag agtgaagggc aacaggaggc gctggaggag   4920

ttcaaggcct tcgtggacct gacctttcca ggcagcgtcc tggaagatga gcaccaaggc   4980

atggtccatt accacctgcc gggccgtgac ctcagctggg cgaaggtttt cggtattctg   5040

gagaaagcca aggaaaagta cggcgtggac gactactccg tgagccagat ctcgctggaa   5100

caggtcttcc tgagcttcgc ccacctgcag ccgcccaccg cagaggaggg gcgaacgcgt   5160

acgcgaccgc tcgagcagaa actcatctca gaagaggatc tggcagcaaa tgatatcctg   5220

gattacaagg atgacgacga taaggtttga cctcgccccg gacctgccct cccgccaggt   5280

gcacccacct gcaataaatg cagcgaagcc gggaaaaaaa aaaaaaaaaa aaaaaaaaaa   5340

aaaaaaaaaa aaaaaaaaaa aaaaaaaaaa aaaaaaaaaa aaaaaaaaaa aaaaaaaaaa   5400

aaaaaaaaaa aaaaaaaaaa aaaaaaaaaa aaaaatt                             5437
```

```
<210> SEQ ID NO 11
<211> LENGTH: 5437
<212> TYPE: RNA
<213> ORGANISM: Artificial
<220> FEATURE:
<223> OTHER INFORMATION: native ABCA3 mRNA sequence with a 5' CYBA UTR
      and a 3' CYBA UTR

<400> SEQUENCE: 11

cgcgccuagc aguguccag ccggguucgu gucgccgcca ccauggcugu gcucaggcag      60

cuggcgcucc uccucuggaa gaacuacacc cugcagaagc ggaagguccu ggugacgguc    120

cuggaacucu uccugccauu gcuguuuucu gggauccuca ucuggcuccg cuugaagauu    180

cagucggaaa augugcccaa cgccaccauc uacccgggcc aguccaucca ggagcugccu    240

cuguucuuca ccuucccucc gccaggagac accugggagc uugccuacau cccuucucac    300

agugacgcug ccaagaccgu cacugagaca gugcgcaggg cacuugugau caacaugcga    360

gugcgcggcu uucccuccga gaaggacuuu gaggacuaca uuagguacga caacugcucg    420

uccagcgugc uggccgccgu ggucuucgag caccccuuca accacagcaa ggagccccug    480

ccgcuggcgg ugaaauauca ccuacgguuc aguuacacac ggagaaauua cauguggacc    540

caaacaggcu ccuuuuuccu gaaagagaca gaaggcuggc acacuacuuc ccuuuucccg    600

cuuuucccaa acccaggacc aagggaaccu acaucccug auggcggaga accuggguac    660

auccgggaag gcuuccuggc cgugcagcau gcuguggacc gggccaucau ggaguaccau    720

gccgaugccg ccacacgcca gcuguuccag agacugacgg ugaccaucaa gagguucccg    780

uacccgccgu ucaucgcaga ccccuuccuc guggccaucc aguaccagcu gccccugcug    840

cugcugcuca gcuucaccua caccgcgcuc accauugccc gugcugucgu gcaggagaag    900

gaaaggaggc ugaaggagua caugcgcaug augggcuca gcagcuggcu gcacuggagu    960

gccugguucc ucuuguucuu ccucuuccuc cucaucgccg ccuccuucau gacccugcuc   1020

uucuguguca aggugaagcc aaauguagcc gugcuguccc gcagcgaccc cucccuggug   1080

cucgccuucc ugcugugcuu cgccaucucu accaucuccu ucagcuucau ggucagcacc   1140
```

-continued

```
uucuucagca aagccaacau ggcagcagcc uucggaggcu ucccucuacuu cuucaccuac   1200
auccccuacu ucuucguggc cccucgguac aacuggauga cucugagcca gaagcucugc   1260
uccugccucc ugucuaaugu cgccauggca augggagccc agcucauugg gaaauuugag   1320
gcgaaaggca ugggcaucca guggcgagac cuccugaguc ccgucaacgu ggacgacgac   1380
uucugcuucg ggcaggugcu ggggaugcug cugcuggacu cugugcucua uggccuggug   1440
accugguaca uggaggccgu cuucccaggg caguucggcg ugccucagcc cugguacuuc   1500
uucaucaugc ccuccuauug gugugggaag ccaagggcgg uugcagggaa ggaggaagaa   1560
gacagugacc ccgagaaagc acucagaaac gaguacuuug aagccgagcc agaggaccug   1620
guggcgggga ucaagaucaa gcaccugucc aagguguuca gggugggaaa uaaggacagg   1680
gcggccguca gagaccugaa ccucaaccug uacgagggac agaucaccgu ccugcugggc   1740
cacaacggug ccgggaagac caccacccuc uccaugcuca caggucucuu uccccccacc   1800
aguggacggg cauacaucag cgguaugaa auuucccagg acaugguuca gauccggaag   1860
agccugggcc ugugcccgca gcacgacauc cuguuugaca acuugacagu cgcagagcac   1920
cuuuauuucu acgcccagcu gaagggccug ucacgucaga agugcccuga agaagucaag   1980
cagaugcugc acaucaucgg ccuggaggac aaguggaacu cacggagccg cuuccugagc   2040
gggggcauga ggcgcaagcu cuccaucggc aucgcccuca ucgcaggcuc caaggugcug   2100
auacuggacg agcccaccuc gggcauggac gccaucucca ggagggccau cugggaucuu   2160
cuucagcggc agaaaaguga ccgcaccauc gugcugacca cccacuucau ggacgaggcu   2220
gaccugcugg gagaccgcau cgccaucaug gccaaggggg agcugcagug cugcgggucc   2280
ucgcuguucc ucaagcagaa auacggugcc ggcuaucaca ugacgcuggu gaaggagccg   2340
cacugcaacc cggaagacau cucccagcug guccaccacc acgugcccaa cgccacgcug   2400
gagagcagcg cuggggccga gcugucuuuc auccuuccca gagagagcac gcacagguuu   2460
gaaggucucu uugcuaaacu ggagaagaag cagaaagagc ugggcauugc cagcuuuggg   2520
gcauccauca ccaccaugga ggaagucuuc cuucgggucg ggaagcuggu ggacagcagu   2580
auggacaucc aggccaucca gcucccugcc cugcaguacc agcacgagag gcgcgccagc   2640
gacugggcug uggacagcaa ccucuguggg gccauggacc ccuccgacgg cauuggagcc   2700
cucaucgagg aggagcgcac cgcugucaag cucaacacug ggcucgcccu gcacugccag   2760
caauucuggg ccauguuccu gaagaaggcc gcauacagcu ggcgcgagug gaaaauggug   2820
gcggcacagg uccuggugcc ucugaccugc gucacccugg cccuccuggc caucaacuac   2880
uccucggagc ucuucgacga ccccaugcug aggcugaccu ugggcgagua cggcagaacc   2940
gucgugcccu ucucaguucc cgggaccucc cagcuggguc agcagcuguc agagcaucug   3000
aaagacgcac ugcaggcuga gggacaggag ccccgcgagg ugcucgguga ccuggaggag   3060
uucuugaucu ucagggcuuc uguggagggg ggcggcuuua augagcggug ccuuguggca   3120
gcguccuuca gagauguggg agagcgcacg gucgucaacg ccuuguucaa caaccaggcg   3180
uaccacucuc cagccacugc ccuggccguc guggacaacc uucuguucaa gcugcugugc   3240
gggccucacg ccuccauugu ggucuccaac uucccccagc cccggagcgc ccugcaggcu   3300
gccaaggacc aguuuaacga gggccggaag ggauucgaca uugcccucaa ccugcucuuc   3360
gccauggcau ucuuggccag cacguucucc auccuggcgg ucagcgagag ggccgugcag   3420
gccaagcaug ugcaguuugu gaguggaguc cacguggcca guuucuggcu cucugcucug   3480
```

cugugggacc ucaucuccuu ccucaucccc agucugcugc ugcugguggu guuuaaggcc 3540
uucgacgugc gugccuucac gcgggacggc cacauggcug acacccugcu gcugcuccug 3600
cucuacggcu gggccaucau cccccucaug uaccugauga acuucuucuu cuuggggggcg 3660 gccacugccu acacgaggcu gaccaucuuc aacauccugu caggcaucgc caccuuccug 3720
auggucacca ucaugcgcau cccagcugua aaacuggaag aacuuuccaa aacccuggau 3780
cacguguucc uggugcugcc caaccacugu cuggggaugg cagucagcag uuucuacgag 3840
aacuacgaga cgcggaggua cugcaccucc uccgaggucg ccgcccacua cugcaagaaa 3900
uauaacaucc aguaccagga gaacuucuau gccuggagcg ccccgggggu cggccgguuu 3960
guggccucca uggccgccuc agggugcgcc uaccucaucc ugcucuuccu caucgagacc 4020
aaccugcuuc agagacucag gggcauccuc ugcgcccucc ggaggaggcg gacacugaca 4080
gaauuauaca cccggaugcc ugugcuuccu gaggaccaag auguagcgga cgagaggacc 4140
cgcauccugg cccccagccc ggacucccug cuccacacac cucugauuau caaggagcuc 4200
uccaaggugu acgagcagcg ggugccccuc cuggccgugg acaggcucuc ccucgcggug 4260
cagaaagggg agugcuucgg ccugcugggc uucaauggag ccgggaagac cacgacuuuc 4320
aaaaugcuga ccggggagga gagccucacu ucuggggaug ccuuugucgg gggucacaga 4380
aucagcucug augucggaaa ggugcggcag cggaucggcu acugcccgca guuugaugcc 4440
uugcuggacc acaugacagg ccgggagaug cuggucaugu acgcucggcu ccggggcauc 4500
ccugagcgcc acaucggggc cugcguggag aacacucugc ggggccugcu gcuggagcca 4560
caugccaaca agcuggucag gacguacagu ggugguaaca agcggaagcu gagcaccggc 4620 aucgccccuga ucggagagcc ugcugucauc uuccuggacg agccguccac uggcauggac 4680
cccguggccc ggcgccugcu uugggacacc guggcacgag cccgagaguc uggcaaggcc 4740
aucaucauca ccucccacag cauggaggag ugugaggccc ugugcacccg gcuggccauc 4800
auggugcagg ggcaguucaa gugccugggc agcccccagc accucaagag caaguucggc 4860
agcggcuacu cccugcgggc caaggugcag agugaagggc aacaggaggc gcuggaggag 4920
uucaaggccu ucguggaccu gaccuuucca ggcagcgucc uggaagauga gcaccaaggc 4980
augguccauu accaccugcc gggccgugac cucagcuggg cgaagguuuu cgguauucug 5040
gagaaagcca aggaaaagua cggcguggac gacuacuccg ugagccagau cucgcuggaa 5100
caggucuucc ugagcuucgc ccaccugcag ccgcccaccg cagaggaggg gcgaacgcgu 5160
acgcgaccgc ucgagcagaa acucaucuca gaagaggauc uggcagcaaa ugauauccug 5220
gauuacaagg augacgacga uaagguuuga ccucgccccg gaccugcccu cccgccaggu 5280
gcacccaccu gcaauaaaug cagcgaagcc gggaaaaaaa aaaaaaaaaa aaaaaaaaaa 5340
aaaaaaaaaa aaaaaaaaaa aaaaaaaaaa aaaaaaaaaa aaaaaaaaaa aaaaaaaaaa 5400
aaaaaaaaaa aaaaaaaaaa aaaaaaaaaa aaaaaauu 5437

<210> SEQ ID NO 12
<211> LENGTH: 5441
<212> TYPE: DNA
<213> ORGANISM: Artificial
<220> FEATURE:
<223> OTHER INFORMATION: codon optimized ABCA3 DNA sequence with a 5' CYBA UTR and a 3' CYBA UTR

<400> SEQUENCE: 12
agaccgcgcc tagcagtgtc ccagccgggt tcgtgtcgcc gccaccatgg ccgtgctgag 60

-continued

```
acagctggct ctgctgctgt ggaagaacta caccctgcag aaacggaagg tgctcgtgac    120
cgtgctggaa ctgttcctgc ccctgctgtt cagcggcatc ctgatctggc tgcggctgaa    180
gatccagagc gagaacgtgc ccaacgccac catctacccc ggccagagca tccaggaact    240
gcccctgttc ttcaccttcc ccccacccgg cgatacctgg gagctggcct atatccctag    300
ccacagcgac gccgccaaga ccgtgacaga gacagtgcgg agagccctcg tgatcaacat    360
gagagtgcgg ggcttcccca gcgagaagga cttcgaggac tacatcagat acgacaactg    420
cagcagcagc gtgctggccg ccgtggtgtt tgagcacccc ttcaaccaca gcaaagagcc    480
cctgcctctg gccgtgaagt accacctgag attcagctac acccggcgga actacatgtg    540
gacccagacc ggctcattct tcctgaaaga gacagagggc tggcacacca ccagcctgtt    600
ccctctgttc cccaaccctg gccccagaga gcctacatct cctgacggcg gcgagcccgg    660
ctatatcaga gaaggattcc tggccgtgca gcacgccgtg gacagagcca tcatggaata    720
ccacgccgat gccgccaccc ggcagctgtt tcagagactg accgtgacca tcaagcggtt    780
cccttacccc ccctttatcg ccgacccttt cctggtggcc atccagtacc agctgccact    840
cctcctgctg ctgagcttta cctacaccgc cctgacaatc gccagagccg tggtgcagga    900
aaaagagcgg cggctgaaag agtacatgcg gatgatgggc ctgtccagct ggctgcattg    960
gagcgcctgg tttctgctgt tcttcctgtt cctgctgatc gccgccagct tcatgacact   1020
gctgttttgc gtgaaagtga agcccaacgt ggcagtgctg agccgcagcg atcctagcct   1080
ggtgctggcc ttcctgctgt gcttcgccat cagcaccatc agcttcagct ttatggtgtc   1140
caccttcttc agcaaggcca acatggccgc tgccttcggc ggcttcctgt acttctttac   1200
ctatattccc tacttcttcg tggcccctcg gtacaactgg atgaccctga gccagaagct   1260
gtgcagctgc ctgctgagca acgtggccat ggctatggga gcccagctga tcggcaagtt   1320
cgaggccaag ggcatgggca tccagtggcg ggatctgctg agccccgtga acgtggacga   1380
cgacttctgc ttcggccagg tgctgggcat gctgctgctg gactccgtgc tgtatggcct   1440
cgtgacctgg tatatggaag ccgtgttccc tggccagttc ggcgtgcccc agccctggta   1500
cttcttcatc atgcctagct attggtgcgg caagcccagg gccgtggccg gcaaagagga   1560
agaggatagc gaccccgaga aggccctgcg gaacgagtac tttgaggccg agcccgagga   1620
tctggtggcc ggaatcaaga tcaagcacct gagcaaggtg ttccgcgtgg gcaacaagga   1680
tagagccgct gtgcgggacc tgaacctgaa tctgtacgag ggccagatca ccgtgctgct   1740
gggccataat ggcgccggaa agaccaccac cctgagcatg ctgaccggcc tgtttccccc   1800
aacaagcggc agggcctaca tcagcggcta cgagatcagc caggacatgg tgcagatccg   1860
gaagtccctg ggcctgtgcc cccagcacga catcctgttc gacaacctga ccgtggccga   1920
gcacctgtac ttttacgctc agctgaaggg cctgagccgg cagaaatgcc ccgaggaagt   1980
gaagcagatg ctgcacatca tcggcctgga agataagtgg aacagccggt cccggttcct   2040
gtccggcgga atgagaagaa agctgagcat cggaatcgcc ctgattgccg gcagcaaggt   2100
gctgatcctg gacgagccta ccagcggcat ggacgccatc tccagaaggg ccatctggga   2160
cctgctgcag cggcagaagt ccgacagaac catcgtgctg accacccact tcatggacga   2220
ggccgacctg ctgggcgacc ggatcgctat tatggccaag gggggagctgc agtgctgcgg   2280
cagcagcctg tttctgaagc agaaatacgg cgctggctac cacatgaccc tcgtgaaaga   2340
gcctcactgc aaccccgagg acatctccca gctggtgcac caccacgtgc caaatgccac   2400
cctggaaagc tctgccggcg ctgagctgag cttcatcctg cccagagaga gcacccacag   2460
```

-continued attcgagggc ctgttcgcca agctggaaaa gaaacagaaa gagctgggca ttgccagctt 2520
cggcgccagc atcacaacaa tggaagaggt gttcctgaga gtgggcaagc tggtggacag 2580
ctccatggac atccaggcta tccagctgcc cgccctgcag tatcagcacg agagaagggc 2640
tagcgactgg gccgtggact ccaatctgtg cggcgccatg gatccctccg atggaatcgg 2700
cgccctgatc gaagaggaac ggaccgccgt gaagctgaac acaggactgg ccctgcactg 2760
ccagcagttc tgggccatgt tcctgaagaa agccgcctac agctggcgcg agtggaaaat 2820
ggtggccgca caggtgctgg tgcccctgac ctgtgtgaca ctggcactgc tggccatcaa 2880
ctacagcagc gagctgttcg acgaccccat gctgagactg acactgggcg agtacggcag 2940
gaccgtggtg cctttttctg tgcccggcac ctcacagctg ggccagcagc tgtctgaaca 3000
cctgaaggat gccctgcagg ccgaaggcca ggaacccaga gaagtgctgg gcgatctgga 3060
agagttcctg atcttccggg ccagcgtgga aggcggcgga ttcaacgaga gatgcctggt 3120
ggctgcctcc ttccgggatg tgggcgagag aacagtcgtg aacgccctgt tcaacaatca 3180
ggcctaccac agccccgcca ccgctctggc tgtggtggac aacctgctgt ttaagctgct 3240
gtgtggcccc cacgcctcca tcgtggtgtc caatttcccc cagcccagaa gcgctctgca 3300
ggctgccaag gaccagttca acgagggccg gaagggcttc gacattgctc tgaatctgct 3360
gtttgccatg gcctttctgg cctccacctt cagcatcctg gctgtgtccg agagagccgt 3420
gcaggccaag cacgtgcagt ttgtgtctgg cgtgcacgtg gccagctttt ggctgtctgc 3480
cctgctgtgg gacctgatca gcttcctgat ccccagcctc ctgctgctgg tggtgttcaa 3540
ggccttcgac gtgcgggcct tcaccaggga tggacacatg gccgacacct tgttgttgct 3600
gctgctgtac ggctgggcca tcatccccct gatgtacctg atgaacttct tcttcctggg 3660
cgctgccacc gcctacacca gactgaccat cttcaacatc ctgagcggga tcgccacctt 3720
cctgatggtc acaatcatgc ggatccctgc cgtgaaactg gaagaactga gcaagaccct 3780
ggaccatgtg tttctggtgc tgcccaacca ctgcctgggc atggccgtgt ctagcttcta 3840
cgagaactac gagacacggc ggtactgcac ctccagcgaa gtggccgccc actactgcaa 3900
gaagtataac atccagtatc aggaaaactt ctacgcttgg agcgcacccg gcgtgggcag 3960
atttgtggcc tctatggccg ccagcggctg cgcctatctg atcctgctgt tcctgatcga 4020
gactaacctg ctgcagagac tgagaggcat cctgtgcgcc ctgcggcgga gaagaacact 4080
gaccgagctg tacacccgga tgcccgtgct gcctgaggac caggatgtgg ccgacgagcg 4140
gacaagaatc ctggccccta gccccgatag cctgctgcac acccccctga tcatcaaaga 4200
actgtccaag gtgtacgagc agcgggtgcc actgctggct gtggacagac tgagtctggc 4260
tgtgcagaaa ggcgagtgct tcggactgct gggcttcaac ggcgcaggca agaccacaac 4320
cttcaagatg ctgacaggcg aggaaagcct gacctccggc gacgcctttg tgggcggaca 4380
caggatctct tccgatgtgg gcaaagtgcg gcagcggatc ggctactgcc ctcagttcga 4440
cgccctgctg gatcacatga ccggcaggga aatgctcgtg atgtacgccc ggctgagggg 4500
catccccgag agacacattg gcgcctgcgt ggaaaacacc ctgcggggcc tgctgctgga 4560
accccacgct aacaaactcg tgcggaccta cagcggcggc aacaagagaa agctgtctac 4620
cggcattgca ctgatcggcg agccagccgt gatctttctg gatgagccca gcacaggcat 4680
ggaccccgtg gctcggagac tgctgtggga tacagtggcc agagccagag agtccggcaa 4740
ggccatcatt atcaccagcc acagcatgga agagtgcgag gccctgtgta caagactggc 4800

-continued

```
aattatggtg cagggacagt tcaagtgtct gggcagccct cagcacctga agtccaagtt   4860

cggctccggc tacagcctgc gggccaaggt gcagtctgaa gggcagcagg aagccctgga   4920

agaattcaaa gccttcgtgg acctgacctt ccccggctct gtgctggaag atgagcacca   4980

gggaatggtg cactaccatc tgcctggcag ggacctgtcc tgggccaaag tgtttggcat   5040

cctggaaaag gccaaagaga agtacggcgt ggacgattac agcgtgtccc agatcagcct   5100

ggaacaggtg ttcctgtcct ttgcccatct gcagcccccct accgccgaag agggaagaac   5160

gcgtacgcga ccgctcgagc agaaactcat ctcagaagag gatctggcag caaatgatat   5220

cctggattac aaggatgacg acgataaggt ttgacctcgc ccggacctg ccctcccgcc   5280

aggtgcaccc acctgcaata aatgcagcga agccgggaaa aaaaaaaaaa aaaaaaaaaa   5340

aaaaaaaaaa aaaaaaaaaa aaaaaaaaaa aaaaaaaaaa aaaaaaaaaa aaaaaaaaaa   5400

aaaaaaaaaa aaaaaaaaaa aaaaaaaaaa aaaaaaaaat t                       5441
```

<210> SEQ ID NO 13
<211> LENGTH: 5441
<212> TYPE: RNA
<213> ORGANISM: Artificial
<220> FEATURE:
<223> OTHER INFORMATION: codon optimized ABCA3 mRNA sequence with a 5' CYBA UTR and a 3' CYBA UTR

<400> SEQUENCE: 13

```
agaccgcgcc uagcagugu c ccagccgggu ucgugucgcc gccaccaugg ccgugcugag     60

acagcuggcu cugcugcugu ggaagaacua cacccugcag aaacggaagg ugcucgugac    120

cgugcuggaa cuguuccugc cccugcuguu cagcggcauc cugaucuggc ugcggcugaa    180

gauccagagc gagaacgugc ccaacgccac caucuacccc ggccagagca uccaggaacu    240

gccccuguuc uucaccuucc ccccacccgg cgauaccugg gagcuggccu auaucccuag    300

ccacagcgac gccgccaaga ccgugacaga gacagugcgg agagcccucg ugaucaacau    360

gagagugcgg ggcuucccca gcgagaagga cuucgaggac uacaucagau acgacaacug    420

cagcagcagc gugcuggccg ccgugguguu ugagcacccc uucaaccaca gcaaagagcc    480

ccugccucug gccgugaagu accaccugag auucagcuac acccggcgga acuacaugug    540

gacccagacc ggcucauucu uccugaaaga gacagagggc uggcacacca ccagccuguu    600

cccucuguuc cccaacccug gccccagaga gccuacaucu ccugacggcg gcgagcccgg    660

cuauaucaga gaaggauucc uggccgugca gcacgccgug gacagagcca ucauggaaua    720

ccacgccgau gccgccaccc ggcagcuguu ucagagacug accgugacca ucaagcgguu    780

cccuuacccc cccuuuaucg ccgacccuuu ccugguggcc auccaguacc agcugccacu    840

ccuccugcug cugagcuuua ccuacaccgc ccugacaauc gccagagccg uggugcagga    900

aaaagagcgg cggcugaaag aguacaugcg gaugaugggc cuguccagcu ggcugcauug    960

gagcgccugg uuucugcugu ucuuccuguu ccugcugauc gccgccagcu ucaugacacu   1020

gcuguuuugc gugaaaguga agcccaacgu ggcagugcug agccgcagcg auccuagccu   1080

ggugcuggcc uuccugcugu gcuucgccau cagcaccauc agcuucagcu uuauggugu c  1140

caccuucuuc agcaaggcca acauggccgc ugccuucggc ggcuuccugu acuucuuuac   1200

cuauauuccc uacuucuucg uggccccucg guacaacugg augacccuga gccagaagcu   1260

gugcagcugc cugcugagca acguggccau ggcuauggga gcccagcuga ucggcaaguu   1320

cgaggccaag ggcaugggca uccaguggcg ggaucugcug agccccguga acguggacga   1380
```

-continued cgacuucugc uucggccagg ugcugggcau gcugcugcug gacuccgugc uguauggccu 1440
cgugaccugg uauauggaag ccguguuccc uggccaguuc ggcgugcccc agcccuggua 1500
cuucuucauc augccuagcu auuggugcgg caagcccagg gccguggccg gcaaagagga 1560
agaggauagc gaccccgaga aggcccugcg gaacgaguac uuugaggccg agcccgagga 1620
ucugguggcc ggaaucaaga ucaagcaccu gagcaaggug uuccgcgugg gcaacaagga 1680
uagagccgcu gugcgggacc ugaaccugaa ucuguacgag ggccagauca ccgugcugcu 1740
gggccauaau ggcgccggaa agaccaccac ccugagcaug cugaccggcc uguuuccccc 1800
aacaagcggc agggccuaca ucagcggcua cgagaucagc caggacaugg ugcagauccg 1860
gaagucccug ggccugugcc cccagcacga cauccuguuc gacaaccuga ccguggccga 1920
gcaccuguac uuuuacgcuc agcugaaggg ccugagccgg cagaaaugcc ccgaggaagu 1980
gaagcagaug cugcacauca ucggccugga agauaagugg aacagccggu cccgguuccu 2040
guccggcgga augagaagaa agcugagcau cggaaucgcc cugauugccg gcagcaaggu 2100
gcugauccug gacgagccua ccagcggcau ggacgccauc uccagaaggg ccaucuggga 2160
ccugcugcag cggcagaagu ccgacagaac caucgugcug accacccacu ucauggacga 2220
ggccgaccug cugggcgacc ggaucgcuau uauggccaag gggggagcugc agugcugcgg 2280 cagcagccug uuucugaagc agaaauacgg cgcuggcuac cacaugaccc ucgugaaaga 2340
gccucacugc aaccccgagg acaucuccca gcuggugcac caccacgugc caaaugccac 2400
ccuggaaagc ucugccggcg cugagcugag cuucauccug cccagagaga gcacccacag 2460
auucgagggc cuguucgcca agcuggaaaa gaaacagaaa gagcugggca uugccagcuu 2520
cggcgccagc aucacaacaa uggaagaggu guuccugaga gugggcaagc ugguggacag 2580
cuccauggac auccaggcua uccagcugcc cgcccugcag uaucagcacg agagaagggc 2640
uagcgacugg gccguggacu ccaaucugug cggcgccaug gaucccuccg auggaaucgg 2700
cgcccugauc gaagaggaac ggaccgccgu gaagcugaac acaggacugg cccugcacug 2760
ccagcaguuc ugggccaugu uccugaagaa agccgccuac agcuggcgcg aguggaaaau 2820
gguggccgca caggugcugg ugccccugac cugugugaca cuggcacugc uggccaucaa 2880
cuacagcagc gagcuguucg acgaccccau gcugagacug acacugggcg aguacggcag 2940
gaccguggug ccuuuuucug ugcccggcac cucacagcug ggccagcagc ugucugaaca 3000
ccugaaggau gcccugcagg ccgaaggcca ggaacccaga gaagugcugg gcgaucugga 3060
agaguuccug aucuuccggg ccagcgugga aggcggcgga uucaacgaga gaugccuggu 3120
ggcugccucc uuccgggaug ugggcgagag aacagucgug aacgcccugu ucaacaauca 3180
ggccuaccac agccccgcca ccgcucuggc ugugguggac aaccugcugu uuaagcugcu 3240
guguggcccc cacgccucca ucgugguguc caauuucccc cagcccagaa gcgcucugca 3300
ggcugccaag gaccaguuca acgagggccg gaagggcuuc gacauugcuc ugaaucugcu 3360
guuugccaug gccuuucugg ccuccaccuu cagcauccug gcugugucg agagagccgu 3420 gcaggccaag cacgugcagu uugugucugg cgugcacgug gccagcuuuu ggcugucugc 3480
ccugcugugg gaccugauca gcuuccugau ccccagccuc cugcugcugg ugguguucaa 3540
ggccuucgac gugcgggccu ucaccaggga uggacacaug gccgacaccu uguuguugcu 3600
gcugcuguac ggcugggcca ucaucccccu gauguaccug augaacuucu ucuuccuggg 3660
cgcugccacc gccuacacca gacugaccau cuucaacauc cugagcggga ucgccaccuu 3720 ccugauggoc acaaucaugc ggaucccugc cgugaaacug gaagaacuga gcaagacccu 3780
ggaccaugug uuucuggugc ugcccaacca cugccugggc auggccgugu cuagcuucua 3840
cgagaacuac gagacacggc gguacugcac cuccagcgaa guggccgccc acuacugcaa 3900
gaaguauaac auccaguauc aggaaaacuu cuacgcuugg agcgcacccg gcgugggcag 3960
auuuguggcc ucuauggccg ccagcggcug cgccuaucug auccugcugu uccugaucga 4020
gacuaaccug cugcagagac ugagaggcau ccugugcgcc cugcggcgga gaagaacacu 4080
gaccgagcug uacacccgga ugcccgugcu gccugaggac caggaugugg ccgacgagcg 4140
gacaagaauc cuggccccua gccccgauag ccugcugcac accccccuga ucaucaaaga 4200
acuguccaag guguacgagc agcgggugcc acugcuggcu guggacagac ugagucuggc 4260
ugugcagaaa ggcgagugcu ucggacugcu gggcuucaac ggcgcaggca agaccacaac 4320
cuucaagaug cugacaggcg aggaaagccu gaccuccggc gacgccuuug ugggcggaca 4380
caggaucucu uccgaugugg gcaaagugcg gcagcggauc ggcuacugcc cucaguucga 4440
cgcccugcug gaucacauga ccggcaggga aaugcucgug auguacgccc ggcugagggg 4500
cauccccgag agacacauug gcgccugcgu ggaaaacacc cugcggggcc ugcugcugga 4560
accccacgcu aacaaacucg ugcggaccua cagcggcggc aacaagagaa agcugucuac 4620
cggcauugca cugaucggcg agccagccgu gaucuuucug gaugagccca gcacaggcau 4680
ggaccccgug gcucggagac ugcuguggga uacaguggcc agagccagag aguccggcaa 4740
ggccaucauu aucaccagcc acagcaugga agagugcgag gcccugugua caagacuggc 4800
aauuauggug cagggacagu ucaagugucu gggcagcccu cagcaccuga aguccaaguu 4860
cggcuccggc uacagccugc gggccaaggu gcagucugaa gggcagcagg aagcccugga 4920
agaauucaaa gccuucgugg accugaccuu ccccggcucu gugcuggaag augagcacca 4980
gggaauggug cacuaccauc ugccuggcag ggaccugucc ugggccaaag uguuuggcau 5040
ccuggaaaag gccaaagaga aguacggcgu ggacgauuac agcgugucccc agaucagccu 5100 ggaacaggug uuccuguccu uugcccaucu gcagcccccu accgccgaag agggaagaac 5160
gcguacgcga ccgcucgagc agaaacucau cucagaagag gaucuggcag caaaugauau 5220
ccuggauuac aaggaugacg acgauaaggu uugaccucgc cccggaccug cccucccgcc 5280
aggugcaccc accugcaaua aaugcagcga agccgggaaa aaaaaaaaaa aaaaaaaaaa 5340
aaaaaaaaaa aaaaaaaaaa aaaaaaaaaa aaaaaaaaaa aaaaaaaaaa aaaaaaaaaa 5400
aaaaaaaaaa aaaaaaaaaa aaaaaaaaaa aaaaaaaaau u 5441

<210> SEQ ID NO 14
<211> LENGTH: 36
<212> TYPE: RNA
<213> ORGANISM: Artificial
<220> FEATURE:
<223> OTHER INFORMATION: mRNA counterpart of SEQ ID NO: 1

<400> SEQUENCE: 14
cgcgccuagc agugucccag ccggguucgu gucgcc 36

<210> SEQ ID NO 15
<211> LENGTH: 64
<212> TYPE: RNA
<213> ORGANISM: Artificial
<220> FEATURE:
<223> OTHER INFORMATION: mRNA counterpart of SEQ ID NO: 2

<400> SEQUENCE: 15

-continued ccucgccccg gaccugcccu cccgccaggu gcacccaccu gcaauaaaug cagcgaagcc 60
ggga 64

<210> SEQ ID NO 16
<211> LENGTH: 30
<212> TYPE: RNA
<213> ORGANISM: Artificial
<220> FEATURE:
<223> OTHER INFORMATION: mRNA counterpart of SEQ ID NO: 5

<400> SEQUENCE: 16
ucuucugguc cccacagacu cagagagaac 30

<210> SEQ ID NO 17
<211> LENGTH: 5407
<212> TYPE: DNA
<213> ORGANISM: Artificial
<220> FEATURE:
<223> OTHER INFORMATION: Transcript TTX-ABCA3-RNA-018

<400> SEQUENCE: 17
gggagaccca agctggctag cgtttaaact taagcttggc aatccggtac tgttggtaaa 60
gccaccatgg ccgtgctgag acagctggct ctgctgctgt ggaagaacta caccctgcag 120
aaacggaagg tgctcgtgac cgtgctggaa ctgttcctgc ccctgctgtt cagcggcatc 180
ctgatctggc tgcggctgaa gatccagagc gagaacgtgc ccaacgccac catctacccc 240
ggccagagca tccaggaact gcccctgttc ttcaccttcc ccccacccgg cgatacctgg 300
gagctggcct atatccctag ccacagcgac gccgccaaga ccgtgacaga gacagtgcgg 360
agagccctcg tgatcaacat gagagtgcgg ggcttcccca gcgagaagga cttcgaggac 420
tacatcagat acgacaactg cagcagcagc gtgctggccg ccgtggtgtt tgagcacccc 480
ttcaaccaca gcaaagagcc cctgcctctg gccgtgaagt accacctgag attcagctac 540
acccggcgga actacatgtg gacccagacc ggctcattct tcctgaaaga gacagagggc 600
tggcacacca ccagcctgtt ccctctgttc cccaaccctg gccccagaga gcctacatct 660
cctgacggcg gcgagcccgg ctatatcaga gaaggattcc tggccgtgca gcacgccgtg 720
gacagagcca tcatggaata ccacgccgat gccgccaccc ggcagctgtt tcagagactg 780
accgtgacca tcaagcggtt ccccttaccc ccctttatcg ccgacccttt cctggtggcc 840
atccagtacc agctgccact cctcctgctg ctgagcttta cctacaccgc cctgacaatc 900
gccagagccg tggtgcagga aaaagagcgg cggctgaaag agtacatgcg gatgatgggc 960
ctgtccagct ggctgcattg gagcgcctgg tttctgctgt tcttcctgtt cctgctgatc 1020
gccgccagct tcatgacact gctgttttgc gtgaaagtga agcccaacgt ggcagtgctg 1080
agccgcagcg atcctagcct ggtgctggcc ttcctgctgt gcttcgccat cagcaccatc 1140
agcttcagct ttatggtgtc caccttcttc agcaaggcca acatggccgc tgccttcggc 1200
ggcttcctgt acttctttac ctatattccc tacttcttcg tggcccctcg gtacaactgg 1260
atgaccctga gccagaagct gtgcagctgc ctgctgagca acgtggccat ggctatggga 1320
gcccagctga tcggcaagtt cgaggccaag ggcatgggca tccagtggcg ggatctgctg 1380
agccccgtga acgtggacga cgacttctgc ttcggccagg tgctgggcat gctgctgctg 1440
gactccgtgc tgtatggcct cgtgacctgg tatatggaag ccgtgttccc tggccagttc 1500
ggcgtgcccc agccctggta cttcttcatc atgcctagct attggtgcgg caagcccagg 1560
gccgtggccg gcaaagagga agaggatagc gaccccgaga aggccctgcg gaacgagtac 1620

```
tttgaggccg agcccgagga tctggtggcc ggaatcaaga tcaagcacct gagcaaggtg   1680
ttccgcgtgg gcaacaagga tagagccgct gtgcgggacc tgaacctgaa tctgtacgag   1740
ggccagatca ccgtgctgct gggccataat ggcgccggaa agaccaccac cctgagcatg   1800
ctgaccggcc tgtttccccc aacaagcggc agggcctaca tcagcggcta cgagatcagc   1860
caggacatgg tgcagatccg gaagtccctg ggcctgtgcc cccagcacga catcctgttc   1920
gacaacctga ccgtggccga gcacctgtac ttttacgctc agctgaaggg cctgagccgg   1980
cagaaatgcc ccgaggaagt gaagcagatg ctgcacatca tcggcctgga agataagtgg   2040
aacagccggt cccggttcct gtccggcgga atgagaagaa agctgagcat cggaatcgcc   2100
ctgattgccg gcagcaaggt gctgatcctg gacgagccta ccagcggcat ggacgccatc   2160
tccagaaggg ccatctggga cctgctgcag cggcagaagt ccgacagaac catcgtgctg   2220
accacccact tcatggacga ggccgacctg ctgggcgacc ggatcgctat tatggccaag   2280
ggggagctgc agtgctgcgg cagcagcctg tttctgaagc agaaatacgg cgctggctac   2340
cacatgaccc tcgtgaaaga gcctcactgc aaccccgagg acatctccca gctggtgcac   2400
caccacgtgc caaatgccac cctggaaagc tctgccggcg ctgagctgag cttcatcctg   2460
cccagagaga gcacccacag attcgagggc ctgttcgcca agctggaaaa gaaacagaaa   2520
gagctgggca ttgccagctt cggcgccagc atcacaacaa tggaagaggt gttcctgaga   2580
gtgggcaagc tggtggacag ctccatggac atccaggcta tccagctgcc cgccctgcag   2640
tatcagcacg agagaagggc tagcgactgg gccgtggact ccaatctgtg cggcgccatg   2700
gatccctccg atggaatcgg cgccctgatc gaagaggaac ggaccgccgt gaagctgaac   2760
acaggactgg ccctgcactg ccagcagttc tgggccatgt tcctgaagaa agccgcctac   2820
agctggcgcg agtggaaaat ggtggccgca caggtgctgg tgcccctgac ctgtgtgaca   2880
ctggcactgc tggccatcaa ctacagcagc gagctgttcg acgaccccat gctgagactg   2940
acactgggcg agtacggcag gaccgtggtg cctttttctg tgcccggcac ctcacagctg   3000
ggccagcagc tgtctgaaca cctgaaggat gccctgcagg ccgaaggcca ggaacccaga   3060
gaagtgctgg gcgatctgga agagttcctg atcttccggg ccagcgtgga aggcggcgga   3120
ttcaacgaga gatgcctggt ggctgcctcc ttccgggatg tgggcgagag aacagtcgtg   3180
aacgccctgt tcaacaatca ggcctaccac agccccgcca ccgctctggc tgtggtggac   3240
aacctgctgt ttaagctgct gtgtggcccc cacgcctcca tcgtggtgtc caatttcccc   3300
cagcccagaa gcgctctgca ggctgccaag gaccagttca acgagggccg gaagggcttc   3360
gacattgctc tgaatctgct gtttgccatg gcctttctgg cctccacctt cagcatcctg   3420
gctgtgtccg agagagccgt gcaggccaag cacgtgcagt ttgtgtctgg cgtgcacgtg   3480
gccagctttt ggctgtctgc cctgctgtgg gacctgatca gcttcctgat ccccagcctc   3540
ctgctgctgg tggtgttcaa ggccttcgac gtgcgggcct tcaccaggga tggacacatg   3600
gccgacacct tgttgttgct gctgctgtac ggctgggcca tcatccccct gatgtacctg   3660
atgaacttct tcttcctggg cgctgccacc gcctacacca gactgaccat cttcaacatc   3720
ctgagcggga tcgccacctt cctgatggtc acaatcatgc ggatccctgc cgtgaaactg   3780
gaagaactga gcaagaccct ggaccatgtg tttctggtgc tgcccaacca ctgcctgggc   3840
atggccgtgt ctagcttcta cgagaactac gagacacggc ggtactgcac ctccagcgaa   3900
gtggccgccc actactgcaa gaagtataac atccagtatc aggaaaactt ctacgcttgg   3960
```

-continued agcgcacccg gcgtgggcag atttgtggcc tctatggccg ccagcggctg cgcctatctg 4020
atcctgctgt tcctgatcga gactaacctg ctgcagagac tgagaggcat cctgtgcgcc 4080
ctgcggcgga gaagaacact gaccgagctg tacacccgga tgcccgtgct gcctgaggac 4140
caggatgtgg ccgacgagcg gacaagaatc ctggccccta gccccgatag cctgctgcac 4200
acccccctga tcatcaaaga actgtccaag gtgtacgagc agcgggtgcc actgctggct 4260
gtggacagac tgagtctggc tgtgcagaaa ggcgagtgct tcggactgct gggcttcaac 4320
ggcgcaggca agaccacaac cttcaagatg ctgacaggcg aggaaagcct gacctccggc 4380
gacgcctttg tgggcggaca caggatctct tccgatgtgg gcaaagtgcg gcagcggatc 4440
ggctactgcc ctcagttcga cgccctgctg gatcacatga ccggcaggga aatgctcgtg 4500
atgtacgccc ggctgagggg catccccgag agacacattg gcgcctgcgt ggaaaacacc 4560
ctgcggggcc tgctgctgga accccacgct aacaaactcg tgcggaccta cagcggcggc 4620
aacaagagaa agctgtctac cggcattgca ctgatcggcg agccagccgt gatctttctg 4680
gatgagccca gcacaggcat ggaccccgtg gctcggagac tgctgtggga tacagtggcc 4740
agagccagag agtccggcaa ggccatcatt atcaccagcc acagcatgga agagtgcgag 4800
gccctgtgta caagactggc aattatggtg cagggacagt tcaagtgtct gggcagccct 4860
cagcacctga agtccaagtt cggctccggc tacagcctgc gggccaaggt gcagtctgaa 4920
gggcagcagg aagccctgga agagttcaaa gccttcgtgg acctgacctt ccccggctct 4980
gtgctggaag atgagcacca gggaatggtg cactaccatc tgcctggcag ggacctgtcc 5040
tgggccaaag tgtttggcat cctggaaaag gccaaagaga agtacggcgt ggacgattac 5100
agcgtgtccc agatcagcct ggaacaggtg ttcctgtcct ttgcccatct gcagcccccct 5160 accgccgaag agggaagaac gcgtacgcgg ccgctcgagc agaaactcat ctcagaagag 5220
gatctggcag caaatgatat cctggattac aaggatgacg acgataaggt ttaagaattc 5280
tgcagaaaaa aaaaaaaaaa aaaaaaaaaa aaaaaaaaaa aaaaaaaaaa aaaaaaaaaa 5340
aaaaaaaaaa aaaaaaaaaa aaaaaaaaaa aaaaaaaaaa aaaaaaaaaa aaaaaaaaaa 5400
aaaaagc 5407

<210> SEQ ID NO 18
<211> LENGTH: 5384
<212> TYPE: DNA
<213> ORGANISM: Artificial
<220> FEATURE:
<223> OTHER INFORMATION: Transcript TTX-ABCA3-RNA-019

<400> SEQUENCE: 18
gggagactct tctggtcccc acagactcag agagaacgcc accatggccg tgctgagaca 60
gctggctctg ctgctgtgga agaactacac cctgcagaaa cggaaggtgc tcgtgaccgt 120
gctggaactg ttcctgcccc tgctgttcag cggcatcctg atctggctgc ggctgaagat 180
ccagagcgag aacgtgccca acgccaccat ctaccccggc cagagcatcc aggaactgcc 240
cctgttcttc accttccccc cacccggcga tacctgggag ctggcctata tccctagcca 300
cagcgacgcc gccaagaccg tgacagagac agtgcggaga gccctcgtga tcaacatgag 360
agtgcggggc ttccccagcg agaaggactt cgaggactac atcagatacg acaactgcag 420
cagcagcgtg ctggccgccg tggtgtttga gcaccccttc aaccacagca aagagcccct 480
gcctctggcc gtgaagtacc acctgagatt cagctacacc cggcggaact acatgtggac 540
ccagaccggc tcattcttcc tgaaagagac agagggctgg cacaccacca gcctgttccc 600

```
tctgttcccc aaccctggcc ccagagagcc tacatctcct gacggcggcg agcccggcta    660
tatcagagaa ggattcctgg ccgtgcagca cgccgtggac agagccatca tggaatacca    720
cgccgatgcc gccacccggc agctgtttca gagactgacc gtgaccatca agcggttccc    780
ttaccccccc tttatcgccg accctttcct ggtggccatc cagtaccagc tgccactcct    840
cctgctgctg agctttacct acaccgccct gacaatcgcc agagccgtgg tgcaggaaaa    900
agagcggcgg ctgaaagagt acatgcggat gatgggcctg tccagctggc tgcattggag    960
cgcctggttt ctgctgttct tcctgttcct gctgatcgcc gccagcttca tgacactgct   1020
gttttgcgtg aaagtgaagc ccaacgtggc agtgctgagc cgcagcgatc ctagcctggt   1080
gctggccttc ctgctgtgct tcgccatcag caccatcagc ttcagcttta tggtgtccac   1140
cttcttcagc aaggccaaca tggccgctgc cttcggcggc ttcctgtact tctttaccta   1200
tattccctac ttcttcgtgg cccctcggta caactggatg accctgagcc agaagctgtg   1260
cagctgcctg ctgagcaacg tggccatggc tatgggagcc cagctgatcg gcaagttcga   1320
ggccaagggc atgggcatcc agtggcggga tctgctgagc cccgtgaacg tggacgacga   1380
cttctgcttc ggccaggtgc tgggcatgct gctgctggac tccgtgctgt atggcctcgt   1440
gacctggtat atggaagccg tgttccctgg ccagttcggc gtgccccagc cctggtactt   1500
cttcatcatg cctagctatt ggtgcggcaa gcccagggcc gtggccggca aagaggaaga   1560
ggatagcgac cccgagaagg ccctgcggaa cgagtacttt gaggccgagc ccgaggatct   1620
ggtggccgga atcaagatca agcacctgag caaggtgttc cgcgtgggca acaaggatag   1680
agccgctgtg cgggacctga acctgaatct gtacgagggc cagatcaccg tgctgctggg   1740
ccataatggc gccggaaaga ccaccaccct gagcatgctg accggcctgt ttcccccaac   1800
aagcggcagg gcctacatca gcggctacga gatcagccag gacatggtgc agatccggaa   1860
gtccctgggc ctgtgccccc agcacgacat cctgttcgac aacctgaccg tggccgagca   1920
cctgtacttt tacgctcagc tgaagggcct gagccggcag aaatgccccg aggaagtgaa   1980
gcagatgctg cacatcatcg gcctggaaga taagtggaac agccggtccc ggttcctgtc   2040
cggcggaatg agaagaaagc tgagcatcgg aatcgccctg attgccggca gcaaggtgct   2100
gatcctggac gagcctacca gcggcatgga cgccatctcc agaagggcca tctgggacct   2160
gctgcagcgg cagaagtccg acagaaccat cgtgctgacc acccacttca tggacgaggc   2220
cgacctgctg ggcgaccgga tcgctattat ggccaagggg gagctgcagt gctgcggcag   2280
cagcctgttt ctgaagcaga aatacggcgc tggctaccac atgaccctcg tgaaagagcc   2340
tcactgcaac cccgaggaca tctcccagct ggtgcaccac cacgtgccaa atgccaccct   2400
ggaaagctct gccggcgctg agctgagctt catcctgccc agagagagca cccacagatt   2460
cgagggcctg ttcgccaagc tggaaaagaa acagaaagag ctgggcattg ccagcttcgg   2520
cgccagcatc acaacaatgg aagaggtgtt cctgagagtg ggcaagctgg tggacagctc   2580
catggacatc caggctatcc agctgcccgc cctgcagtat cagcacgaga gaagggctag   2640
cgactgggcc gtggactcca atctgtgcgg cgccatggat ccctccgatg gaatcggcgc   2700
cctgatcgaa gaggaacgga ccgccgtgaa gctgaacaca ggactggccc tgcactgcca   2760
gcagttctgg gccatgttcc tgaagaaagc cgcctacagc tggcgcgagt ggaaaatggt   2820
ggccgcacag gtgctggtgc ccctgacctg tgtgacactg gcactgctgg ccatcaacta   2880
cagcagcgag ctgttcgacg accccatgct gagactgaca ctgggcgagt acggcaggac   2940
```

-continued

```
cgtggtgcct ttttctgtgc ccggcacctc acagctgggc cagcagctgt ctgaacacct   3000
gaaggatgcc ctgcaggccg aaggccagga acccagagaa gtgctgggcg atctggaaga   3060
gttcctgatc ttccgggcca gcgtggaagg cggcggattc aacgagagat gcctggtggc   3120
tgcctccttc cgggatgtgg gcgagagaac agtcgtgaac gccctgttca acaatcaggc   3180
ctaccacagc cccgccaccg ctctggctgt ggtggacaac ctgctgttta agctgctgtg   3240
tggcccccac gcctccatcg tggtgtccaa tttcccccag cccagaagcg ctctgcaggc   3300
tgccaaggac cagttcaacg agggccggaa gggcttcgac attgctctga atctgctgtt   3360
tgccatggcc tttctggcct ccaccttcag catcctggct gtgtccgaga gagccgtgca   3420
ggccaagcac gtgcagtttg tgtctggcgt gcacgtggcc agcttttggc tgtctgccct   3480
gctgtgggac ctgatcagct tcctgatccc cagcctcctg ctgctggtgg tgttcaaggc   3540
cttcgacgtg cgggccttca ccagggatgg acacatggcc gacaccttgt tgttgctgct   3600
gctgtacggc tgggccatca tcccccctgat gtacctgatg aacttcttct tcctgggcgc   3660
tgccaccgcc tacaccagac tgaccatctt caacatcctg agcgggatcg ccaccttcct   3720
gatggtcaca atcatgcgga tccctgccgt gaaactggaa gaactgagca agaccctgga   3780
ccatgtgttt ctggtgctgc ccaaccactg cctgggcatg gccgtgtcta gcttctacga   3840
gaactacgag acacggcggt actgcacctc cagcgaagtg gccgcccact actgcaagaa   3900
gtataacatc cagtatcagg aaaacttcta cgcttggagc gcacccggcg tgggcagatt   3960
tgtggcctct atggccgcca gcggctgcgc ctatctgatc ctgctgttcc tgatcgagac   4020
taacctgctg cagagactga gaggcatcct gtgcgccctg cggcggagaa gaacactgac   4080
cgagctgtac acccggatgc ccgtgctgcc tgaggaccag gatgtggccg acgagcggac   4140
aagaatcctg gcccctagcc ccgatagcct gctgcacacc cccctgatca tcaaagaact   4200
gtccaaggtg tacgagcagc gggtgccact gctggctgtg gacagactga gtctggctgt   4260
gcagaaaggc gagtgcttcg gactgctggg cttcaacggc gcaggcaaga ccacaacctt   4320
caagatgctg acaggcgagg aaagcctgac ctccggcgac gcctttgtgg gcggacacag   4380
gatctcttcc gatgtgggca aagtgcggca gcggatcggc tactgccctc agttcgacgc   4440
cctgctggat cacatgaccg gcagggaaat gctcgtgatg tacgcccggc tgaggggcat   4500
ccccgagaga cacattggcg cctgcgtgga aaacaccctg cggggcctgc tgctggaacc   4560
ccacgctaac aaactcgtgc ggacctacag cggcggcaac aagagaaagc tgtctaccgg   4620
cattgcactg atcggcgagc cagccgtgat ctttctggat gagcccagca caggcatgga   4680
ccccgtggct cggagactgc tgtgggatac agtggccaga gccagagagt ccggcaaggc   4740
catcattatc accagccaca gcatggaaga gtgcgaggcc ctgtgtacaa gactggcaat   4800
tatggtgcag ggacagttca agtgtctggg cagccctcag cacctgaagt ccaagttcgg   4860
ctccggctac agcctgcggg ccaaggtgca gtctgaaggg cagcaggaag ccctggaaga   4920
attcaaagcc ttcgtggacc tgaccttccc cggctctgtg ctggaagatg agcaccaggg   4980
aatggtgcac taccatctgc ctggcaggga cctgtcctgg gccaaagtgt ttggcatcct   5040
ggaaaaggcc aaagagaagt acggcgtgga cgattacagc gtgtcccaga tcagcctgga   5100
acaggtgttc ctgtcctttg cccatctgca gcccccctacc gccgaagagg gaagaacgcg   5160
tacgcggccg ctcgagcaga aactcatctc agaagaggat ctggcagcaa atgatatcct   5220
ggattacaag gatgacgacg ataaggttta agaattctgc agaaaaaaaa aaaaaaaaaa   5280
aaaaaaaaaa aaaaaaaaaa aaaaaaaaaa aaaaaaaaaa aaaaaaaaaa aaaaaaaaaa   5340
```

aaaaaaaaaa aaaaaaaaaa aaaaaaaaaa aaaaaaaaaa aagc 5384

<210> SEQ ID NO 19
<211> LENGTH: 5178
<212> TYPE: DNA
<213> ORGANISM: Artificial
<220> FEATURE:
<223> OTHER INFORMATION: codon optimized ABCA3 sequence without any tags (-FLAG and Myc tags)

<400> SEQUENCE: 19
gggagaccca agctggctag cgtttaaact taagcttggc aatccggtac tgttggtaaa 60
gccaccatgg ccgtgctgag acagctggct ctgctgctgt ggaagaacta caccctgcag 120
aaacggaagg tgctcgtgac cgtgctggaa ctgttcctgc ccctgctgtt cagcggcatc 180
ctgatctggc tgcggctgaa gatccagagc gagaacgtgc ccaacgccac catctacccc 240
ggccagagca tccaggaact gcccctgttc ttcaccttcc ccccacccgg cgatacctgg 300
gagctggcct atatccctag ccacagcgac gccgccaaga ccgtgacaga gacagtgcgg 360
agagccctcg tgatcaacat gagagtgcgg ggcttcccca gcgagaagga cttcgaggac 420
tacatcagat acgacaactg cagcagcagc gtgctggccg ccgtggtgtt tgagcacccc 480
ttcaaccaca gcaaagagcc cctgcctctg gccgtgaagt accacctgag attcagctac 540
acccggcgga actacatgtg gacccagacc ggctcattct tcctgaaaga gacagagggc 600
tggcacacca ccagcctgtt ccctctgttc cccaaccctg gccccagaga gcctacatct 660
cctgacggcg gcgagcccgg ctatatcaga gaaggattcc tggccgtgca gcacgccgtg 720
gacagagcca tcatggaata ccacgccgat gccgccaccc ggcagctgtt tcagagactg 780
accgtgacca tcaagcggtt ccccttaccc cccttttatcg ccgacccttt cctggtggcc 840
atccagtacc agctgccact cctcctgctg ctgagcttta cctacaccgc cctgacaatc 900
gccagagccg tggtgcagga aaaagagcgg cggctgaaag agtacatgcg gatgatgggc 960
ctgtccagct ggctgcattg gagcgcctgg tttctgctgt tcttcctgtt cctgctgatc 1020
gccgccagct tcatgacact gctgttttgc gtgaaagtga agcccaacgt ggcagtgctg 1080
agccgcagcg atcctagcct ggtgctggcc ttcctgctgt gcttcgccat cagcaccatc 1140
agcttcagct ttatggtgtc caccttcttc agcaaggcca acatggccgc tgccttcggc 1200
ggcttcctgt acttctttac ctatattccc tacttcttcg tggcccctcg gtacaactgg 1260
atgaccctga gccagaagct gtgcagctgc ctgctgagca acgtggccat ggctatggga 1320
gcccagctga tcggcaagtt cgaggccaag ggcatgggca tccagtggcg ggatctgctg 1380
agccccgtga acgtggacga cgacttctgc ttcggccagg tgctgggcat gctgctgctg 1440
gactccgtgc tgtatggcct cgtgacctgg tatatggaag ccgtgttccc tggccagttc 1500
ggcgtgcccc agccctggta cttcttcatc atgcctagct attggtgcgg caagcccagg 1560
gccgtggccg gcaaagagga agaggatagc gaccccgaga aggccctgcg gaacgagtac 1620
tttgaggccg agcccgagga tctggtggcc ggaatcaaga tcaagcacct gagcaaggtg 1680
ttccgcgtgg gcaacaagga tagagccgct gtgcgggacc tgaacctgaa tctgtacgag 1740
ggccagatca ccgtgctgct gggccataat ggcgccggaa agaccaccac cctgagcatg 1800
ctgaccggcc tgtttccccc aacaagcggc agggcctaca tcagcggcta cgagatcagc 1860
caggacatgg tgcagatccg gaagtccctg ggcctgtgcc cccagcacga catcctgttc 1920
gacaacctga ccgtggccga gcacctgtac ttttacgctc agctgaaggg cctgagccgg 1980

-continued

```
cagaaatgcc ccgaggaagt gaagcagatg ctgcacatca tcggcctgga agataagtgg   2040
aacagccggt cccggttcct gtccggcgga atgagaagaa agctgagcat cggaatcgcc   2100
ctgattgccg gcagcaaggt gctgatcctg gacgagccta ccagcggcat ggacgccatc   2160
tccagaaggg ccatctggga cctgctgcag cggcagaagt ccgacagaac catcgtgctg   2220
accacccact tcatggacga ggccgacctg ctgggcgacc ggatcgctat tatggccaag   2280
ggggagctgc agtgctgcgg cagcagcctg tttctgaagc agaaatacgg cgctggctac   2340
cacatgaccc tcgtgaaaga gcctcactgc aaccccgagg acatctccca gctggtgcac   2400
caccacgtgc caaatgccac cctggaaagc tctgccggcg ctgagctgag cttcatcctg   2460
cccagagaga gcacccacag attcgagggc ctgttcgcca agctggaaaa gaaacagaaa   2520
gagctgggca ttgccagctt cggcgccagc atcacaacaa tggaagaggt gttcctgaga   2580
gtgggcaagc tggtggacag ctccatggac atccaggcta tccagctgcc cgccctgcag   2640
tatcagcacg agagaagggc tagcgactgg gccgtggact ccaatctgtg cggcgccatg   2700
gatccctccg atggaatcgg cgccctgatc gaagaggaac ggaccgccgt gaagctgaac   2760
acaggactgg ccctgcactg ccagcagttc tgggccatgt tcctgaagaa agccgcctac   2820
agctggcgcg agtggaaaat ggtggccgca caggtgctgg tgcccctgac ctgtgtgaca   2880
ctggcactgc tggccatcaa ctacagcagc gagctgttcg acgaccccat gctgagactg   2940
acactgggcg agtacggcag gaccgtggtg cctttttctg tgcccggcac ctcacagctg   3000
ggccagcagc tgtctgaaca cctgaaggat gccctgcagg ccgaaggcca ggaacccaga   3060
gaagtgctgg gcgatctgga agagttcctg atcttccggg ccagcgtgga aggcggcgga   3120
ttcaacgaga gatgcctggt ggctgcctcc ttccgggatg tgggcgagag aacagtcgtg   3180
aacgccctgt tcaacaatca ggcctaccac agccccgcca ccgctctggc tgtggtggac   3240
aacctgctgt ttaagctgct gtgtggcccc cacgcctcca tcgtggtgtc caatttcccc   3300
cagcccagaa gcgctctgca ggctgccaag gaccagttca acgagggccg gaagggcttc   3360
gacattgctc tgaatctgct gtttgccatg gcctttctgg cctccacctt cagcatcctg   3420
gctgtgtccg agagagccgt gcaggccaag cacgtgcagt ttgtgtctgg cgtgcacgtg   3480
gccagctttt ggctgtctgc cctgctgtgg gacctgatca gcttcctgat ccccagcctc   3540
ctgctgctgg tggtgttcaa ggccttcgac gtgcgggcct tcaccaggga tggacacatg   3600
gccgacacct tgttgttgct gctgctgtac ggctgggcca tcatccccct gatgtacctg   3660
atgaacttct tcttcctggg cgctgccacc gcctacacca gactgaccat cttcaacatc   3720
ctgagcggga tcgccacctt cctgatggtc acaatcatgc ggatccctgc cgtgaaactg   3780
gaagaactga gcaagaccct ggaccatgtg tttctggtgc tgcccaacca ctgcctgggc   3840
atggccgtgt ctagcttcta cgagaactac gagacacggc ggtactgcac ctccagcgaa   3900
gtggccgccc actactgcaa gaagtataac atccagtatc aggaaaactt ctacgcttgg   3960
agcgcacccg gcgtgggcag atttgtggcc tctatggccg ccagcggctg cgcctatctg   4020
atcctgctgt tcctgatcga gactaacctg ctgcagagac tgagaggcat cctgtgcgcc   4080
ctgcggcgga gaagaacact gaccgagctg tacacccgga tgcccgtgct gcctgaggac   4140
caggatgtgg ccgacgagcg gacaagaatc ctggccccta gccccgatag cctgctgcac   4200
acccccctga tcatcaaaga actgtccaag gtgtacgagc agcgggtgcc actgctggct   4260
gtggacagac tgagtctggc tgtgcagaaa ggcgagtgct tcggactgct gggcttcaac   4320
```

```
ggcgcaggca agaccacaac cttcaagatg ctgacaggcg aggaaagcct gacctccggc    4380

gacgcctttg tgggcggaca caggatctct tccgatgtgg gcaaagtgcg gcagcggatc    4440

ggctactgcc ctcagttcga cgccctgctg gatcacatga ccggcaggga aatgctcgtg    4500

atgtacgccc ggctgagggg catccccgag agacacattg gcgcctgcgt ggaaaacacc    4560

ctgcggggcc tgctgctgga accccacgct aacaaactcg tgcggaccta cagcggcggc    4620

aacaagagaa agctgtctac cggcattgca ctgatcggcg agccagccgt gatctttctg    4680

gatgagccca gcacaggcat ggaccccgtg gctcggagac tgctgtggga tacagtggcc    4740

agagccagag agtccggcaa ggccatcatt atcaccagcc acagcatgga agagtgcgag    4800

gccctgtgta caagactggc aattatggtg cagggacagt tcaagtgtct gggcagccct    4860

cagcacctga agtccaagtt cggctccggc tacagcctgc gggccaaggt gcagtctgaa    4920

gggcagcagg aagccctgga agagttcaaa gccttcgtgg acctgacctt ccccggctct    4980

gtgctggaag atgagcacca gggaatggtg cactaccatc tgcctggcag ggacctgtcc    5040

tgggccaaag tgtttggcat cctggaaaag gccaaagaga agtacggcgt ggacgattac    5100

agcgtgtccc agatcagcct ggaacaggtg ttcctgtcct ttgcccatct gcagccccct    5160

accgccgaag agggaaga                                                  5178
```

ATP-BINDING CASSETTE FAMILY CODING POLYRIBONUCLEOTIDES AND FORMULATIONS THEREOF

RELATED APPLICATIONS

This application is a national stage filing under 35 U.S.C. 371 of International Application No. PCT/EP2016/065321, filed Jun. 30, 2016, which claims the benefit of European Application No. 15174677.3, filed Jun. 30, 2015, the entire teachings of which are incorporated herein by reference. International Application No.: PCT/EP2016/065321 was published under PCT Article 21(2) in English.

BACKGROUND

Messenger RNAs (mRNA) are polymers containing a number of linked nucleotides, each composed of a sugar, a phosphate, and a base. Each mRNA polymer stores genetic information along the nucleotide chain. Messenger RNA polymers carry the genetic information from the DNA in the nucleus of the cell to the cytoplasm where proteins are made. Each triplet of nucleotides in the mRNA is called a codon, and each codon specifies the identity of an amino acid in the translated protein.

A cell can also take up and translate an exogenous RNA, but many factors influence efficient uptake and translation. For instance, the immune system recognizes many exogenous RNAs as foreign and triggers a response that is aimed at inactivating the RNAs. In addition, many exogenous RNAs are not sufficiently stable to be adequately expressed within a host cell.

SUMMARY

The present disclosure provides a composition comprising a modified polyribonucleotide for treating a subject having or suspected of having a disease associated with a gene of the ATP-binding cassette (ABC) family, such as ABCA3 that may be associated with a respiratory distress syndrome. The modified polyribonucleotide can include a codon sequence that is optimized for translation within cells of the subject exposed to the modified polyribonucleotide, wherein upon translation the modified polyribonucleotide yields a polypeptide that ameliorates a symptom of the disease. The gene in the ATP-binding cassette family can be selected from the group consisting of ABCA1, ABCA3, ABCA4, ABCA12, ABCB4, ABCB7, ABCB11, ABCC2, ABCC6, ABCC8, ABCC9, ABCD1, ABCG5, ABCG8, and CFTR. In some cases, the gene in the ATP-binding cassette family is ABCA3 or at least 70% homologous to the human ABCA3. In some cases, the composition comprises a ratio of moles of amine groups of cationic polymers to moles of phosphate groups of the modified polyribonucleotide of at least about 8. In some cases, the composition is selected from TABLE 8. In some cases, the optimized codon sequence is translated at least 20% more effectively within a cell of a subject than a non-optimized codon sequence. In some cases, the modified polyribonucleotide comprises a combination of unmodified and modified nucleotides. A composition of the disclosure can be used to treat a disease, and the disease can be selected from the group consisting of age-related macular degeneration, benign recurrent intrahepatic cholestasis, Cantu syndrome, congenital bilateral absence of the vas deferens, congenital hyperinsulinism, cystic fibrosis, Dubin-Johnson syndrome, familial dilated cardiomyopathy, familial HDL deficiency, generalized arterial calcification of infancy, harlequin ichthyosis, hereditary pancreatitis, intrahepatic cholestasis of pregnancy, lamellar ichthyosis, permanent neonatal diabetes mellitus, progressive familial intrahepatic cholestasis, pseudoxanthoma elasticum, retinitis pigmentosa, sitosterolemia, Stargardt macular degeneration, surfactant dysfunction, Tangier disease, X-linked adrenoleukodystrophy, X-linked sideroblastic anemia and ataxia. In some cases, the modified polyribonucleotide provides expression of the polypeptide for a time period in the cell of the subject having the modified polyribonucleotide, wherein the time period is up to 4 weeks, wherein the expression is enhanced as compared to expression in a control cell that has been exposed to an unmodified polyribonucleotide encoding the polypeptide. The time period can be of at least about 30 seconds and up to 5 days. In some cases, the modified polyribonucleotide comprises a 3' or 5' noncoding region flanking the codon sequence which encodes the polypeptide, wherein the noncoding region aids in enhanced expression of the polypeptide in the cells. In some cases, the modified polyribonucleotide is formulated in a nanoparticle, nanocapsule, cationic lipid, cationic polymer, nanoemulsion. In some cases the modified polyribonucleotide comprises analogues of uridine or analogues of cytidine. In some cases, the modified polyribonucleotide comprises 5% to 50% analogues of uridine or 5% to 50% analogues of cytidine. In some cases, the modified polyribonucleotide comprises 15% to 30% analogues of uridine or 15% to 30% analogues of cytidine. In some cases the analogues of uridine are selected from the group consisting of pseudouridine, 2-thiouridine, 5-iodouridine, and 5-methyluridine. In some cases the analogues of cytidine are selected from the group consisting of 5-methylcytidine, 2'-amino-2'-deoxycytidine, 2'-fluoro-2'-deoxycytidine, and 5-iodocytidine. In some cases, the modified polyribonucleotide comprises 5-methylcytidine or pseudouridine. In some cases, the modified polyribonucleotide comprises (i) uridine and cytidine; and (ii) analogues of the uridine and cytidine. In some cases the modified polyribonucleotide comprises analogues of adenosine or analogues of guanosine. In some cases, the modified polyribonucleotide comprises (i) adenosine or guanosine; and (ii) analogues of the adenosine or guanosine. In some cases, the modified polyribonucleotide comprises less than 50% analogues of adenosine or guanosine. In some cases, the modified polyribonucleotide comprises (i) adenosine and guanosine; and (ii) analogues of the adenosine and guanosine. In some cases, the modified polyribonucleotide has a transfection efficiency greater than 80% among cells exposed to the modified polyribonucleotide. In some cases, the modified polyribonucleotide induces substantially no change in a level of at least one inflammatory marker expressed by peripheral blood mononuclear cells exposed to the modified polyribonucleotide. In some cases (i) the codon sequence is a gene or fragment whose defect or deficiency is associated with a presence of the disease, or (ii) a lack or deficiency of the polypeptide is associated with the presence of the disease. For example, a deficiency in the ABCA3 gene can be a cause of respiratory distress syndrome. In some cases, the modified polyribonucleotide lowers an immune response of the subject as compared to an unmodified polyribonucleotide encoding the polypeptide, which immune response is as determined by a level of at least one inflammatory marker selected from TNF-α, IL-2 and IL-8 expressed by peripheral blood mononuclear cells exposed to the modified polyribonucleotide as compared to a level of the at least one inflammatory marker in peripheral blood mononuclear cells in a control that has been exposed to the unmodified polyribonucleotide.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
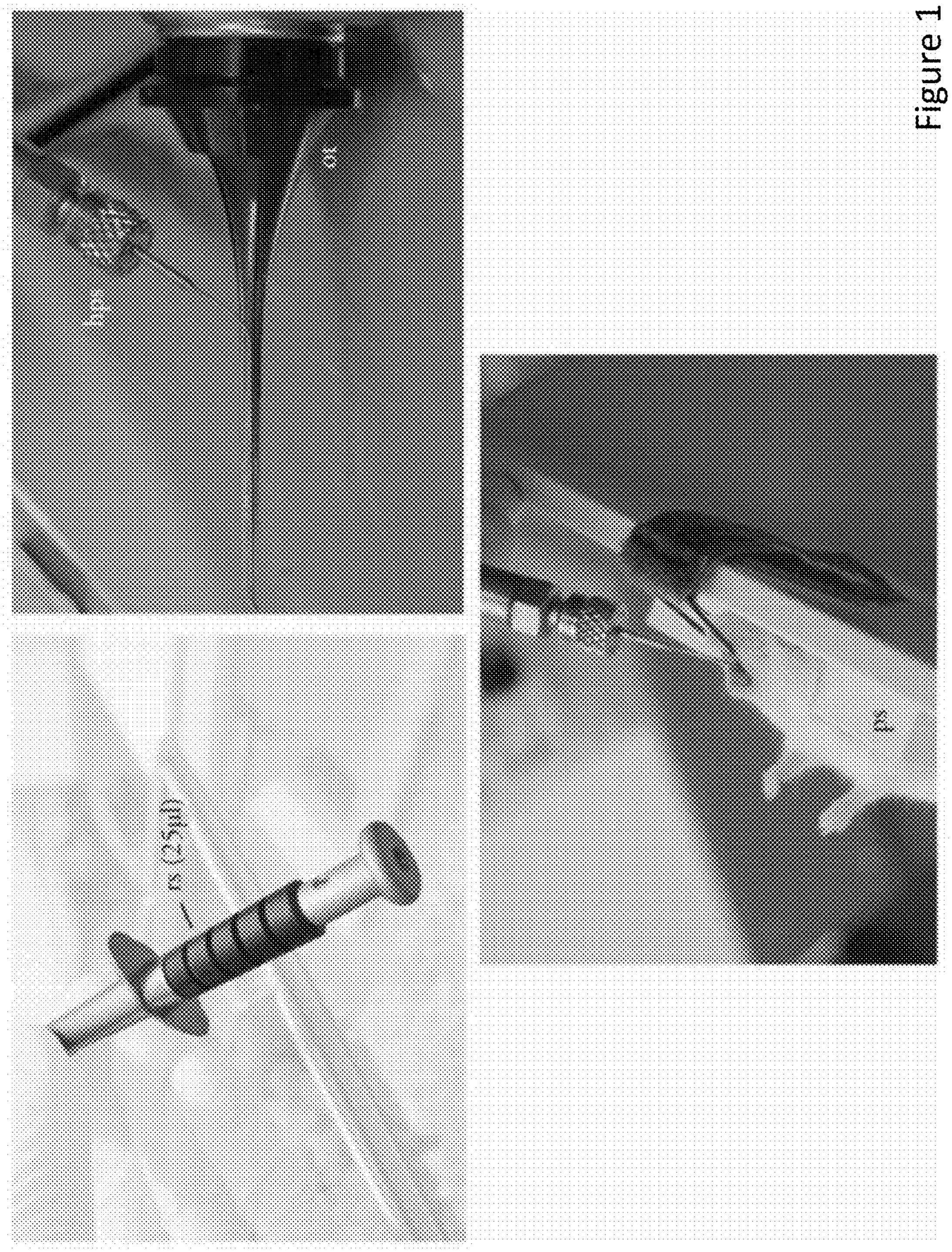
FIG. 1 illustrates an example of aerosol administration of engineered polyribonucleotides of the disclosure to mice.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein generally refers to a human. In some instances, a subject can also be an animal, such as a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

The term "disease," as used herein, generally refers to an abnormal physiological condition that affects part or all of a subject, such as an illness (e.g., asthma) or a cancer.

The term "cancer," as used herein, generally refers to any growth resulting from the abnormal division of cells. A cancer can be a malignant or benign growth or tumor resulting from the division of abnormal cells. A cancer can be a hematologic cancer or a cancer can be a solid cancer. A cancer can be disease can be a benign or a malignant uncontrolled division of abnormal cells in any part of the body of a subject. Non-limiting examples of cancers encompassed include breast cancer and lung cancer. Examples of lung cancers are non-small cell lung cancer, small cell lung cancer, and lung carcinoid tumor. Examples of breast cancers include metastatic breast cancer, inflammatory breast cancer, triple negative breast cancer (negative for progesterone, estrogen, and HER2/neu receptors), invasive ductal carcinoma, and ductal carcinoma in situ.

The term "polynucleotide" or "nucleic acid" as used herein refers to a polymeric form of nucleotides of any length, either ribonucleotides or deoxyribonucleotides, that comprise purine and pyrimidine bases, chemically or biochemically modified, natural or non-natural, or derivatized nucleotide bases. In some embodiments, a polynucleotide comprises purine and/or pyrimidine analogues. Polynucleotides include sequences of deoxyribonucleic acid (DNA), ribonucleic acid (RNA), or DNA copies of ribonucleic acid (cDNA), all of which can be recombinantly produced, artificially synthesized, or isolated and purified from natural sources. The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, including naturally occurring or non-naturally occurring nucleotides, such as methylated nucleotides and nucleotide analogues (or analogs). The sequence of nucleotides may be interrupted by non-nucleotide components.

The term "polyribonucleotide," as used herein, generally refers to polynucleotide polymers that contain greater than 50% of ribose bases, including unmodified and/or modified ribonucleotides. The term also refers to polynucleotide polymers that comprise ribonucleic acids, such as that contain greater than 50% of ribose bases, including unmodified and/or modified ribonucleotides. The term also refers to polynucleotide polymers that comprise chemically modified ribonucleotides, such as analogues. A polyribonucleotide can be formed of D-ribose, which can be found in nature, and L-ribose, which are not found in nature.

The term "polypeptides," as used herein, generally refers to polymer chains comprised of amino acid residue monomers which are joined together through amide bonds (peptide bonds). The amino acids may be the L-optical isomer or the D-optical isomer. A polypeptide can be a chain of at least three amino acids, peptide-mimetics, a protein, a recombinant protein, an antibody (monoclonal or polyclonal), an antibody fragment, a single-chain variable fragment (scFv), an antigen, an epitope, an enzyme, a receptor, a vitamin, or a structure analogue or combinations thereof. As used herein, the abbreviations for the L-enantiomeric and D-enantiomeric amino acids that form a polypeptide are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). X or Xaa can indicate any amino acid.

The term "engineered," as used herein, generally refers to non-naturally occurring, genetically modified polynucleotides, vectors, and nucleic acid constructs that have been genetically designed and manipulated to provide a polynucleotide intracellularly. In some embodiments, engineered refers to polynucleotides, vectors, and nucleic acid constructs that have been genetically designed and manipulated to provide a polynucleotide intracellularly. An engineered polynucleotide can be partially or fully synthesized in vitro. An engineered polynucleotide can also be cloned. An engineered polyribonucleotide can contain one or more modified bases or base or sugar analogues, such as ribonucleotides not naturally-found in messenger RNAs. An engineered polyribonucleotide can contain modified nucleotides or nucleotide analogues that exist in transfer RNAs (tRNAs), ribosomal RNAs (rRNAs), guide RNAs (gRNAs), small nuclear RNA (snRNA), small nucleolar RNA (snoRNA), SmY RNA, spliced leader RNA (SL RNA), CRISPR RNA, long non-coding RNA (lncRNA), microRNA (miRNA), or another suitable RNA.

Overview

The present disclosure provides compositions and methods for the treatment of conditions with stable nucleic acids encoding a protein or protein fragment(s). The present disclosure also provides methods for delivering a polyribonucleotide that can be translated within a cell involved in surfactant production to a subject. For instance, the ABCA3 gene provides instructions for making a protein involved in surfactant production. Surfactant can be a mixture of certain fats (called phospholipids) and proteins that lines the lung tissue and facilitates expansion and contraction of the lungs and breathing of a subject. Without normal surfactant, the tissue surrounding the air sacs in the lungs (the alveoli) sticks together after exhalation (because of a force called surface tension), causing the alveoli to collapse. As a result, filling the lungs with air on each breath can be difficult, and delivery of oxygen to the body can be impaired. This can lead to respiratory distress syndrome in subjects, such as infants.

The ABCA3 protein is typically found in the membrane that surrounds lamellar bodies, which are the cellular structures in which the phospholipids and proteins that make up surfactant are packaged. The ABCA3 protein can transport phospholipids into the lamellar bodies where they interact with surfactant proteins to form surfactant. The ABCA3 protein also appears to be involved in the formation of normal lamellar bodies. In addition to packaging, lamellar bodies can be important for the correct processing of surfactant proteins, which is necessary for the proteins to mature and become functional. An engineered polyribonucleotide of the disclosure can be delivered and translated within a cell of a subject to yield an ABCA3 protein, a functional fragment thereof, or a functional homolog to treat a condition that is associated with, for instance, a defect in surfactant production.

In some instances, the engineered polyribonucleotide comprises the genetic code of 5' untranslated regions (UTRs) and 3' UTRS shown in Table 1:

TABLE 1

| UTRs | |
|---|---|
| UTR | DNA sequence (from 5' to 3') |
| CYBA 5' | CGCGCCTAGCAGTGTCCCAGCCGGGTTCGTGTCGCC (SEQ ID NO: 1) |
| CYBA 3' | CCTCGCCCCGGACCTGCCCTCCCGCCAGGTGCACCCACCTGCAATAAATG CAGCGAAGCCGGGA (SEQ ID NO: 2) |
| α-globin 5' UTR (HBA1) | CATAAACCCTGGCGCGCTCGCGGCCCGGCACTCTTCTGGTCCCCACAGAC TCAGAGAGAACCCACC (SEQ ID NO: 3) |
| α-globin 5' UTR (HBA2) | CATAAACCCTGGCGCGCTCGCGGGCCGGCACTCTTCTGGTCCCCACAGAC TCAGAGAGAACCCACC (SEQ ID NO: 4) |
| α-globin 5' UTR ETH | TCTTCTGGTCCCCACAGACTCAGAGAGAAC (SEQ ID NO: 5) |
| ABCA3 5' | GCGGCCGCTGCGTCCGCCAGTAGCGGGTTGCAGGCGCACCCTCCCCTCCA GGGCGGCCACGCAGCTGTCAGTGCCGCCGCCACTGCGAGGCTGGAGCGGA GCCCGGGTGGCCGAGGGAGGGGACCCCGCGAGAGGGCCGCGCGCCGGCC GCCGCCGCCCCGGCGCCCAGGCTCGGTGCTGGAGAGTCATGCCTGTGAGC CCTGGGCACCTCCTGATGTCCTGCGAGGTCACGGTGTTCCCAAACCTCAGG GTTGCCCTGCCCCACTCCAGAGGCTCTCAGGCCCCACCCCGGAGCCCTCTG TGCGGAGCCGCCTCCTCCTGGCCAGTTCCCCAGTAGTCCTGAAGGGAGAC |

TABLE 1-continued

| UTRs | |
|---|---|
| UTR | DNA sequence (from 5' to 3') |
| | CTGCTGTGTGGAGCCTCTTCTGGGACCCAGCCATGAGTGTGGAGCTGAGC AACTGAACCTGAAACTCTTCCACTGTGAGTCAAGGAGGCTTTTCCGCACAT GAAGGACGCTGAGCGGGAAGGACTCCTCTCTGCCTGCAGTTGTAGCGAGT GGACCAGCACCAGGGGCTCTCTAGACTGCCCCTCCTCCATCGCCTTCCCTG CCTCTCCAGGACAGAGCAGCCACGTCTGCACACCTCGCCCTCTTTACACTC AGTTTTCAGAGCACGTTTCTCCTATTTCCTGCGGGTTGCAGCGCCTACTTG AACTTACTCAGACCACCTACTTCTCTAGCAGCACTGGGCGTCCCTTTCAGC AAGACG (SEQ ID NO: 6) |
| ABCA3 3' | GGGGTGGCGGCTGTCTCGCCATCAGGCAGGGACAGGACGGGCAAGCAGG GCCCATCTTACATCCTCTCTCTCCAAGTTTATCTCATCCTTTATTTTTAATC ACTTTTTTCTATGATGGATATGAAAAATTCAAGGCAGTATGCACAGAATGG ACGAGTGCAGCCCAGCCCTCATGCCCAGGATCAGCATGCGCATCTCCATG TCTGCATACTCTGGAGTTCACTTTCCCAGAGCTGGGGCAGGCCGGGCAGTC TGCGGGCAAGCTCCGGGGTCTCTGGGTGGAGAGCTGACCCAGGAAGGGCT GCAGCTGAGCTGGGGGTTGAATTTCTCCAGGCACTCCCTGGAGAGAGGAC CCAGTGACTTGTCCAAGTTTACACACGACACTAATCTCCCCTGGGGAGGA AGCGGGAAGCCAGCCAGGTTGAACTGTAGCGAGGCCCCCAGGCCGCCAG GAATGGACCATGCAGATCACTGTCAGTGGAGGGAAGCTGCTGACTGTGAT TAGGTGCTGGGGTCTTAGCGTCCAGCGCAGCCCGGGGGCATCCTGGAGGC TCTGCTCCTTAGGGCATGGTAGTCACCGCGAAGCCGGGCACCGTCCCACA GCATCTCCTAGAAGCAGCCGGCACAGGAGGGAAGGTGGCCAGGCTCGAA GCAGTCTCTGTTTCCAGCACTGCACCCTCAGGAAGTCGCCCGCCCCAGGAC ACGCAGGGACCACCCTAAGGGCTGGGTGGCTGTCTCAAGGACACATTGAA TACGTTGTGACCATCCAGAAAATAAATGCTGAGGGGACACAGTC (SEQ ID NO: 7) |

The engineered polynucleotide can comprise the mRNA sequence of ABCA3 gene (SEQ ID NO: 8), the DNA sequence of ABCA3 (SEQ ID NO: 9), a native ABCA3 DNA sequence with a 5' CYBA UTR and a 3' CYBA UTR (SEQ ID NO: 10), a native ABCA3 mRNA sequence with a 5' CYBA UTR and a 3' CYBA UTR (SEQ ID NO: 11), a codon optimized ABCA3 DNA sequence with a 5' CYBA UTR and a 3' CYBA UTR (SEQ ID NO: 12), or a codon optimized ABCA3 mRNA sequence with a 5' CYBA UTR and a 3' CYBA UTR (SEQ ID NO: 13).

In some cases the engineered polyribonucleotide comprises at least a portion of the sequence of a gene in the ATP-binding cassette (ABC) family. The gene in the ATP-binding cassette family can be ABCA1, ABCA3, ABCA4, ABCA12, ABCB4, ABCB7, ABCB11, ABCC2, ABCC6, ABCC8, ABCC9, ABCD1, ABCG5, ABCG8, or CFTR. The engineered polyribonucleotide can comprise a sequence that is at least 10%, at least 20%, at least 30%, at least 40%, at least 50%, at least 60%, at least 70%, at least 80%, at least 90%, or at least 95% homologous to a sequence of a gene in the ATP-binding cassette (ABC) family.

Engineered Polynucleotides

The present disclosure provides nucleic acid molecules, such as polynucleotides, which encode one or more polypeptides of interest. The term nucleic acid includes any compound and/or substance that comprise a polymer of nucleotides. Nucleotide polymers that contain greater than 50% of ribose bases or modified ribonucleotides or ribonucleotide analogues are referred to as polyribonucleotides. The sequence of the engineered polynucleotides can be derived from, for example, DNA, RNA, mRNA transcripts, genomic DNA, mitochondrial DNA, mitochondrial RNA, or another suitable nucleic acid that comprises the genetic information of a gene of interest. The nucleic acid constructs, vectors, engineered polynucleotides or polyribonucleotides, or compositions can be derived from nucleic acids carrying mutated genes and polymorphisms.

In addition to the four classical/canonical ribonucleotides, namely, adenosine, guanosine, cytidine and uridine, several cellular RNAs also contain a number of structurally diverse ribonucleotides. About a hundred structurally different nucleotides, modified nucleotides, or nucleotide analogues have been identified in transfer RNAs (tRNAs), ribosomal RNAs (rRNAs), messenger RNAs (mRNAs) and small nuclear RNAs (snRNAs). In tRNAs, some nucleotides or modified nucleotides can be important determinants of the specificity and efficiency of aminoacylation and codon recognition. Such structurally diverse ribonucleotides can be a modified ribonucleotide or a nucleotide analogue. In some cases a polynucleotide of the disclosure is engineered to comprise a modified ribonucleotide or ribonucleotide analogue.

Exemplary nucleic acids that can form a polynucleotide of the disclosure include, but are not limited to, ribonucleic acids (RNAs), deoxyribonucleic acids (DNAs), or hybrids thereof. Exemplary modified nucleotides that can form at least a fraction of a polynucleotide of the disclosure include, but are not limited to, pseudouridine ($\Psi$), 5-iodouridine ($I^5U$), 5-iodocytidine ($I^5C$), 2-thiouridine ($s^2U$), 5-methylcytidine ($m^5C$).

A modification, such as a chemical modification, can be located on one or more nucleoside(s) or the backbone of the nucleic acid molecule. They can be located on both a nucleoside and a backbone linkage. A modification can be engineered into a polynucleotide in vitro. Modified ribonucleotides and nucleic acid analogues can also be synthesized post-transcriptionally by covalent modification of the classical ribonucleotides.

An engineered polyribonucletide of the disclosure can comprise modified purines and pyrimidines or purine and pyrimidine analogues. In some cases, a polyribonucleotide of the disclosure comprises a modified pyrimidine, such as a modified uridine and/or a modified cytidine. In some cases a modified uridine or uridine analogue is selected from pseudouridine ($\Psi$), 2-thiouridine ($s^2U$), 5-methyluridine ($m^5U$), 5-methyluridine ($m^5U$), 5-iodouridine ($I^5U$), 4-thiouridine ($s^4U$), 5-bromouridine ($Br^5U$), 2'O-methyluridine (U2'm), 2'-amino-2'-deoxyuridine (U2'$NH_2$), 2'-azido-2'-deoxyuridine (U2'$N_3$), and 2'-fluoro-2'-deoxyuridine (U2'F). In some cases, a modified cytidine is selected from 5-methylcytidine ($m^5C$), 3-methylcytidine ($m^3C$), 2-thiocytidine ($s^2C$), 2'-O-methylcytidine+(C2'm), 2'-amino-2'-deoxycytidine (C2'$NH_2$), 2 '-fluoro-2'-deoxycytidine (C2'F), 5-iodocytidine ($I^5C$), 5-bromocytidine 5'-triphosphate ($Br^5C$) and 2 '-azido-2'-deoxycytidine 5'-triphosphate (C2'$N_3$). Note that when referring to analogs, the foregoing (or the analogs listed in the tables below) also refers to analogs in their 5' triphosphate form.

In some instances the engineered polyribonucleotide comprises at least one modified ribonucleotide. In some cases, the modified ribonucleotide is at least 25% more stable in the subject as compared to a non-modified (or unmodified) ribonucleotide. In some cases, the modified nucleotide can be at least 30% more stable, at least 35% more stable, at least 40% more stable, at least 45% more stable, at least 50% more stable, at least 55% more stable, at least 60% more stable, at least 65% more stable, at least 70% more stable, at least 75% more stable, at least 80% more stable, at least 85% more stable, at least 90% more stable, or at least 95% more stable in the subject as compared to a non-modified ribonucleotide.

A polyribonucleotide can have nucleotides that have been modified in the same form or else a mixture of different modified nucleotides. The modified nucleotides can have modifications that are naturally or not naturally occurring in messenger RNA. A mixture of various modified nucleotides can be used. For example one or more modified nucleotides within a polynucleotide can have natural modifications, while another part has modifications that are not naturally found in mRNA. In some cases, the stability of the RNA can be selectively optimized by changing the nature of modified bases within the modified polyribonucleotide.

Non-limiting examples of uridine modifications that have an effect on the stability or immunogenicity of the polynucleotide are shown in TABLE 2.

TABLE 2

| Name | Base modification | Sugar modification (2' position) | Naturally occurring in mRNA |
|---|---|---|---|
| Pseudouridine | — | | Yes |
| 5-methyluridine ($m^5U$) | $CH_3$ | | No |
| 5-iodouridine ($I^5U$) | I | | No |
| 5-bromouridine ($Br^5U$) | Br | | No |
| 2-thiouridine ($s^2U$) | S (in 2 position) | | No |
| 4-thiouridine ($s^4U$) | S (in 4 position) | | No |
| 2'-O-methyluridine (U2'm) | — | $CH_3$ | Yes |
| 2'-amino-2'-deoxyuridine (U2'$NH_2$) | — | $NH_2$ | No |
| 2'-azido-2'-deoxyuridine (U2'$N_3$) | — | $N_3$ | No |
| 2'-fluoro-2'-deoxyuridine (U2'F) | — | F | No |

Non-limiting examples of cytidine modifications that have an effect on the stability or immunogenicity of the polynucleotide are shown in TABLE 3.

TABLE 3

| Name | Base modification | Sugar modification (2' position) | Naturally occurring in mRNA |
|---|---|---|---|
| 5-methylcytidine ($m^5C$) | $CH_3$ | | yes |
| 5-iodocytidine ($I^5C$) | I | | no |
| 5-bromocytidine ($Br^5C$) | Br | | no |
| 2-thiocytidine ($s^2C$) | S (in 2 position) | | no |
| 2'-O-methylcytidine (C2'm) | — | $CH_3$ | yes |
| 2'-amino-2'-deoxycytidine (C2'$NH_2$) | — | $NH_2$ | no |
| 2'-azido-2'-deoxycytidine (C2'$N_3$) | — | $N_3$ | no |
| 2'-fluoro-2'-deoxycytidine (C2'F) | — | F | no |

Non-limiting examples of adenosine modifications that have an effect on the stability or immunogenicity of the polynucleotide are shown in TABLE 4.

TABLE 4

| Name | Base modification | Sugar modification (2' position) | Naturally occurring in mRNA |
|---|---|---|---|
| N6-methyladenosine ($m^6A$) | $CH_3$ (in 6 position) | | Yes |
| N1-methyladenosine ($m^1A$) | $CH_3$ (in 1 position) | | No |
| 2'-O-methyladenosine (A2'm) | — | $CH_3$ | Yes |
| 2'-amino-2'-deoxyadenosine (A2'$NH_2$) | — | $NH_2$ | No |
| 2'-azido-2'-deoxyadenosine (A2'$N_3$) | — | $N_3$ | No |
| 2'-fluoro-2'-deoxyadenosine (A2'F) | — | F | No |

Non-limiting examples of guanosine modifications that have an effect on the stability or immunogenicity of the polynucleotide are shown in TABLE 5.

TABLE 5

| Name | Base modification (5'-position) | Sugar modification (2' position) | Naturally occurring in mRNA |
|---|---|---|---|
| N1-methylguanosine ($m^1G$) | $CH_3$ (in position 1) | | No |
| 2'-O-methylguanosine (G2'm) | — | $CH_3$ | Yes |
| 2'-amino-2'-deoxyguanosine (G2'$NH_2$) | — | $NH_2$ | No |
| 2'-azido-2'-deoxyguanosine (G2'$N_3$) | — | $N_3$ | No |
| 2'-fluoro-2'-deoxyguanosine (G2'F) | — | F | No |

A modified nucleotide can be selected from the group comprising pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thiodihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methylinosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine. 1461 In some cases, at least about 5% of the engineered polyribonucleotide includes non-naturally occurring (e.g., modified or engineered) uracil, adenine, guanine, or cytosine, such as the modified nucleotides described herein. In some cases, at least about 10%, 15%, 20%, 25%, 30%, 40%, 45%, 50%, 55%, 60%, 65%, 70%, 75%, 80%, 85%, 90%, 95% of the engineered polyribonucleotide includes non-naturally occurring uracil, adenine, guanine, or cytosine. In some cases, at most about 99%, 95%, 90%, 85%, 80%, 75%, 70%, 65%, 60%, 55%, 50%, 45%, 40%, 35%, 30%, 25%, 20%, 15%, 10%, 5%, 1%, of the engineered polyribonucleotide includes non-naturally occurring uracil, adenine, guanine, or cytosine.

An engineered polyribonucleotide of the disclosure can comprise one or more promoter sequences and any associated regulatory sequences. A promoter sequence and/or an associated regulatory sequence can comprise any number of modified or unmodified nucleotides. Promoter sequences and/or any associated regulatory sequences can comprise, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or at least 10000 bases or base pairs. A promoter sequence and/or an associated regulatory sequence can comprise any number of modified or unmodified nucleotides, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs.

In some cases, less than all of the nucleotides in the promoter sequence or associated regulatory region are modified. For instance, in some cases, less than or equal to 99%, 95%, 90%, 85%, 80%, 75%, 70%, 65%, 60%, 55%, 50%, 45%, 40%, 35%, 30%, 25%, 20%, 15%, 10%, or 5% of the nucleotides in a promoter or associated regulatory region. In some cases, all of the nucleotides in a promoter or associated regulatory region are modified.

An engineered polyribonucleotide of the disclosure can comprise an engineered 5' cap, or a 5' Cap can be added to a polyribonucleotide intracellularly. The 5'cap structure of an mRNA can be involved in binding to the mRNA Cap Binding Protein (CBP), which is responsible for mRNA stability in the cell and translation competency through the association of CBP with poly(A) binding protein to form the mature cyclic mRNA species. The 5'cap structure can also be involved in nuclear export, increases in mRNA stability, and in assisting the removal of 5' proximal introns during mRNA splicing.

An engineered polyribonucleotide can be 5-end capped generating a 5-ppp-5'-triphosphate linkage between a terminal guanosine cap residue and the 5-terminal transcribed sense nucleotide of the mRNA molecule. The cap-structure can comprise a modified or unmodified 7-methylguanosine linked to the first nucleotide via a 5'-5' triphosphate bridge. This 5-guanylate cap can then be methylated to generate an N7-methyl-guanylate residue. The ribose sugars of the terminal and/or anteterminal transcribed nucleotides of the 5'end of the mRNA may optionally also be 2'-O-methylated. 5'-decapping through hydrolysis and cleavage of the guanylate cap structure may target a nucleic acid molecule, such as an mRNA molecule, for degradation.

In some cases, a cap can comprise further modifications, including the methylation of the 2' hydroxy-groups of the first 2 ribose sugars of the 5' end of the mRNA. For instance, an eukaryotic cap-1 has a methylated 2'-hydroxy group on the first ribose sugar, while a cap-2 has methylated 2'-hydroxy groups on the first two ribose sugars. Such double modification can provide significant resistance to 5' exonucleases. Non-limiting examples of 5' cap structures that can be used with an engineered polyribonucleotide include, but are not limited to, $m^7G(5')ppp(5')N$(Cap-0), $m^7G(5')ppp(5')$N1mpNp (Cap-1), and 7mG(5')-ppp(5')N1mpN2mp (Cap-2).

Modifications to the modified mRNA of the present disclosure may generate a non-hydrolyzable cap structure preventing decapping and thus increasing mRNA half-life. Because cap structure hydrolysis requires cleavage of 5'-ppp-5'phosphorodiester linkages, modified nucleotides may be used during the capping reaction. For example, a Vaccinia Capping Enzyme from New England Biolabs (Ipswich, Mass.) may be used with a-thio-guanosine nucleotides according to the manufacturer's instructions to create a phosphorothioate linkage in the 5'-ppp-5' cap. Additional modified guanosine nucleotides may be used such as a-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polyribonucleotide.

The modified mRNA may be capped post-transcriptionally, According to the present disclosure, 5' terminal caps may include endogenous caps or cap analogues. According to the present disclosure, a 5' terminal cap may comprise a guanine analogue. Useful guanine analogues include, but are not limited to, inosine, N1-methyl-guanosine, 2'fluoroguanosine, 7-deaza-guanosine, 8-oxo-guanosine, 2-amino-guanosine, LNA-guanosine, and 2-azido-guanosine.

Further, an engineered polyribonucleotide can contain one or more internal ribosome entry site(s) (IRES). IRES sequences can initiate protein synthesis in absence of the 5' cap structure. An IRES sequence can also be the sole ribosome binding site, or it can serve as one of multiple ribosome binding sites of an mRNA. Engineered polyribonucleotides containing more than one functional ribosome binding site can encode several peptides or polypeptides that are translated by the ribosomes ("polycistronic or multicistronic polynucleotides"). An engineered polynucleotide described here can comprise at least 1 IRES sequence, two IRES sequences, three IRES sequences, four IRES sequences, five IRES sequences, six IRES sequences, seven IRES sequences, eight IRES sequences, nine IRES sequences, ten IRES sequences, or another suitable number are present in an engineered polyribonucleotide. Examples of IRES sequences that can be used according to the present disclosure include without limitation, those from picornaviruses (e.g., FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV). An IRES sequence can be derived, for example, from commercially available vectors such as the IRES sequences available from Clontech™, GeneCopoeia™, Sigma-Aldrich™. IRES sequences can be, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or 10000 bases or base pairs. IRES sequences can at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 50 bases or base pairs, or 10 bases or base pairs.

An engineered polyribonucleotide of the disclosure can comprise one or more untranslated regions. An untranslated can comprise any number of modified or unmodified nucleotides. Untranslated regions (UTRs) of a gene are transcribed but not translated into a polypeptide. In some cases, an untranslated sequence can increase the stability of the nucleic acid molecule and the efficiency of translation. The regulatory features of a UTR can be incorporated into the modified mRNA molecules of the present disclosure, for instance, to increase the stability of the molecule. The specific features can also be incorporated to ensure controlled down-regulation of the transcript in case they are misdirected to undesired organs sites. Some 5' UTRs play roles in translation initiation. A 5' UTR can comprise a Kozak sequence which is involved in the process by which the ribosome initiates translation of many genes. Kozak sequences can have the consensus CCR(A/G)CCAUGG, where R is a purine (adenine or guanine) that is located three bases upstream of the start codon (AUG). 5' UTRs may form secondary structures which are involved in binding of translation elongation factor. In some cases, one can increase the stability and protein production of the engineered polynucleotide molecules of the disclosure, by engineering the features typically found in abundantly expressed genes of specific target organs. For example, introduction of 5'UTR of liver-expressed mRNA, such as albumin, serum amyloid A, Apolipoprotein A/B/E, transferrin, alpha fetoprotein, erythropoietin, or Factor VIII, can be used to increase expression of an engineered polynucleotide in a liver. Likewise, use of 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of an engineered polynucleotide in a desired cell or tissue. In some cases a UTR of the disclosure can be derived from the sequence of a cytochrome b-245 alpha polypeptide (CYBA), an α-globin gene, or a gene of the ATP-binding cassette (ABC) family, such as the ABCA3 gene.

Thus, in preferred embodiments, the composition comprising a modified polyribonucleotide of the present invention comprises one or more untranslated regions (UTR) derived from the sequence of a cytochrome b-245 alpha polypeptide (CYBA). In more preferred embodiments, the composition comprising a modified polyribonucleotide comprising one or more untranslated region (UTR) derived from the sequence of a cytochrome b-245 alpha polypeptide (CYBA) is a composition wherein the modified polyribonucleotide encodes a gene of the ABC-binding cassette (ABC) family as described herein above and below.

In the following, preferred embodiments of the untranslated region(s) (UTR) derived from the sequence of a cytochrome b-245 alpha polypeptide (CYBA) are described:

In the above Table 1, the DNA sequences displaying the human CYBA gene 5'- and 3' UTRs are shown as SEQ ID NO:1 and SEQ ID NO:2, respectively.

In view of the fact that the present invention predominantly relates to an RNA molecule (i.e., a modified polyribonucleotide molecule in terms of the present invention) reference is made in the following to the corresponding RNA sequences of said UTRs.

Derived from the above DNA sequence, SEQ ID NO:1 corresponds to the following UTR sequence on the RNA level:

(SEQ ID NO: 14)
5'-CGCGCCUAGCAGUGUCCCAGCCGGGUUCGUGUCGCC-3'.

This 5'UTR sequence immediately precedes the start codon of the human CYBA gene.

Derived from the above DNA sequence, SEQ ID NO:2 corresponds to the following UTR sequence on the RNA level:

(SEQ ID NO: 15))
5'-CCUCGCCCCGGACCUGCCCUCCCGCCAGGUGCACCC

ACCUGCAAUAAAUGCAGCGAAGCCGGGA-3'.

SEQ ID NO: 5 corresponds, on the RNA level to the sequence set forth in SEQ ID NO: 16.

The term "untranslated region" or "UTR" as used in accordance with the present invention relates sections of the mRNA upstream the start codon and downstream the stop codon that are not translated, and are, therefore, termed the five prime untranslated region (5' UTR) and three prime untranslated region (3' UTR), respectively. These regions are transcribed with the coding region and thus are exonic as they are present in the mature mRNA.

As used in the present invention, the 3' untranslated region (3'-UTR) relates to the section of messenger RNA (mRNA) that immediately follows the translation termination codon. An mRNA molecule is transcribed from the DNA sequence and is later translated into protein. Several regions of the mRNA molecule are not translated into protein including the 5' cap, 5' UTR, 3' UTR, and the poly-A tail.

As used in the present invention, the 5' untranslated region (5' UTR) (also known as a Leader Sequence or Leader RNA) is the region of an mRNA that is directly upstream from the start codon. The 5' UTR begins at the transcription start site and ends one nucleotide (nt) before the start codon (usually AUG) of the coding region. In prokaryotes, the length of the 5' UTR tends to be 3-10 nucleotides long while in eukaryotes it tends to be, longer, generally from 100 to several thousand nucleotides long but sometimes also shorter UTRs occur in eukaryotes.

As used in the present invention, the 3' UTR may comprise regulatory regions within the 3'-untranslated region which are known to influence polyadenylation and stability of the mRNA. Many 3'-UTRs also contain AU-rich elements (AREs). Furthermore, the 3'-UTR contains the sequence AAUAAA that directs addition of several hundred adenine residues called the poly(A) tail to the end of the mRNA transcript.

Thus, an RNA molecule as used in accordance with the present invention may also contain a poly-A tail. A poly-A tail is a long sequence of adenine nucleotides (often several hundred) added to the 3' end of the pre-mRNA by a process called polyadenylation. This tail promotes export from the nucleus and translation, and protects the mRNA from degradation. Polyadenylation is the addition of a poly(A) tail to a messenger RNA. The poly(A) tail consists of multiple adenosine monophosphates; in other words, it is a stretch of RNA that has only adenine bases. In eukaryotes, polyadenylation is part of the process that produces mature messenger RNA (mRNA) for translation. As used herein, a poly-A tail relates to a sequence of adenine nucleotides located at the 3' end of the RNA. A poly-A tail is commonly added to the 3' end of the RNA by a process called polyadenylation. Thus, the present invention relates to any of the above-described RNA, wherein the RNA molecule comprises a poly-A tail at the 3' end.

The length of the poly-A tail is not particularly limited. Yet, in preferred embodiments, the RNA molecule of the present invention comprises a poly-A tail at the 3' end wherein the poly-A tail has a length of at least 50, 60, 70, 80, 90, 100 or 110 nucleotides. In a more preferred embodiment, the RNA molecule of the present invention comprises a poly-A tail at the 3' end wherein the poly-A tail has a length of at least 120 nucleotides. In other preferred embodiments, the RNA molecule of the present invention comprises a poly-A tail at the 3' end wherein the poly-A tail has a length of at least 150, 200, 250, 300, 350, 400, 500, 600, 700, 800, 900 or 1000 nucleotides.

In a preferred embodiment, the composition comprising a modified polyribonucleotide/RNA molecule of the present invention comprising one or more untranslated regions (UTR) derived from the sequence of a cytochrome b-245 alpha polypeptide (CYBA) is a composition wherein the one or more UTR(s) comprise(s) the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14.

"One or more" in this context means that the RNA molecule may harbor one UTR comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14 of the present invention. The RNA molecule may also harbor two, three or four of these UTRs of the present invention. Alternatively, the RNA molecule may also harbor five or even more of these UTRs of the present invention.

In another preferred embodiment, the composition comprising a modified polyribonucleotide/RNA molecule of the present invention comprising one or more untranslated regions (UTR) derived from the sequence of a cytochrome b-245 alpha polypeptide (CYBA) is a composition wherein the one or more UTR(s) comprises the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15.

"One or more" in this context means that the RNA molecule may harbor one UTR comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15 of the present invention. The RNA molecule may also harbor two, three or four of these UTRs of the present invention. Alternatively, the RNA molecule may also harbor five or even more of these UTRs of the present invention.

However, the UTRs derived from the cytochrome b-245 alpha polypeptide gene as used in the present invention are not particularly limited to the above specific sequence of SEQ ID NO:14 but may also be a UTR sequence which comprises a sequence which shows 1 to 4 substitutions in comparison to SEQ ID NO:14. Alternatively, the UTR sequence may also be a sequence which comprises a sequence which shows 1 to 3 substitutions in comparison to SEQ ID NO:14. The UTR sequence may also be a sequence which comprises a sequence which shows 1 to 2 substitutions in comparison to SEQ ID NO:14. Most preferably, the UTR sequence may also be a sequence which comprises a sequence which shows 1 substitution, in comparison to SEQ ID NO:14.

Preferably, the position of the above nucleotide substitution in comparison to SEQ ID NO:14 is performed at position 32 in the sequence of SEQ ID NO:14. Preferably, the nucleotide "U" at this position is substituted by a "C". This substitution is preferred since it brings the Kozak element of CYBA which is (partially) present in SEQ ID NO:1 closer to the Kozak consensus sequence of vertebrates. The Kozak consensus sequence of vertebrates has the sequence of GCCRCCAUGG (the start codon is underlined while "R" indicates any purine) while the Kozak element of CYBA has the sequence of GuCGCCAUGG (the start codon is underlined while the deviation from the vertebrate consensus sequence is indicated by the lower case letter "u").

The UTR sequence(s) which have one or more of the above substitutions in comparison to SEQ ID NO:14 may result in an RNA molecule in the same or similar capability in terms of the translation efficiency as an RNA molecule comprising an UTR comprising SEQ ID NO:14, preferably a higher capability in terms of the translation efficiency as an RNA molecule comprising an UTR comprising SEQ ID NO:14. The property/capability of a given modified UTR sequence in comparison to in terms of the translation efficiency as an RNA molecule comprising an UTR comprising SEQ ID NO:14 with respect to the translation efficiency can be determined by the skilled person by methods known in the art and as outlined in the appended examples.

The translation efficiency is the rate of mRNA translation into polypeptides or proteins within cells. The translation efficiency of a given mRNA is measured as the number of proteins or polypeptides which are translated per mRNA per time unit. Translation is the process in which cellular ribosomes create proteins and is well-known to the skilled person. Briefly, in translation, messenger RNA (mRNA) which is produced by transcription from DNA is decoded by a ribosome to produce a specific amino acid chain or a polypeptide or a protein.

Thus, the translation efficiency of a given RNA molecule of the present invention harboring a modified UTR sequence is preferably higher in comparison to a translation efficiency of the same given RNA but harboring an UTR of SEQ ID NO:14. Accordingly, the number of proteins or polypeptides encoded by the gene of the ABC-binding cassette (ABC) family member of the RNA molecule harboring a modified UTR sequence which are translated per RNA per time unit is higher than the number of proteins or polypeptides encoded by the gene of the ABC-binding cassette (ABC) family member of the RNA molecule harboring an UTR of SEQ ID NO:14 which are translated per RNA per time unit.

In case the translation efficiency of a given RNA molecule harboring a modified UTR sequence is similar or the same in comparison to a translation efficiency of the same given RNA but harboring an UTR of SEQ ID NO:14, the number of proteins or polypeptides encoded by the gene of the ABC-binding cassette (ABC) family member of the RNA molecule harboring a modified UTR sequence which are translated per RNA per time unit is similar to or the same as the number of proteins or polypeptides encoded by the gene of the ABC-binding cassette (ABC) family member of the RNA molecule harboring an UTR of SEQ ID NO:14 which are translated per RNA per time unit. The "translation efficiency" can, e.g., be determined by methods described in the appended examples and as outlined in the following.

Translation efficiency, in the context of the present invention, is the rate of mRNA translated into protein within a cell at a certain time point in relation to the amount of mRNA encoding the respective protein in said cell at the same time point. Thus, the translation efficiency is the quotient of the mRNA translated into protein within a cell at a certain time point and the amount of mRNA encoding the respective protein. Both parameters, i.e., the mRNA translated into a protein as well as the amount of mRNA encoding the respective protein, can be determined by methods known in the art. As it has been done in the appended examples, as non-limiting examples, the amount of mRNA translated into protein within a cell can, e.g., be determined by as determined by flow cytometry (FC) while the amount of mRNA encoding the respective protein can, e.g., be measured by qPCR.

The UTR(s) comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14 as used in the present invention is/are not particularly limited to the above specific sequences and the above described substitutions but may also relate to (an) UTR sequence(s) which comprise(s) a sequence which shows (a) nucleotide(s) addition(s) in comparison to SEQ ID NO:14. The addition of (a) nucleotide(s) can be flanking. Thus, the additional nucleotide(s) may be added at the 3'-end or 5'-end of the UTR(s) of the present invention. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the invention the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as SEQ ID NO:14, preferably higher translation efficiency as SEQ ID NO:14 as defined above.

Alternatively, or in addition to these flanking additions of (a) nucleotide(s) the addition of (a) nucleotide(s) can be interspersed. Thus, the additional nucleotide(s) may be added/inserted within the nucleotide sequence of the UTR(s) of the present invention. These nucleotide(s) insertions comprise 1, 2, or 3 nucleotides as long as these sequences have a similar capability (in terms of the above-described translation efficiency) as SEQ ID NO:14, preferably higher translation efficiency as SEQ ID NO:14 as defined above.

The UTRs as used in the present invention are not particularly limited to the above specific sequence of SEQ ID NO:14 and modifications thereof. Rather, the specific sequence of SEQ ID NO:14 and modifications thereof merely define the CYBA 5' core region. Thus, in a preferred embodiment, the UTR as shown in SEQ ID NO:14 is extended on the 5' end (i.e., upstream) by at least 1 nucleotide. In another preferred embodiment, the UTR as shown in SEQ ID NO:14 is extended on the 5' end (i.e., upstream) by 1 to 20 nucleotides. Hence, in a preferred embodiment, the sequence of SEQ ID NO:14 extends by 20 nucleotides on the 5' end (i.e., upstream). In other preferred embodiments, the sequence of SEQ ID NO:14 extends by 18, 15, 13, 10, 7 or 5 nucleotides on the 5' end (i.e., upstream). In other preferred embodiments, the sequence of SEQ ID NO:14 extends by 4, 5 or 2 nucleotides on the 5' end (i.e., upstream). In other preferred embodiment, the sequence of SEQ ID NO:14 extends by 1 nucleotide on the 5' end (i.e., upstream).

These UTR sequences which are extended on the 5' end (i.e., upstream) may also be modified as defined herein above for SEQ ID NO:14. Accordingly, the same applies, mutatis mutandis, to the UTRs which are extended on the 5' end as defined above as has been set forth above in the context of the UTR of SEQ ID NO:14.

Moreover, the UTRs as used in the present invention are also not particularly limited to the above specific sequence of SEQ ID NO:15 but may also be a UTR sequence which comprises a sequence which shows 1 to 7 substitutions in comparison to SEQ ID NO:15. Alternatively, the UTR sequence may also be a sequence which comprises a sequence which shows 1 to 6 substitutions in comparison to SEQ ID NO:15. The UTR sequence may also be a sequence which comprises a sequence which shows 1 to 5 substitutions in comparison to SEQ ID NO:15. The UTR sequence may also be a sequence which comprises a sequence which shows 1 to 4 substitutions in comparison to SEQ ID NO:15. The UTR sequence may also be a sequence which comprises a sequence which shows 1 to 3 substitutions in comparison to SEQ ID NO:15. The UTR sequence may also be a sequence which comprises a sequence which shows 1 to 2 substitutions in comparison to SEQ ID NO:15. The UTR sequence may also be a sequence which comprises a sequence which shows 1 to 3 substitutions in comparison to SEQ ID NO:15. Most preferably, the UTR sequence may also be a sequence which comprises a sequence which shows 1 substitution, in comparison to SEQ ID NO:15.

The UTR sequence(s) which have one or more of the above substitutions in comparison to SEQ ID NO:15 may result in an RNA molecule in the same or similar capability in terms of the translation efficiency as an RNA molecule comprising an UTR comprising SEQ ID NO:15, preferably a higher capability in teiius of the translation efficiency as an RNA molecule comprising an UTR comprising SEQ ID NO:15. The property/capability of a given modified UTR sequence in comparison to in terms of the translation efficiency as an RNA molecule comprising an UTR comprising SEQ ID NO:15 with respect to the translation efficiency can be determined by the skilled person by methods known in the art and as outlined in the appended examples.

The translation efficiency is the rate of mRNA translation into polypeptides or proteins within cells. The translation efficiency of a given mRNA is measured as the number of proteins or polypeptides which are translated per mRNA per time unit. Translation is the process in which cellular ribosomes create proteins and is well-known to the skilled person. Briefly, in translation, messenger RNA (mRNA) which is produced by transcription from DNA is decoded by a ribosome to produce a specific amino acid chain or a polypeptide or a protein.

Thus, the translation efficiency of a given RNA molecule harboring a modified UTR sequence is preferably higher in comparison to a translation efficiency of the same given RNA but harboring an UTR of SEQ ID NO:15. Accordingly, the number of proteins or polypeptides encoded by the gene of the ABC-binding cassette (ABC) family member of the RNA molecule harboring a modified UTR sequence which are translated per RNA per time unit is higher than the number of proteins or polypeptides encoded by the coding region of the RNA molecule harboring an UTR of SEQ ID NO:15 which are translated per RNA per time unit.

In case the translation efficiency of a given RNA molecule harboring a modified UTR sequence is similar or the same in comparison to a translation efficiency of the same given RNA but harboring an UTR of SEQ ID NO:15, the number of proteins or polypeptides encoded by the coding region of the RNA molecule harboring a modified UTR sequence which are translated per RNA per time unit is similar to or the same as the number of proteins or polypeptides encoded by the gene of the ABC-binding cassette (ABC) family member of the RNA molecule harboring an UTR of SEQ ID NO:15 which are translated per RNA per time unit.

The "translation efficiency" can, e.g., be determined by methods described in the appended examples and as outlined above.

The UTR(s) comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15 as used in the present invention is/are not particularly limited to the above specific sequences and the above described substitutions but may also relate to (an) UTR sequence(s) which comprise(s) a sequence which shows (a) nucleotide(s) addition(s) in comparison to SEQ ID NO:15. The addition of nucleotide(s) can be flanking or interspersed. Thus, the additional nucleotide(s) may be added at the 3 '-end or 5'-end of the UTR(s) of the present invention. Alternatively, or in addition to these flanking additional nucleotide(s), the additional nucleotide(s) may also be within the nucleotide sequence of the UTR(s) of the present invention. The additional nucleotide(s) comprise polynucleotide chains of up to 0 (no changes), 1, 2, 3, 4, 5, 6, 7, 8, 9 or 10 nucleotides, preferably of up to 20 nucleotides or even more preferably of up to 30 nucleotides. In light of the rationale that the addition of nucleotides is likely not to change the above functional properties of the UTR(s) of the invention the addition of the nucleotides may also have a length of up to 40, 50, 60, 70, 80, 90, or even 100 nucleotides or even more, up to 200, 300, 400 or 500 nucleotides as long as these sequences have a similar capability (in terms of the above-described translation efficiency) as SEQ ID NO:15, preferably higher translation efficiency as SEQ ID NO:15 as defined above.

The UTR(s) of the present invention as well as RNA molecules containing such UTR(s) may be recombinantly (e.g., in an in vivo or an in vitro system) or synthetically generated/synthesized by methods known to the person skilled in the art.

More specifically, the UTRs of the present invention and RNA molecules containing such UTR(s) may be produced either recombinantly in in vivo systems by methods known to the person skilled in the art.

Alternatively, the UTRs of the present invention and RNA molecules containing such UTR(s) may be produced in an in vitro system using, for example, an in vitro transcription system. In vitro transcription systems are commonly known and usually require a purified linear DNA template containing a DNA sequence "encoding" module (b) and/or module (c) as outlined in detail further below wherein said DNA sequence is under the control of an appropriate promoter. Moreover, an in vitro transcription system also commonly requires ribonucleoside triphosphates, a buffer system that includes DTT and magnesium ions, and an appropriate RNA polymerase which provides the enzymatic activity for the in vitro transcription of the DNA sequence "encoding" said UTR(s) into the UTR(s) of the present invention.

Furthermore, the UTRs of the present invention and RNA molecules containing such UTR(s) may be chemically synthesized, e.g., by conventional chemical synthesis on an automated nucleotide sequence synthesizer using a solid-phase support and standard techniques or by chemical synthesis of the respective DNA-sequences and subsequent in vitro or in vivo transcription of the same.

In molecular biology and genetics, upstream and downstream both refer to a relative position in an RNA molecule. In the context of the present invention, upstream is toward the 5' end of the RNA molecule and downstream is toward the 3' end of the molecule.

Accordingly, in one embodiment, the UTR comprising the sequence as shown in SEQ ID NO:14 or a sequence which has 1 to 4 substitutions in comparison to SEQ ID NO:14 and which results in an RNA molecule having the same or a higher translation efficiency as an RNA molecule comprising an UTR comprising SEQ ID NO:14 as defined hereinabove (in the following referred to as "module (b)") is located upstream of the modified polyribonucleotide encoding the ABC-binding cassette (ABC) family member as described herein above and below (in the following referred to as "module (a)"). Moreover, in one embodiment, the UTR comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15 as defined hereinabove (in the following referred to as "module (c)") is located downstream of the modified polyribonucleotide encoding the ABC-binding cassette (ABC) family member as described herein above and below (in the following referred to as "module (a)"). Yet, preferably, the gene encoding the ABC-binding cassette (ABC) family member ("module (a)") is located between the UTR module (b) and the UTR module (c) and, accordingly, the RNA molecule preferably has the arrangement of 5'-(b)-(a)-(c)-3'.

In case the RNA molecule only harbors one UTR module (i.e., either module (b) (i.e., the one or more UTR(s) comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14 as defined hereinabove) or module (c) (i.e., the one or more UTR(s) comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15 as defined hereinabove)) the RNA molecule preferably has the arrangement of 5'-(b)-(a)-3' or 5'-(a)-(c)-3'. 1981 In the following, preferred arrangements of the UTR modules (b) and/or (c) of the present invention in relation to the modified polyribonucleotide encoding the ABC-binding cassette (ABC) family member ("module (a)") are described wherein the UTR module (b) (corresponding to the above-defined 5' UTR fragment of the CYBA mRNA) is located upstream of the coding region (i.e., at the 5' end of the coding region) and/or the UTR module (c) (corresponding to the above-defined 3' UTR of the CYBA mRNA) is located downstream of the coding region (i.e., at the 3' end of the coding region).

Thus, in a preferred embodiment, and in accordance with the foregoing, the present invention relates to an RNA molecule comprising (a) a modified polyribonucleotide, i.e., a coding region encoding the ABC-binding cassette (ABC) family member; and (b) one or more UTR(s) comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14, and wherein said UTR(s) as defined in (b) is/are located at the 5' end of the coding region as defined in (a).

In a preferred embodiment, and in accordance with the foregoing, the present invention relates to an RNA molecule comprising (a) a coding region coding for an ABC-binding cassette (ABC) family member; and (c) one or more UTR(s) comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15, wherein said UTR(s) as defined in (c) is/are located at the 3' end of the coding region as defined in (a).

In a preferred embodiment, and in accordance with the foregoing, the present invention relates to an RNA molecule comprising (a) a coding region coding an ABC-binding cassette (ABC) family member; and (b) one or more UTR(s) comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14; and (c) one or more UTR(s) comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15, wherein said UTR(s) as defined in (b) is/are located at the 5' end of the coding region as defined in (a) and wherein said UTR(s) as defined in (c) is/are located at the 3' end of the coding region as defined in (a).

In a preferred embodiment, and in accordance with the foregoing, the present invention relates to an RNA molecule comprising (a) a coding region coding for an ABC-binding cassette (ABC) family member; and (b) one UTR comprising the sequence as shown in SEQ ID NO:14 or a sequence which shows 1 to 4 substitutions in comparison to SEQ ID NO:14 and which results in an RNA molecule having the same or a higher translation efficiency as an RNA molecule comprising an UTR comprising SEQ ID NO:14; and (c) two UTRs comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15; wherein said RNA molecule comprises said one UTR as defined in (b) at the 5' end of the coding region as defined in (a) and which comprises said two UTRs as defined in (c) at the 3' end of the coding region as defined in (a).

In a preferred embodiment, and in accordance with the foregoing, the present invention relates to an RNA molecule comprising (a) a coding region coding an ABC-binding cassette (ABC) family member; and (c) two UTRs comprising the sequence as shown in SEQ ID NO:15 or a sequence which shows 1 to 7 substitutions in comparison to SEQ ID NO:15 and which results in an RNA molecule having the same or a higher translation efficiency as an RNA molecule comprising an UTR comprising SEQ ID NO:15, wherein said RNA molecule comprises said two UTRs as defined in (c) at the 3' end of the coding region as defined in (a).

The construct according to the present invention may not only comprise the above three main modules (a), (b) and/or (c). Rather, it may be desirable that between the individual modules (a) linker moiety/moieties and/or (a) multiple cloning site(s) is/are placed which may, e.g., facilitate the construction of the construct. Suitable linker moieties and multiple cloning sites are known to the skilled person.

The position of the UTR modules (b) and/or (c) within the RNA molecule of the present invention in relation to module (a) (i.e., the coding region coding an ABC-binding cassette (ABC) family member), is not particularly limited and, accordingly, between the individual modules of the RNA molecule of the present invention there may be a spacing or a gap filled with one or more nucleotides G, A, U and/or C which are not part of the main modules (a), (b) and/or (c).

"One or more nucleotides G, A, U and/or C" in this context means that the spacing or gap between the individual modules of the RNA molecule of the present invention is/are filled with 1, 2, 3, 4, 5, 6, 7, 8, 9 or 10 nucleotides G, A, U and/or C. In other preferred embodiments, the spacing or gap between the individual modules of the RNA molecule of the present invention are filled with 20, 30, 40, 50, 60, 70, 80, 90, 100 or 110 or more nucleotides G, A, U and/or C.

Yet, in a preferred embodiment, the UTR module (b) or (c), within the RNA molecule of the present invention in relation to module (a) (i.e., the coding region coding an ABC-binding cassette (ABC) family member), is directly placed adjacent to the start codon of the coding region of module (a) without any spacing or gap in between, i.e., directly upstream of the start codon of the coding region of module (a).

In another preferred embodiment, the UTR module (b) or (c), within the RNA molecule of the present invention in relation to module (a) (i.e., the coding region), is directly placed adjacent to the termination codon (i.e., the stop codon) of the coding region of module (a) coding an ABC-binding cassette (ABC) family member without any spacing or gap in between, i.e., directly downstream of the termination codon/stop codon of the coding region of module (a) coding an ABC-binding cassette (ABC) family member.

In a preferred embodiment, the UTR module (b), within the RNA molecule of the present invention in relation to module (a) (i.e., the coding region coding an ABC-binding cassette (ABC) family member), is directly placed adjacent to the start codon of the coding region of module (a) coding an ABC-binding cassette (ABC) family member without any spacing or gap in between, i.e., directly upstream of the start codon of the coding region of module (a) coding an ABC-binding cassette (ABC) family member and the UTR module (c), within the RNA molecule of the present invention in relation to module (a) (i.e., the coding region coding an ABC-binding cassette (ABC) family member), is directly placed adjacent to the termination codon (i.e., the stop codon) of the coding region of module (a) coding an ABC-binding cassette (ABC) family member without any spacing or gap in between, i.e., directly downstream of the termination codon/stop codon of the coding region of module (a) coding an ABC-binding cassette (ABC) family member.

In even more preferred embodiments, the composition comprising a modified polyribonucleotide of the present invention comprising one or more untranslated regions (UTRs) derived from the sequence of a cytochrome b-245 alpha polypeptide (CYBA) as defined herein above is a composition wherein the modified polynucleotide encodes the ABC-binding cassette (ABC) 3 protein (ABCA3), preferably encodes the human ABCA3 protein, wherein said modified polynucleotide includes a codon sequence that is optimized for translation within cells of the subject exposed to the modified polyribonucleotide.

In a most preferred embodiment, the composition comprising a modified polyribonucleotide of the present invention comprising one or more untranslated regions (UTRs) derived from the sequence of a cytochrome b-245 alpha polypeptide (CYBA) as defined herein above is the mRNA sequence of a codon optimized ABCA3 DNA sequence with a 5' CYBA UTR and a 3' CYBA UTR (SEQ ID NO: 12), or a codon optimized ABCA3 mRNA sequence with a 5' CYBA UTR and a 3' CYBA UTR (SEQ ID NO: 13).

Other non-UTR sequences can be incorporated into the 5' (or 3' UTR) UTRs of the polyribonucleotides of the present disclosure. The 5' and/or 3' UTRs can provide stability and/or translation efficiency of polyribonucleotides. For example, introns or portions of intron sequences can be incorporated into the flanking regions of an engineered polyribonucleotide. Incorporation of intronic sequences can also increase the rate of translation of the polyribonucleotide.

3' UTRs may have stretches of Adenosines and Uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-α. Class III ARES are less well defined. These U rich regions do not contain an AUUUA motif c-Jun and Myogenin are two well-studied examples of this class. Proteins binding to the AREs may destabilize the messenger, whereas members of the ELAV family, such as HuR, may increase the stability of mRNA. HuR may bind to AREs of all the three classes. Engineering the HuR specific binding sites into the 3' UTR of nucleic acid molecules can lead to HuR binding and thus, stabilization of the message in vivo.

Engineering of 3' UTR AU rich elements (AREs) can be used to modulate the stability of an engineered polyribonucleotide. One or more copies of an ARE can be engineered into a polyribonucleotide to modulate the stability of a polyribonucleotide. AREs can be identified, removed or mutated to increase the intracellular stability and thus increase translation and production of the resultant protein. Transfection experiments can be conducted in relevant cell lines, using engineered polyribonucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

An untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

An engineered polyribonucleotide of the disclosure can comprise one or more introns. An intron can comprise any number of modified or unmodified nucleotides. An intron can comprise, for example, at least 1 base or base pair, 50 bases or base pairs, 100 bases or base pairs, 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, or 5000 bases or base pairs. In some cases, an intron can comprise, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs.

In some cases, a percentage of the nucleotides in an intron are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in an intron are modified. In some cases, all of the nucleotides in an intron are modified.

An engineered polyribonucleotide of the disclosure can comprise a polyA sequence. A polyA sequence (e.g., polyA tail) can comprise any number of nucleotides. A polyA sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. In some examples, a polyA sequence is at least about 100, 110, 120, 130, 140, 150, 160, 170, 180, 190, or 200 nucleotides in length. A polyA sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length. A polyA sequence can comprise a length of at most 100 bases or base pairs, 90 bases or base pairs, 80 bases or base pairs, 70 bases or base pairs, 60 bases or base pairs, 50 bases or base pairs, 40 bases or base pairs, 30 bases or base pairs, 20 bases or base pairs, 10 bases or base pairs, or 5 bases or base pairs.

In some cases, a percentage of the nucleotides in a poly-A sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a poly-A sequence are modified. In some cases, all of the nucleotides in a poly-A are modified.

A linker sequence can comprise any number of nucleotides. A linker can be attached to the modified nucleobase at an N-3 or C-5 position. The linker attached to the nucleobase can be diethylene glycol, dipropylene glycol, triethylene glycol, tripropylene glycol, tetraethylene glycol, tetraethylene glycol, divalent alkyl, alkenyl, alkynyl moiety, ester, amide, or an ether moiety. A linker sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. A linker sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or at least 10000 bases or base pairs in length. A linker at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs in length.

In some cases, a percentage of the nucleotides in a linker sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a linker sequence are modified. In some cases, all of the nucleotides in a linker sequence are modified.

In some cases, an engineered polyribonucleotide can include at least one stop codon before the 3'untranslated region (UTR). In some cases, an engineered polyribonucleotide includes multiple stop codons. The stop codon can be selected from TGA, TAA and TAG. The stop codon may be modified or unmodified. In some cases, the engineered polyribonucleotide includes the stop codon TGA and one additional stop codon. In some cases, the engineered polyribonucleotide includes the addition of the TAA stop codon.

Encoded Polypeptides

The encoded polypeptides are polymer chains comprised of amino acid residue monomers which are joined together through amide bonds (peptide bonds). The amino acids may be the L-optical isomer or the D-optical isomer. A polypeptide can be a chain of at least three amino acids, peptide-mimetics, a protein, a recombinant protein, an antibody (monoclonal or polyclonal), an antigen, an epitope, an enzyme, a receptors, a vitamin, or a structure analogue or combinations thereof. A polyribonucleotide that is translated within a subject's body can generate an ample supply of specific peptides or proteins within a cell, a tissue, or across many cells and tissues of a subject. In some cases, a polyribonucleotide can be translated in vivo within the cytosol of a specific target cell(s) type or target tissue. In some cases, a polyribonucleotide can be translated in vivo to provide an ABCA3 protein, a functional fragment thereof, or a protein that is at least 70% homologous to a human ABCA3 protein. In some cases, a polyribonucleotide can be translated in vivo in various non-target cell types or target tissue(s). Non-limiting examples of cells that be target or non-target cells include: a) skin cells, e.g.: keratinocytes, melanocytes, urothelial cells; b) neural cells, e.g.: neurons, Schwann cells, oligodentrocytes, astrocytes; c) liver cells, e.g.: hepatocytes; d) intestinal cells, e.g.: globlet cell, enterocytes; e) blood cells; e.g.: lymphoid or myeloid cells. Non-limiting examples of tissues include connective tissue, muscle tissue, nervous tissue, or epithelial tissue. In some cases, a target cell or a target tissue is a cancerous cell, tissue, or organ.

A polynucleotide sequence can be derived from one or more species. For example, a polynucleotide sequence can be derived from a human (*Homo sapiens*), a mouse (e.g., *Mus musculus*), a rat (e.g., *Rattus norvegicus* or *Rattus rattus*), a camel (e.g., *Camelus dromedarius* or *Camelus bactrianus*), a llama (*Lama vicugna*), or any other suitable creature. A polynucleotide sequence can be a chimeric combination of the sequence of one or more species.

In some cases, the endogenous translational machinery can add a post-translational modification to the encoded peptide. A post-translational modification can involve the addition of hydrophobic groups that can target the polypeptide for membrane localization, the addition of cofactors for increased enzymatic activity, or the addition of smaller chemical groups. The encoded polypeptide can also be post-translationally modified to receive the addition of other peptides or protein moieties. For instance, ubiquitination can lead to the covalent linkage of ubiquitin to the encoded polypeptide, SUMOylation can lead to the covalent linkage of SUMO (Small Ubiquitin-related MOdifier) to the encoded polypeptide, ISGylation can lead to the covalent linkage of ISG15 (Interferon-Stimulate Gene 15).

In some cases, the encoded polypeptide can be post-translationally modified to undergo other types of structural changes. For instance, the encoded polypeptide can be proteolytically cleaved, and one or more proteolytic fragments can modulate the activity of an intracellular pathway. The encoded polypeptide can be folded intracellularly. In some cases, the encoded polypeptide is folded in the presence of co-factors and molecular chaperones. A folded polypeptide can have a secondary structure and a tertiary structure. A folded polypeptide can associate with other folded peptides to form a quaternary structure. A folded-peptide can folio a functional multi-subunit complex, such as an antibody molecule, which has a tetrameric quaternary structure. Various polypeptides that form classes or isotypes of antibodies can be expressed from a polyribonucleotide.

The encoded polypeptide can be post-translationally modified to change the chemical nature of the encoded amino acids. For instance, the encoded polypeptide can undergo post-translational citrullination or deimination, the conversion of arginine to citrulline. The encoded polypeptide can undergo post-translation deamidation; the conversion of glutamine to glutamic acid or asparagine to aspartic acid. The encoded polypeptide can undergo eliminylation, the conversion of an alkene by beta-elimination of phosphothreonine and phosphoserine, or dehydration of threonine and serine, as well as by decarboxylation of cysteine. The encoded peptide can also undergo carbamylation, the conversion of lysine to homocitrulline. An encoded peptide can also undergo racemization, for example, racemization of proline by prolyl isomerase or racemization of serine by protein-serine epimerase.

The activity of a plurality of biomolecules can be modulated by a molecule encoded by a polyribonucleotide. Non-limiting examples of molecules whose activities can be modulated by an encoded polynucleotide include: amino acids, peptides, peptide-mimetics, proteins, recombinant proteins antibodies (monoclonal or polyclonal), antibody fragments, antigens, epitopes, carbohydrates, lipids, fatty acids, enzymes, natural products, nucleic acids (including DNA, RNA, nucleosides, nucleotides, structure analogues or combinations thereof), nutrients, receptors, and vitamins.

Non-limiting examples of nucleotide sequences that can be a part of a polynucleotide of the disclosure are disclosed in TABLE 6.

TABLE 6

| Name | Sequence |
| --- | --- |
| ABCA3 *Homo sapiens* | NC_000016.10 |
| ABCA3 *mus musculus* | NC_000083.6 |
| ABCA3 *Rattus norvegicus* | NC_005109.4 |
| abcA3 *Dictyostelium discoideum* | NC_007092.3 |
| ABCA3 *Bos taurus* | AC_000182.1 |
| ABCA3 *Pan troglodytes* | NC_006483.3 |
| ABCA3 *Canis lupus familiaris* | NC_006588.3 |
| ABCA3 *Gallus gallus* | NC_006101.3 |
| ABCA3 *Leishmania infantum* | NC_009395.2 |
| ABCA3 *Xenopus tropicalis* | NW_004668244.1 |

A polypeptide sequence can share a % homology to an amino acid sequence of an endogenous polypeptide. A polypeptide sequence can share at most 10% homology, at most 20% homology, at most 30% homology, at most 40% homology, at most 50% homology, at most 60% homology, at most 70% homology, at most 80% homology, at most 90% homology, or at most 99% homology with an amino acid sequence of an endogenous polypeptide. Various methods and software programs can be used to determine the homology between two or more peptides, such as NCBI BLAST, Clustal W, MAFFT, Clustal Omega, AlignMe, Praline, or another suitable method or algorithm.

Immunogenicity

Many pharmaceutical agents, including compositions comprising molecules of various sizes (polynucleotides, proteins, or enzymes) can trigger an immune response when administered to a subject. In many cases, the immune system recognizes the composition as a foreign body and neutralizes its pharmaceutical action. A polyribonucleotide and a composition of the present disclosure can have low immunogenicity or be non-immunogenic, thereby triggering a small response by the immune system, or not triggering any immune response at all.

The immunogenicity can also be determined by measurement of, for example, the TNF-α and IL-8 levels and the binding capacity to TLR-3, TLR-7, TLR-8 and helicase RIG-1. In order thereby to establish whether a polyribonucleotide has a desired low immunogenicity, the quantity of one or more of the factors can be measured after administration of the polyribonucleotide to a subject. The immunogenicity of a polypeptide can be determined in relation to an increase in the number of white blood cells upon administration of the polypeptide to the subject. In some cases, upon administration of the composition to the subject, the subject exhibits an increase in the number of white blood cells that is less than 90%, less than 80%, less than 70%, less than 60%, less than 50%, less than 40%, less than 30%, less than 20%, or less than 10%. A polyribonucleotide of the disclosure can trigger minimum or insignificant inflammatory or immunological reactions.

For the determination of the immunogenicity of a polyribonucleotide, various methods can be used. A very suitable method is the determination of inflammatory markers in cells or a simple white cell blood count, as a reaction to the administration of the polyribonucleotide. Such a method is described in the examples. Cytokines which are associated with inflammation, such as, for example TNF-α, IFN-α, IFN-β, IL-8, IL-6, and/or IL-12, can be measured. The expression of dendritic cell activation markers can also be used for the estimation of immunogenicity. A further indication of an immunological reaction can be the detection of binding to the Toll-like receptors TLR-3, TLR-7 and TLR-8 and to helicase RIG-1.

The immunogenicity of a polyribonucleotide can be determined as an overall increase in the level of inflammatory marker or white blood cell count as compared to a level prior to the administration of the polyribonucleotide. For instance, an engineered polyribonucleotide that is unmodified or modified can be administered to cells, or to a subject, and the secretion of inflammatory markers in a defined time interval as a reaction to the administration of the polyribonucleotide can be measured.

Compositions

"Naked" polynucleotide compositions can be successfully administered to a subject, and uptaken by a subject's cell, without the aid of carriers, stabilizers, diluents, dispersing agents, suspending agents, thickening agents, and/or excipients (Wolff et al. 1990, Science, 247, 1465-1468). However, in many instances, encapsulation of polynucleotides with formulations that can increase the endocytotic uptake can increase the effectiveness of a composition of the disclosure.

Another technical challenge underlying the delivery of polyribonucleotides to multicellular organisms is to identify a composition that provides a high efficiency delivery of polyribonucleotides that are translated within a cell or a tissue of a subject. It has been recognized that administration of naked nucleic acids may be highly inefficient and may not provide a suitable approach for administration of a polynucleotide to a multicellular organism.

To solve this challenge, a composition comprising an engineered polyribonucleotide can be encapsulated or formulated with a pharmaceutical carrier. The formulation may be, but is not limited to, nanoparticles, poly(lactic-co-glycolic acid)(PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof. A composition comprising an engineered polyribonucleotide disclosed herein can comprise from about 1% to about 99% weight by volume of a carrier system. The amount of carrier present in a carrier system is based upon several different factors or choices made by the formulator, for example, the final concentration of the polyribonucleotide and the amount of solubilizing agent. Various carriers have been shown useful in delivery of different classes of therapeutic agents. Among these carriers, biodegradable nanoparticles formulated from biocompatible polymers poly(D,L-lactide-co-glycolide) (PLGA) and polylactide (PLA) have shown the potential for sustained intracellular delivery of different therapeutic agents.

The loading weight percent of the engineered polynucleotide in a composition may be at least 0.05%, 0.1%, 0.2%, 0.3%, 0.4%, 0.5%, 1%, 2%, 4%, 5%, 6%, 7%, 8%, 9%, or 10%. The encapsulation efficiency of the modified mRNA in the PLGA microsphere may be at least 50%, at least 70%, at least 90%, at least 95%, at least 96%, at least 97%, at least 98%, or at least 99%.

The present disclosure describes nanoparticles, oligomers, polymers or lipidoids comprising oligo(alkylene amines) containing alternating, non-identical alkylene amine units which are useful for delivering a polynucleotide, in some cases an engineered polyribonucleotides, into a cell or into a tissue. A composition disclosed herein can be stable for at least about 1 minute, 5 minutes, 10 minutes, 30 minutes, 1 hour, 2 hours, 3 hours, 4 hours, 5 hours, 6 hours, 12 hours, 1 day, 2 days, 3 days, 4 days, 5 days, 6 days, 7 days, 8 days, 9 days, 10 days, 2 weeks, 4 weeks, 6 weeks, 8 weeks, 10 weeks, 12 weeks, 3 months, 4 months, 5 months, 6 months, 7 months, 8 months, 9 months, 10 months, 11 months, or one year. A formulation disclosed herein can be stable, for example, at a temperature of at least about 0° C., 5° C., 10° C., 15° C., 20° C., 25° C., 30° C., 35° C., 40° C., 45° C., 50° C., 60° C., 70° C., or 80° C. A composition of the disclosure can have a desired density. The density of a composition can improve a property of the composition, such as the rheology of the composition.

Nanoparticles

The present disclosure also provides nanoparticle based formulations of engineered polyribonucleotides that are able to translocate following administration to a subject. In some instances, the administration is pulmonary and the engineered polyribonucleotides can move intact either actively or passively from the site of administration to the systemic blood supply and subsequently to be deposited in different cells or tissues, such as, e.g., the breast. This translocation of the nanoparticle comprising an engineered polyribonucleotide encoding a therapeutic protein, such as, e.g., ABCA3 or a functional fragment thereof, constitutes non-invasive systemic delivery of an active pharmaceutical ingredient beyond the lung to result in the production of a functional protein to systemically accessible non-lung cells or tissues.

A nanoparticle can be a particle of particle size from about 10 nanometers (nm) to 5000 nm, 10 nm to 1000 nm, or 60 nm to 500 nm, or 70 nm to 300 nm. In some examples, a nanoparticle has a particle size from about 60 nm to 225 nm. The nanoparticle can include an encapsulating agent (e.g., coating) that encapsulates one or more polyribonucleotides, which may be engineered polyribonucleotides. The nanoparticle can include engineered and/or naturally occurring polyribonucleotides. The encapsulating agent can be a polymeric material, such as PEI or PEG.

A lipidoid or lipid nanoparticle which may be used as a delivery agent may include a lipid which may be selected from the group consisting of C12-200, MD1, 98N12-5, DLin-DMA, DLin-K-DMA, DLin-KC2-DMA, DLin-MC3-DMA, PLGA, PEG, PEG-DMG, PEGylated lipids and analogues thereof. A suitable nanoparticle can comprise one or more lipids in various ratios. For example, a composition of the disclosure can comprise a 40:30:25:5 ratio of C12-200:DOPE:Cholesterol:DMG-PEG2000 or a 40:20:35:5 ratio of HGT5001:DOPE:Cholesterol:DMG-PEG2000. A nanoparticle can include at least 1, 2, 3, 4, 5, 6, 7, 8, 9, 10 lipids or another suitable number of lipids. A nanoparticle can be formed of any suitable ratio of lipids selected from the group consisting of C12-200, MD1, 98N12-5, DLin-DMA, DLin-K-DMA, DLin-KC2-DMA, DLin-MC3-DMA, PLGA, PEG, PEG-DMG.

The mean size of the nanoparticle formulation may comprise the modified mRNA between 60 nanometers (nm) and 225 nm. The polydispersity index PDI of the nanoparticle formulation comprising the modified mRNA can be between 0.03 and 0.15. The zeta potential of the nanoparticle formulation may be from −10 to +10 at a pH of 7.4. The formulations of modified mRNA may comprise a fusogenic lipid, cholesterol and a PEG lipid. The formulation may have a molar ratio 50:10:38.5:1.5-3.0 (cationic lipid:fusogenic lipid:cholesterol:polyethylene glycol (PEG) lipid). The PEG lipid may be selected from, but is not limited to PEG-c-DOMG, PEG-DMG. The fusogenic lipid may be DSPC. A lipid nanoparticle of the present disclosure can be formulated in a sealent such as, but not limited to, a fibrin sealant.

Oligo(Alkylene Amine Groups)

It has also been recognized that although encapsulation of polynucleotides with some formulations can increase the endocytotic uptake of a composition, the polynucleotide that is taken up by a cell may not be effectively translated within the cell. Some formulations may be effectively used for plasmid DNA and/or siRNA delivery, while not practical for use in the delivery of polyribonucleotides. The present disclosure provides formulations that can be employed for effective delivery and translation of polyribonucleotide compositions to a subject.

A composition of the disclosure can be designed to provide a polyribonucleotide that is effectively translated within a cell. A composition of the disclosure can comprise an arrangement of alkylene amine units of alternating length in groups of three or more units and containing an ethyleneamine unit in compositions for transfecting a cell with any polynucleotide, such as an engineered polyribonucleotide. A composition of the disclosure can provide a more efficacious delivery of a polyribonucleotide to a cell than analogous arrangements of alkylene amine units of non-alternating length.

Oligomers, polymers or lipidoids can be provided which share a common structural entity which is illustrated in formula (I):

(I)

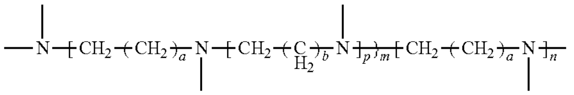

A composition of the disclosure can comprise an oligo (alkylene amine) that is selected from:

a) an oligomer or polymer comprising a plurality of groups of formula (II) as a side chain and/or as a terminal group:

(II)

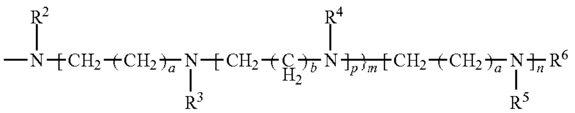

wherein the variables a, b, p, m, n, and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is ≥2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; and a poly(ethylene glycol) chain;

$R^6$ is selected from hydrogen; a group —CH2-CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; —C(NH)—NH; a poly(ethylene glycol) chain; and a receptor ligand, and wherein one or more of the nitrogen atoms indicated in formula (II) may be protonated to provide a cationic group of formula (II).

b) an oligomer or polymer comprising a plurality of groups of formula (III) as repeating units:

(III)

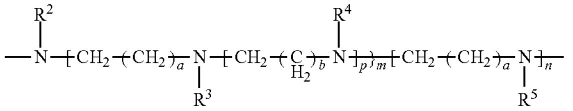

wherein the variables a, b, p, m, n, and $R^2$ to $R^5$ are defined as follows, independently for each group of formula (III) in a plurality of such groups:

a is 1 and b is an integer of 2 to 4; or a is an integer of 2 to 4 and b is 1, p is 1 or 2, m is 1 or 2; n is 0 or 1 and m+n is 2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, —$CH_2$—$R^7$ or —$CH_2$— wherein $R^7$ is selected from C3-C18 alkyl or C3-C18 alkenyl having one C—C double bond; a protecting group for an amino group; and a poly (ethylene glycol) chain;

and wherein one or more of the nitrogen atoms indicated in formula (III) may be protonated to provide a cationic group of formula (III).

c) a lipidoid having the structure of formula (IV):

(IV)

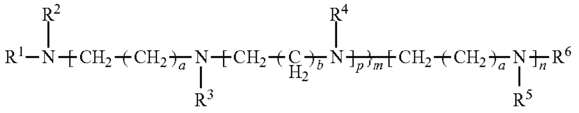

wherein the variables a, b, p, m, n, and $R^2$ to $R^6$ are defined as follows:

a is 1 and b is an integer of 2 to 4; or a is an integer of 2 to 4 and b is 1, p is 1 or 2, m is 1 or 2; n is 0 or 1 and m+n is ≥2; and $R^2$ to $R^6$ are, independently of each other, selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; and a poly(ethylene glycol) chain; and a receptor ligand; provided that at least two residues among $R^1$ to $R^6$ are a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond;

and wherein one or more of the nitrogen atoms indicated in formula (IV) may be protonated to provide a cationic group of formula (IV).

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

The oligo(alkylene amine) structures of formulae (II), (III) and (IV) are characterized in that they can combine shorter (also referred to for illustration as "S") ethylene amine units (i.e., a or b is 1) with longer (also referred to for illustration as "L") alkylene amine units (i.e., the other one of a or b is an integer of 2 to 4) in an alternating manner. Such an arrangement of the protonatable units can provide advantages in terms of the suitability of the resulting group to provide a vehicle for delivering polyribonucleotides into a cell.

A composition of the disclosure can comprise a plurality of oligo(alkylene amine) groups of formula (II) as a side chain or as a terminal group:

$$—NR^2\{CH_2—(CH_2)_a—NR^3—[CH_2—(CH_2)_b—NR^4]_p\}_m—[CH_2{}^-(CH_2)_a—NR^5]_n—R^6 \quad \text{(II)},$$

wherein the variables a, b, p, m, n, and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is 2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; —C(NH)—$NH_2$—; and a poly(ethylene glycol) chain;

$R^6$ is selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C16 alkyl or C3-C16 alkenyl having one C—C double bond; a protecting group for an amino group; —C(NH)—NH; a poly(ethylene glycol) chain; and a receptor ligand.

In some cases, $R^2$ to $R^5$ are hydrogen and $R^6$ is selected from hydrogen, a protecting group for an amino group; —C(NH)—$NH_2$ and a poly(ethylene glycol) chain. In some cases, $R^2$ to $R^6$ are hydrogen. In some cases, $R^7$ is selected from C8-C18 alkyl or C8-C18 alkenyl having one C—C double bond, or from C8-C12 alkyl or C8-C12 alkenyl having one C—C double bond, or from C10-C12 alkyl or C10-C12 alkenyl having one C—C double bond. A composition of the disclosure can comprise one, or multiple alkylene groups of formulas (II)-(IV).

In some cases, the oligomers or polymers which can be used in the compositions in accordance with the present disclosure comprise a plurality of oligo (alkylene amine) groups of formula (III) as repeating units:

$$NR^2\{CH_2—(CH_2)_a—NR^3—[CH_2—(CH_2)_b—NR^4]_p\}_m—[CH_2—(CH_2)_a—NR^5]_n— \quad \text{(III)}$$

wherein the variables a, b, p, m, n, and $R^2$ to $R^5$ are defined as follows, independently for each group of formula (III) in a plurality of such groups:

a is 1 and b is an integer of 2 to 4; or a is an integer of 2 to 4 and b is 1, p is 1 or 2, m is 1 or 2; n is 0 or 1 and m+n is ≥2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, —$CH_2$—$R^7$ or —$CH_2$— wherein $R^7$ is selected from C3-C18 alkyl or C3-C18 alkenyl having one C—C double bond; a protecting group for an amino group; —C(NH)—$NH_2$; a poly(ethylene glycol) chain; and endosomal escape effector and a receptor ligand. In some cases, $R^2$ to $R^5$ are hydrogen. In some cases, $R^7$ is selected from C8-C18 alkyl or C8-C18 alkenyl having one C—C. $R^7$ may be selected from C8-C12 alkyl or C8-C12 alkenyl having one C—C. As an alternative, $R^7$ may be selected from C10-C12 alkyl or C10-C12 alkenyl having one C—C.

One or more of the nitrogen atoms indicated in formula (III) may be protonated to provide a cationic group of formula (III).

Optionally, the oligomers or polymers which comprise a plurality of groups of formula (III) as repeating units can comprise, in addition, one or more oligo(alkylene amine) group(s) of formula (II) as a side chain and/or as a terminal group.

In a plurality of groups of formula (III) as repeating units, two, three or more of the groups of formula (III) can be contained in the oligomers or polymers. Generally, substances comprising 2 to 9 repeating units are referred to herein as oligomers, those comprising 10 and more repeating units as polymers. Thus, in the polymers containing a plurality of groups of formula (III) as repeating units, 10 or more groups of formula (III) may be present. It will be understood that the groups of formula (III) can have the same structure within a polymer or oligomer, or can have two or more different structures within the scope of formula (III). In some cases, the oligomers or polymers containing a plurality of groups of formula (III) as repeating units can be provided in the form of a library of sequence defined polymers which are prepared from different groups of formula (III) in a controlled, stepwise polymerization.

In line with formulae (II) and (III) above, an alkylene amine unit may be repeated once in an alternating chain such that oligo(alkylene amine) moieties of the type —S-L-L-S— or -L-S—S-L may result, wherein S represents a shorter ethylene amine unit, and L represents a longer alkylene amine unit. In some cases, groups of formula (II) and (III) are those wherein no repetition occurs, i.e., wherein p is 1, such that the shorter or longer units do not appear in pairs.

The group of formula (II) can be an oligo(alkylene amine) group of formula (IIa) and the group of formula (III) can be an oligo(alkylene amine) group of (IIIa):

$$-NR^2\{CH_2-(CH_2)_a-NR^3-CH_2-(CH_2)_b-NR^4\}_m-[CH2\text{-}(CH_2)_a-NR^5]_n-R^6 \quad \text{(IIa)},$$

wherein a, b, m, n, and $R^2$ to $R^6$ are defined as in formula (II), and wherein one or more of the nitrogen atoms indicated in formula (IIa) may be protonated to provide a cationic oligomer or polymer structure;

$$-NR^2\{CH_2-(CH_2)_a-NR^3-CH_2-(CH_2)_b-NR^4\}_m-[CH_2-(CH_2)_aNR^5]_n- \quad \text{(IIIa)},$$

wherein a, b, m, n, and $R^2$ to $R^5$ are defined as in formula (III), and wherein one or more of the nitrogen atoms indicated in formula (IIia) can be protonated to provide a cationic oligomer or polymer structure.

Moreover, in some cases, the oligo(alkylene amine) group of formulae (II) and (III) can have an n of 1. In some cases, m is 1 and n is 1. In some cases, the group of formula (II) is an oligo(alkylene amine) group of formula (IIb), and the group of formula (III) is an oligo(alkylene amine) group of formula (IIIb):

$$-NR^2-CH_2-(CH_2)_a-NR^3-CH_2-(CH_2)_b-NR^4-CH_2-(CH_2)_a-(NR^5)-R^6 \quad \text{(IIb)},$$

wherein a, b, and $R^2$ to $R^6$ are defined as in formula (II), and wherein one or more of the nitrogen atoms indicated in formula (IIb) can be protonated to provide a cationic oligomer or polymer structure;

$$-NR^2-CH_2-(CH_2)_a-NR^3-CH_2-(CH_2)_b-NR^4-CH_2-(CH_2)_a-NR^5- \quad \text{(IIIb)}$$

wherein a, b, and $R^2$ to $R^5$ are defined as in formula (III) and wherein one or more of the nitrogen atoms indicated in formula (IIIb) can be protonated to provide a cationic oligomer or polymer structure.

With respect to the length of the alkylene amine units in the oligo(alkylene amine) groups of formula (II), (IIa), (IIb) and (III), (IIIa), (IIIb), one of the alternating units can be an ethylene amine unit (i.e., either a orb is 1). The other alternating unit can be a propylene amine unit, a butylene amine unit or a pentylene amine unit (i.e., the other one of a or b can be an integer from 2 to 4. In some cases, the other of a orb can be 2 or 3, and in some cases, a is 1 and b is 2, or a is 2 and b is 1. In some cases, an oligo(alkylene amine) group of formula (IIc) is employed instead of or in addition to group (II), and/or an oligo(alkylene amine) group of formula (IIIc) is employed instead of or in addition to group (III). The formulae of group (IIc) and group (IIIc) are as follows:

$$-NR^2-CH_2-CH_2-NR^3-CH_2-CH_2-CH_2-NR^4-CH_2-CH_2-NR^5-R^6 \quad \text{(IIc)},$$

wherein $R^2$ to $R^6$ are as defined in formula (II), and wherein $R^2$ to $R^6$ are hydrogen, and wherein one or more of the nitrogen atoms indicated in formula (IIc) can be protonated to provide a cationic oligomer or polymer structure;

$$-NR^2-CH_2-CH_2-NR^3-CH_2-CH_2-CH_2-NR^4-CH_2-CH_2-NR^5- \quad \text{(IIIc)},$$

wherein $R^2$ to $R^5$ are as defined in formula (III), and wherein one or more of the nitrogen atoms indicated in formula (IIIc) can be protonated to provide a cationic oligomer or polymer structure.

In some cases, the groups $R^2$ to $R^6$ in formula (II), (IIa), (IIb) and (IIc) or the groups $R^2$ to $R^5$ in formula (III), (IIIa), (IIIb) and (IIIc) can be protecting group for an amino group. Non-limiting examples of protecting groups include t-butoxycarbonyl (Boc), 9-fluorenylmethoxycarbonyl (Fmoc), or carbobenzyloxy (Cbz).

In some cases, the groups $R^1$ to $R^6$ in formula (II), (IIa), (IIb) and (IIIc) or the groups $R^2$ to $R^5$ in formula (III), (IIIa), (IIIb) and (IIIc) are a receptor ligand, such as the receptor ligands described in Philipp and Wagner in "Gene and Cell Therapy—Therapeutic Mechanisms and Strategy", 3rd Edition, Chapter 15, CRC Press, Taylor & Francis Group LLC, Boca Raton 2009. Examples of receptor ligands that target the lung tissue are described in Pfeifer et al. 2010, Ther. Deliv. 1 (1): 133-48. Receptor ligands can include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that may bind to cell surface molecules (e.g., cell surface receptors), etc.

As far as any of the groups $R^1$ to $R^6$ in formula (II), (IIa), (IIb) and (IIc) or the groups $R^2$ to $R^5$ in formula (III), (IIIa), (IIIb) and (IIIc) are a poly(ethylene glycol) chain, the molecular weight of the poly(ethylene glycol) chain can be from about 100 g/mol to 20,000 g/mol, from about 1,000 g/mol to 10,000 g/mol or from about 1,000 g/mol to 5,000 g/mol.

In some cases, group (II) can be an oligo(alkylene amine) group of formula (IId):

$$-NH-CH_2-CH_2-NH-CH_2-CH_2-CH_2-NH-CH_2-CH_2-NH-H \quad \text{(IId)},$$

wherein one or more of the nitrogen atoms indicated in formula (IId) may be protonated to provide a cationic polymer or dendrimer structure. In some cases, group (III) is an oligo(alkylene amine) group of formula (IIId):

$$-NH-CH_2-CH_2-NH-CH_2-CH_2-CH_2-NH-CH_2-CH_2-NH- \quad \text{(IIId)}$$

wherein one or more of the nitrogen atoms indicated in formula (IIId) may be protonated to provide a cationic polymer or dendrimer structure.

Lipidoids

An engineered polyribonucleotide can be encapsulated in a lipidoid formulation. A lipidoid formulation can be any material that has characteristics of a lipid, such as fats, waxes, sterols, fat-soluble vitamins (such as vitamins A, D, E, and K), monoglycerides, diglycerides, triglycerides, phospholipids, and others. For example, a lipid or lipidoid formulation can include lipids such as cholesterol, DOPE, DOPC or DSPC which are referred to as helper lipids in the scientific literature, and/or PEGylated lipids or any other lipid useful for preparing lipoplexes. The formulation comprising the engineered polyribonucleotide may be a nanoparticle which may comprise at least one lipid. A lipidoid formulation can be a lipid nanoparticle. The lipid may be selected from, but is not limited to, DOPE, DOPC, DSPC, cholesterol, DLin-DMA, DLin-K-DMA, 98N12-5, C12-200, DLin-MC3-DMA, DLin-KC2-DMA, DODMA, PLGA, PEG, PEG-DMG and PEGylated lipids. In another aspect, the lipid may be a cationic lipid such as, but not limited to, DLin-DMA, DLin-D-DMA, DLin-MC3-DMA, DLin-KC2-DMA and DODMA.

The composition containing a lipidoid may be about 40-60% lipidoid, about 40-60% cholesterol, and about 5-20% PEG-lipid (in percent by weight, based on the total weight of the composition). The composition containing a lipidoid may be about 50-60% lipidoid, about 40-50% cholesterol, and about 5-10% PEG-lipid. The composition containing a lipidoid may be about 50-75% lipidoid, about 20-40% cholesterol, and about 1-10% PEG-lipid. The composition containing a lipidoid may be about 60-70% lipidoid, about 25-35% cholesterol, and about 5-10% PEG-lipid. The composition may be provided with techniques described in, for example, Akinc et al, 2007, Nat Biotech, 26, 561-569; Akinc et al, 2009, Mol Ther, 17, 872-9; Love et al, 2010, PNAS, 107, 1864-9; U.S. Pat. No. 8,450,298, O2006/138380). RNA/lipidoid complexes may form particles that are useful in the delivery of RNA, such as single-stranded RNAs or mRNAs, into cells.

A composition of the disclosure cab be an engineered polyribonucleotide encapsulated by a lipidoid of formula (IV)

$$R^1—NR^2\{CH_2—(CH_2)_a—NR^3—[CH_2—(CH_2)_b—NR^4]_p\}_m—[CH_2—(CH_2)_a—NR^5]_n—R^6 \quad (IV),$$

wherein the variables a, b, p, m, n and R1 to R6 are defined as follows:

a is 1 and b is an integer of 2 to 4; or a is an integer of 2 to 4 and b is 1, p is 1 or 2, m is 1 or 2; n is 0 or 1 and m+n is 2; and $R^1$ to $R^6$ are independently of each other selected from hydrogen; a group $—CH_2—CH(OH)—R^7$, $—CH(R^7)—CH_2—OH$, $—CH_2—CH_2—(C{=}O)—O—R^7$, $—CH_2—CH_2—(C{=}O)—NH—R^7$ or $—CH_2—R^7$ wherein $R^7$ is selected from C3-C18 alkyl or C3-C18 alkenyl having one C—C double bond; a protecting group for an amino group; $—C(NH)—NH_2$; a poly (ethylene glycol) chain; and a receptor ligand; provided that at least two residues among $R^1$ to $R^6$ are a group $—CH_2—CH(OH)—R^7$, $—CH(R^7)—CH_2—OH$, $—CH_2—CH_2—(C{=}O)—O—R^7$, $—CH_2—CH_2—(C{=}O)$ 13 $NH—R^7$ or $—CH_2—R^7$ wherein $R^7$ is selected from C3-C18 alkyl or C3-C18 alkenyl having one C—C double bond.

In some cases, $R^1$ to $R^6$ are independently selected from hydrogen; a group $—CH_2—C(OH)H—R^7$ or $—CH(R^7)—CH_2—OH$, wherein $R^7$ is selected from C3-C18 alkyl or C3-C18 alkenyl having one C—C double bond; a protecting group for an amino group; and a poly(ethylene glycol) chain; provided that at least two residues among R' to $R^6$ are a group $—CH2\text{-}C(OH)H—R^7$ or $—CH(R^7)—CH_2—OH$, wherein $R^7$ is selected from C3-C18 alkyl or C3-C18 alkenyl having one C—C double bond. In some cases, $R^1$ to $R^6$ are independently selected from hydrogen; and a group $—CH_2—CH(OH)—R^7$ or $—CH(R^7)—CH_2—OH$ wherein $R^7$ is selected from C3-C16 alkyl or C3-C16 alkenyl having one C—C double bond; provided that at least two residues among $R^1$ to $R^6$ are a group $—CH_2—CH(OH)—R^7$ or $—CH(R^7)—CH_2—OH$, wherein $R^7$ is selected from C3-C18 alkyl or C3-C18 alkenyl having one C—C double bond. In some cases, $R^1$ and $R^6$ are independently selected from hydrogen; and a group $—CH_2—CH(OH)—R^7$ or $—CH(R^7)—CH2\text{-}OH$ wherein $R^7$ is selected from C3-C18 alkyl or C3-C18 alkenyl having one C—C double bond; and $R^2$ to $R^5$ are all a group $—CH2\text{-}CH(OH)—R^7$ or $—CH(R^7)—CH_2—OH$ wherein $R^7$ is selected from C3-C18 alkyl or C3-C18 alkenyl having one C—C double bond. In some cases, $R^7$ is selected from C8-C16 alkyl or C8-C18 alkenyl having one C—C double bond, or from C8-C12 alkyl or C8-C12 alkenyl having one C—C double bond, or from C10-C12 alkyl or C10-C12 alkenyl having one C—C double bond.

One or more of the nitrogen atoms indicated in formula (IV) may be protonated to provide a cationic lipidoid of formula (IV).

In line with formula (IV) above, an alkylene amine unit may be repeated once in an alternating chain such that oligo(alkylene amine) moieties of the type —S-L-L-S— or -L-S—S-L- may result, wherein S represents a shorter ethylene amine unit, and L represents a longer alkylene amine unit. In some cases, a lipidoid of formula (IV) is one wherein no repetition occurs, i.e., wherein p is 1, such that the shorter or longer units do not appear in pairs. The lipidoid of formula (IV) can be a lipidoid of (IVa):

$$R^1—NR^2\{CH_2—(CH_2)_a—NR^3—CH_2—(CH_2)_b—NR\}_m—[CH_2—(CH_2)_a—NR^5]_n—R^6 \quad (IVa),$$

wherein a, b, m, n, and $R^1$ to $R^6$ are defined as in formula (IV) and wherein one or more of the nitrogen atoms indicated in formula (IVa) may be protonated to provide a cationic lipidoid;

In some cases, the lipidoid is a lipidoid of formula (IV). In some cases 'n' is 1 in a lipidoid of formula (IV). In some cases, 'm' is 1 and n is 1 in a lipidoid of formula (IV). In some cases, the lipidoid of formula (IV) is a lipidoid of formula (IVb):

$$R—NR^2—CH_2—(CH_2)_a—NR^3—CH_2—(CH_2)_b—NR^4—CH_2—(CH_2)_a—NR^5—R^6 \quad (IVb),$$

wherein a, b, and $R^1$ to $R^6$ are defined as in formula (IV) wherein one or more of the nitrogen atoms indicated in formula (IVb) may be protonated to provide a cationic lipidoid.

As regards the length of the alkylene amine units in the lipidoid of formula (IV), (IVa) and (IVb), it will be understood that one of the alternating units needs to be an ethylene amine unit (i.e., either a or b is 1). The other alternating unit can be a propylene amine unit, a butylene amine unit, a pentylene amine unit, or another suitable unit (i.e., the other one of a or b is an integer of 2 to 4. In some cases, a lipidoid of formula (N) is a lipidoid of formula (IVc):

$$R^1—NR^2—CH_2—CH_2—NR^3—CH_2—CH_2—CH_2—NR^4—CH_2—CH_2—NR^5—R^5 \quad (IVc)$$

wherein $R^1$ to $R^6$ are as defined in formula (IV) and wherein one or more of the nitrogen atoms indicated in formula (IVc) can be protonated to provide a cationic lipidoid;

In some cases, the groups $R^1$ to $R^6$ in formula (IV), (IVa), (IVb) and (IVc) are a protecting group for an amino group. Non-limiting examples of protecting groups include t-butoxycarbonyl (Boc), 9-fluorenylmethoxycarbonyl (Fmoc), or carbobenzyloxy (Cbz).

As far as the groups $R^1$ to $R^6$ in formula (IV), (IVa), (IVb) and (IVc) are a receptor ligand, such as the receptor ligands described in Philipp and Wagner in "Gene and Cell Therapy—Therapeutic Mechanisms and Strategy", 3rd Edition, Chapter 15, CRC Press, Taylor & Francis Group LLC, Boca Raton 2009. Examples of receptor ligands that target the lung tissue are described in Pfeifer et al. 2010, Ther. Deliv. 1 (1): 133-48. Receptor ligands can include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that may bind to cell surface molecules (e.g., cell surface receptors), etc.

As far as the groups $R^1$ to $R^6$ in formula (IV), (IVa), (IVb) and (IVc) are a poly(ethylene glycol) chain, the molecular weight of the poly(ethylene glycol) chain can be from about 100 g/mol to 20,000 g/mol, from about 1,000 g/mol to 10,000 g/mol or from about 1,000 g/mol to 5,000 g/mol. In some cases, a molecular weight of the PEG chain can provide a composition with a desired density.

Multiple lipidoid molecules can be associated with an engineered polyribonucleotide. For example, a composition can comprise 1 engineered polyribonucleotide to 100 lipidoid molecules, 1 engineered polyribonucleotide to 1,000 lipidoid molecules, 10 engineered polyribonucleotide to 1,000 lipidoid molecules, or 100 engineered polyribonucleotide to 10,000 lipidoid molecules. The complex of engineered polyribonucleotide and lipidoid can form a particle. The diameter of the particles may range, e.g., from 10 nanometers to 1,200 nanometers. In some cases the diameter of the particles ranges from 10 nanometers to 500 nanometers. In some cases, the diameters of the particles are from 20 nanometers to 150 nanometers.

Administration to a Subject

Further described herein are methods for the administration of a polynucleotide (e.g., polyribonucleotide) to a subject. The polyribonucleotide can be provided to the subject via a delivery agent, such as a particle or capsule with an encapsulating agent that encapsulates the polyribonucleotide. The delivery agent can be a therapeutic agent. The subject can be a human, such as a human afflicted with cancer. The delivery agent can be administered to the subject (e.g., self-administration or administration by a third party, such as a healthcare provider) at a given dosage, and the dosage can be increased with time, decreased with time, or kept constant. The dosage can be changed based on a progression or regression of a disease in the subject, such as a rare disease or a cancer.

A polyribonucleotide of the disclosure can be formulated with one or more pharmaceutically acceptable carrier(s) to be administered to a subject. In some cases, the polyribonucleotide can be formulated for targeted delivery to a target cell or cell population. In some cases, the polyribonucleotide can be formulated for untargeted delivery to a cell or cell population. The encoded polypeptide product of the polyribonucleotide is then transcribed and it accumulates within the recipient cell.

A composition can be a combination of any engineered polyribonucleotide described herein with other chemical components, such as carriers, stabilizers, diluents, dispersing agents, suspending agents, thickening agents, and/or excipients. The composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For administration by inhalation, the active compounds can be in a form as an aerosol, a mist, a vapor, a spray, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The eye comprises several structurally and functionally distinct vascular beds that supply ocular components critical to the maintenance of vision. These beds include the retinal and choroidal vasculatures, which supply the inner and outer portions of the retina, respectively, and the limbal vasculature located at the periphery of the cornea.

A pharmaceutical composition comprising an engineered polyribonucleotide can be administered to the eye via any suitable form or route including, for example, topical, oral, systemic, intravitreal, intracameral, subconjunctival, subtenon, retrobulbar, intraocular, posterior juxtascleral, periocular, subretinal, and suprachoroidal administration. The compositions can be administered by injecting the formulation in any part of the eye including anterior chamber, posterior chamber, vitreous chamber (intravitreal), retina proper, and/or subretinal space. The compositions can also be delivered via a non-invasive method. Non-invasive modes of administering the formulation can include using a needleless injection device. Multiple administration routes can be employed for efficient delivery of the pharmaceutical compositions.

An engineered polynucleotide of the disclosure can be delivered to any suitable ocular cell including for example, endothelial cells such as vascular endothelial cells, cells of the retina such as retinal pigment epilthelium (RPE), corneal cells, fibroblasts, astrocytes, glial cells, pericytes, iris epithelial cells, cells of neural origin, ciliary epithelial cells, mueller cells, muscle cells surrounding and attached to the eye such as cells of the lateral rectus muscle, orbital fat cells, cells of the sclera and episclera, cells of the trabecular meshwork, and connective tissue cells.

A composition that is disclosed herein, upon administration to a subject, can have a transfection efficiency of at least about 80%, 90%, or 95% by the cell of the subject. In some cases, the transfection efficiency of an encapsulated composition, upon administration to a subject, is at least about 50%, 60%, 70%, 80%, 90%, 95%, 100%, 110%, 120%, 130%, 140%, 150%, 160%, 170%, 180%, 190%, 200%, 225%, 250%, 275%, 300%, 325%, 350%, 375%, 400%, 450%, or 500% relative to an unencapsulated polyribonucleotide. In some situations, transfection efficiency of a composition comprising a modified polyribonucleotide (in some cases also comprising an unmodified polyribonucleotide), upon administration to a subject, is at least about 50%, 60%, 70%, 80%, 90%, 95%, 100%, 110%, 120%, 130%, 140%, 150%, 160%, 170%, 180%, 190%, 200%, 225%, 250%, 275%, 300%, 325%, 350%, 375%, 400%, 450%, or 500% relative to composition solely containing an unmodified polyribonucleotide. The transfection efficiency of a composition can be increased by addition of a carrier, such as a cell penetrating peptide or a cationic coating to the outer layer of the composition. The transfection efficiency of a composition can be modulated by the density of a composition.

Methods for the preparation of compositions comprising the engineered polyribonucleotides described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999), each of which is incorporated by reference in its entirety.

A composition comprising a polynucleotide (e.g., polyribonucleotide) can be provided in various dosages. A dose of a polynucleotide, or a polyribonucleotide, can be from about 1 μg to about 1000 μg, about 1 μg to about 500 μg, about 1 μg to about 1000 μg, about 10 μg to about 500 μg, about 20 μg to about 500 μg, about 25 μg to about 500 μg, about 30 μg to about 500 μg, about 40 μg to about 500 μg, about 50 μg to about 500 μg, about 10 μg to about 250 μg, about 20 μg to about 250 μg, about 30 μg to about 250 μg, about 40 μg to about 250 μg, about 50 μg to about 250 μg, about 1 μg to about 200 μg, about 10 μg to about 200 μg, about 20 μg to about 200 μg, about 30 μg to about 200 μg, about 40 μg to about 200 μg, about 50 μg to about 200 μg, about 25 μg to about 50 μg, about 25 μg to about 100 μg, about 25 μg to about 150 μg, about 25 μg to about 200 μg, about 25 μg to about 250 μg, about 25 μg to about 300 μg, about 25 μg to about 350 μg, about 25 μg to about 400 μg, about 25 μg to about 450 μg, about 25 μg to about 500 μg, about 50 μg to about 750 μg, or about 25 μg to about 1000 μg of the engineered polyribonucleotide. In some cases, a dose of a polynucleotide is about 1 mg to about 100 mg, about 1 mg to about 50 mg, about 10 mg to about 50 mg, about 20 mg to about 50 mg, about 25 mg to about 50 mg, about 30 mg to about 50 mg, about 40 mg to about 50 mg, about 50 mg to about 100 mg, about 1 mg to about 25 mg, about 2 mg to about 25 mg, about 3 mg to about 25 mg, about 4 mg to about 25 mg, about 5 mg to about 25 mg, about 1 mg to about 20 mg, about 1 mg to about 20 mg, about 2 mg to about 20 mg, about 3 mg to about 20 mg, about 4 mg to about 20 mg, or about 5 mg to about 20 mg of an engineered polyribonucleotide.

The percentage of a polyribonucleotide in a formulation (e.g., within an encapsulated agent) can be greater than or equal to 0.25% polyribonucleotide, 0.5% polyribonucleotide, 0.75% polyribonucleotide, 1% polyribonucleotide, 1.25% polyribonucleotide, 1.5% polyribonucleotide, 1.75% polyribonucleotide, 2% polyribonucleotide, 2.25% polyribonucleotide, 2.5% polyribonucleotide, 2.75% polyribonucleotide, 3% polyribonucleotide, 3.25% polyribonucleotide, 3.5% polyribonucleotide, 3.75% polyribonucleotide, 4% polyribonucleotide, 4.25% polyribonucleotide, 4.5% polyribonucleotide, 4.75% polyribonucleotide, 5% polyribonucleotide, 5.25% polyribonucleotide, 5.5% polyribonucleotide, 5.75% polyribonucleotide, 6% polyribonucleotide, 6.25% polyribonucleotide, 6.5% polyribonucleotide, 6.75% polyribonucleotide, 7% polyribonucleotide, 7.25% polyribonucleotide, 7.5% polyribonucleotide, 7.75% polyribonucleotide, 8% polyribonucleotide, 8.25% polyribonucleotide, 8.5% polyribonucleotide, 8.75% polyribonucleotide, 9% polyribonucleotide, 9.25% polyribonucleotide, 9.5% polyribonucleotide, 9.75% polyribonucleotide, 10% polyribonucleotide, 10.25% polyribonucleotide, 10.5% polyribonucleotide, 10.75% polyribonucleotide, 11% polyribonucleotide, 11.25% polyribonucleotide, 11.5% polyribonucleotide, 11.75% polyribonucleotide, 12% polyribonucleotide, 12.25% polyribonucleotide, 12.5% polyribonucleotide, 12.75% polyribonucleotide, 13% polyribonucleotide, 13.25% polyribonucleotide, 13.5% polyribonucleotide, 13.75% polyribonucleotide, 14% polyribonucleotide, 14.25% polyribonucleotide, 14.5% polyribonucleotide, 14.75% polyribonucleotide, 15% polyribonucleotide, 15.25% polyribonucleotide, 15.5% polyribonucleotide, 15.75% polyribonucleotide, 16% polyribonucleotide, 16.25% polyribonucleotide, 16.5% polyribonucleotide, 16.75% polyribonucleotide, 17% polyribonucleotide, 17.25% polyribonucleotide, 17.5% polyribonucleotide, 17.75% polyribonucleotide, 18% polyribonucleotide, 18.25% polyribonucleotide, 18.5% polyribonucleotide, 18.75% polyribonucleotide, 19% polyribonucleotide, 19.25% polyribonucleotide, 19.5% polyribonucleotide, 19.75% polyribonucleotide, 20% polyribonucleotide, 20.5% polyribonucleotide, 21% polyribonucleotide, 21.5% polyribonucleotide, 22% polyribonucleotide, 22.5% polyribonucleotide, 23% polyribonucleotide, 23.5% polyribonucleotide, 24% polyribonucleotide, 24.5% polyribonucleotide, or 25% polyribonucleotide by weight. Alternatively, the percentage of the polyribonucleotide in the formulation (e.g., within an encapsulated agent) can be less than about 25% polyribonucleotide, 24.5% polyribonucleotide, 24% polyribonucleotide, 23.5% polyribonucleotide, 23% polyribonucleotide, 22.5% polyribonucleotide, 22% polyribonucleotide, 21.5% polyribonucleotide, 21% polyribonucleotide, 20.5% polyribonucleotide, 20% polyribonucleotide, 19.5% polyribonucleotide, 19% polyribonucleotide, 18.5% polyribonucleotide, 18% polyribonucleotide, 17.5% polyribonucleotide, 17% polyribonucleotide, 16.5% polyribonucleotide, 16% polyribonucleotide, 15.5% polyribonucleotide, 15% polyribonucleotide, 14.5% polyribonucleotide, 14% polyribonucleotide, 13.5% polyribonucleotide, 13% polyribonucleotide, 12.5% polyribonucleotide, 12% polyribonucleotide, 11.5% polyribonucleotide, 11% polyribonucleotide, 10.5% polyribonucleotide, 10% polyribonucleotide, 9.5% polyribonucleotide, 9% polyribonucleotide, 8.5% polyribonucleotide, 8% polyribonucleotide, 7.5% polyribonucleotide, 7% polyribonucleotide, 6.5% polyribonucleotide, 6% polyribonucleotide, 5.5% polyribonucleotide, 5% polyribonucleotide, 4.5% polyribonucleotide, 4% polyribonucleotide, 3.5% polyribonucleotide, 3% polyribonucleotide, 2.5% polyribonucleotide, 2% polyribonucleotide, 1.5% polyribonucleotide, 1% polyribonucleotide, 0.5% polyribonucleotide, or 0.1% polyribonucleotide.

In some cases, an encapsulated composition of the disclosure can produce a plasma, serum or blood concentration of the polyribonucleotide, pharmaceutical carrier, encapsulating agent, or polymeric material (e.g.: polyethylene glycol or polyethyenimine) in a subject within about 1 second to about 30 minutes, about 1 second to 20 minutes, about 1 second to 10 minutes, about 1 second to 5 minutes, about 1 second to 2 minutes, about 1 second to 1 minute, about 1 second to about 30 seconds, about 30 seconds to 30 minutes, about 30 seconds to 20 minutes, about 30 seconds to 10 minutes, about 30 seconds to 5 minutes, about 30 seconds to 2 minutes, about 30 seconds to about 1 minute, about 1 minute to about 30 minutes, about 1 minute to about 25 minutes, about 1 minute to about 20 minutes, about 1 minute to about 15 minutes, about 1 minute to about 10 minutes, about 5 minutes to about 30 minutes, about 5 minutes to about 25 minutes, about 5 minutes to about 20 minutes, about 5 minutes to about 15 minutes, about 5 minutes to about 10 minutes, about 10 minutes to about 30 minutes, about 10 minutes to about 25 minutes, about 10 minutes to about 20 minutes, or about 10 minutes to about 15 minutes of use of the device. The plasma, serum or blood concentration of the polyribonucleotide, pharmaceutical carrier, encapsulating agent, or polymeric material (e.g.: polyethylene glycol or polyethyenimine) concentration can be a peak concentration or an average concentration.

Treatments and Conditions

The methods, polyribonucleotides, and pharmaceutical compositions of this disclosure provide a method to treat a condition. The treatment may comprise treating a subject (e.g., a patient with a disease and/or a lab animal with a condition). In some cases the condition is a cancer. In some cases, the condition is lung cancer. In some cases, the condition is breast cancer. In some cases, the subject is a human. Treatment may be provided to the subject before clinical onset of disease. Treatment may be provided to the subject after clinical onset of disease. Treatment may be provided to the subject on or after 1 minute, 5 minutes, 10 minutes, 30 minutes, 1 hour, 2 hours, 3 hours, 4 hours, 5 hours, 6 hours, 12 hours, 1 day, 1 week, 6 months, 12 months, or 2 years after clinical onset of the disease. Treatment may be provided to the subject for a time period that is greater than or equal to 1 minutes, 10 minutes, 30 minutes, 1 hours, 2 hours, 3 hours, 4 hours, 5 hours, 6 hours, 12 hours, 1 day, 1 week, 1 month, 6 months, 12 months, 2 years or more after clinical onset of the disease. Treatment may be provided to the subject for a time period that is less than or equal to 2 years, 12 months, 6 months, 1 month, 1 week, 1 day, 12 hours, 6 hours, 5 hours, 4 hours, 3 hours, 2 hours, 1 hour, 30 minutes, 10 minutes, or 1 minute after clinical onset of the disease. Treatment may also include treating a human in a clinical trial.

Compositions containing the engineered polyribonucleotides described herein can be administered for prophylactic and/or therapeutic treatments. In therapeutic applications, the engineered polyribonucleotides can be administered to a subject already suffering from a disease, such as a lung or a breast cancer, in the amount sufficient to provide the amount of the encoded polyribonucleotide that cures or at least improves the symptoms of the disease. Engineered polyribonucleotides can also be administered to lessen a likelihood of developing, contracting, or worsening a disease. Amounts effective for this use can vary based on the severity and course of the disease or condition, the efficiency of transfection of an engineered polynucleotide, the affinity of an encoded polypeptide to a target molecule, previous therapy, the subject's health status, weight, response to the drugs, and the judgment of the treating physician.

The polyribonucleotides of the disclosure can be used, for example, to treat a condition associated with a defect or malfunction of a gene in the ATP-binding cassette (ABC) family. Non-limiting examples of conditions associated with a gene in the ATP-binding cassette (ABC) family include: age-related macular degeneration, benign recurrent intrahepatic cholestasis, Cantu syndrome, congenital bilateral absence of the vas deferens, congenital hyperinsulinism, cystic fibrosis, Dubin-Johnson syndrome, familial dilated cardiomyopathy, familial HDL deficiency, generalized arterial calcification of infancy, harlequin ichthyosis, hereditary pancreatitis, intrahepatic cholestasis of pregnancy, lamellar ichthyosis, permanent neonatal diabetes mellitus, progressive familial intrahepatic cholestasis, pseudoxanthoma elasticum, retinitis pigmentosa, sitosterolemia, Stargardt macular degeneration, surfactant dysfunction, Tangier disease, X-linked adrenoleukodystrophy, X-linked sideroblastic anemia and ataxia.

A polyribonucleotide, a method, and a pharmaceutical composition of the disclosure can be used, for example, to treat a cancer. Non-limiting examples of cancers can include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenstrom macroglobulinemia, and Wilms tumor. In some cases, an engineered polyribonucleotide is administered to a subject to treat a lung cancer. In some cases, an engineered polyribonucleotide is administered to a subject to treat a breast cancer.

In some cases, a polynucleotide of the disclosure can encode a polypeptide that is at least 80% homologous to a protein of the ATP-binding cassette, sub-family A, such as ABCA3.

Multiple engineered polyribonucleotides can be administered in any order or simultaneously. The engineered polyribonucleotides can be packed together or separately, in a single package comprising polyribonucleotides that target the same target molecule or in a plurality of packages. One or all of the engineered polyribonucleotides can be given in multiple doses. If not simultaneous, the timing between the multiple doses may vary.

The engineered polyribonucleotides can be administered to a subject as soon as possible after the onset of the symptoms. An engineered polyribonucleotides can be administered as soon as is practical after the onset of a disease or condition is detected or suspected, and for a length of time necessary for the treatment of the disease, such as, for example, for about 1 month, for about 6 months, for about 12 months, for about 18 months, for about 24 months, or any appropriate length of time. The length of treatment can vary for each subject.

EXAMPLES

Example 1: Formulation of a Composition Comprising an Engineered Polyribonucleotide for the Treatment of Human Subjects Afflicted with a Lung Disorder Compositions are formulated as follows:

An engineered polynucleotide encoding the ABCA3 gene sequence, NCBI Reference Sequence: NM_001089.2, is prepared as described by WO2011012316, WO2014207231, WO2014153052, WO2013185069. Branched polyethylenimine (PEI, average MW=25 kDa) is purchased from Sigma-Aldrich™ (Schnelldorf, Germany) and used without further purification. PEI is diluted in endotoxin free water and adjusted to pH 7.4 with HCl. Endotoxin free water is purchased from B. Braun (Melsungen, Germany).

The engineered polyribonucleotide and PEI can be diluted in 4.0 ml of double distilled water resulting in concentrations of 250 μg/ml mRNA and 326.3 μg/ml PEI, respectively (roughly at a polynucleotide to PEI ratio of 10). The engineered polyribonucleotide solution can be pipetted into the PEI solution, mixed by pipetting up and down, to yield a final polyribonucleotide concentration of 125 μg/ml. The complexes can be incubated for 20 min at room temperature prior to being administered to a subject.

Example 2: Design, Synthesis, Formulation, and Cell-Based Characterization of Engineered Polyribonucleotides for the Synthesis of Human ABCA3

Eight different versions of Engineered Polyribonucleotides encoding variations of the human ABCA3 are prepared comprising the following sequences

TABLE 7

| |
|---|
| Native ORF alone (no UTRs) |
| Native ORF + native UTRs |
| Native ORF + CYBA UTRs |
| Native ORF + α-globin 5' UTR ETH |
| Codon-optimized ORF |
| Codon-optimized ORF + native UTRs |
| Codon optimized native ORF + CYBA UTRs |
| Codon-optimized ORF + UTR-ETH |

The constructs are sub-cloned into a vector and amplified with standard procedures (e.g.: maxi prep). The nucleic acid sequence of each construct is confirmed with sequencing techniques.

Example 3: Expression of Engineered Polyribonucleotides in Human Alveolar Epithelial Cell Lines Different constructs expressing the sequences described in TABLE 6 are administered to the human alveolar epithelial cell lines A549, HepG2, and HEK293 cells. Each construct is incorporated into a formulation comprising an N/P ratio of about 8 (N/P=the ratios of moles of the amine groups of cationic polymers to those of the phosphate ones of DNA). Examples of formulations and the molar ratio of the components are shown in TABLE 8.

TABLE 8

| Formulation | Cationic Lipid | DPPC | Cholesterol | DMG-PEG2000 |
|---|---|---|---|---|
| Formulation 1 | 40% dL_01 and 60% dL_05 | 5.29 | 4.41 | 0.88 |
| Formulation 2 | 60% dL_01 and 40% dL_05 | 5.29 | 4.41 | 0.88 |
| Formulation 3 | 100% dL_05 | 5.29 | 4.41 | 0.88 |
| Formulation 4 | 100% dL_01 | 5.29 | 4.41 | 0.88 |

As used herein dL_01 is

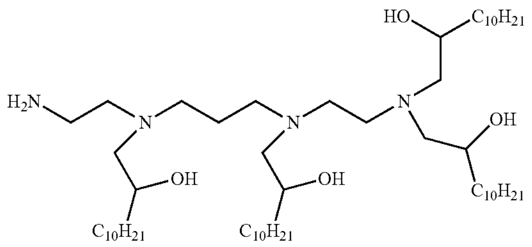

As used herein dL_05 is

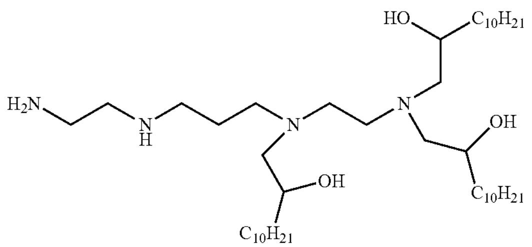

The polyplex size and the zeta potential of each formulation is measured. The stability of each formulation is measured at various pHs, temperatures and after vigorous shaking.

The half-life, RNA uptake, and immunogenicity of each polyribonucleotide formulation is measured in all three lung epithelial cell lines (A549, HepG2 and HEK293).

Example 4: Uptake, Expression and Distribution of an Engineered Polyribonucleotide Encoding a Reporter Gene Engineered polyribonucleotides encoding a firefly luciferase (FFL, 1.64 kb), a Tomato Red (TR, 1.86 kb), an Enhanced Green Fluorescent Protein (EGFP, 0.94 kb), and a LacZ (3.3 kb) reporter. This study also describes a comparison between polyethyleneimine ("PEI") and EPE (a statistical polymer of aminoethyl and aminopropyl units; see EP-A13034539, which is incorporated by reference herein) formulations, cellular distribution (e.g., alveolar type II epithelial cells, alveolar type I epithelial cells, pulmonary microvascular endothelial cells) and variability in dose ranges for optimal uptake, expression and distribution of different engineered polyribonucleotides encoding a reporter gene. TABLE 9 illustrates different dosing regimens that are tested in a mouse model.

TABLE 9

| Group # | Engineered Polyribonucleotides | Dose * | Dosing Regimen | N | Time Point |
|---|---|---|---|---|---|
| 1 | polyethyleneimine ("PEI") vehicle | — | Single Dose | 3 | 24 hours |
| 2 | EPE vehicle | — | Single Dose | 3 | 24 hours |
| 3 | PEI + FFL | 0.1 to 1 mg/kg | Single Dose | 3 | 24 hours |
| 4 | PEI + FFL | 1.0 to 10.0 mg/kg | Single Dose | 3 | 24 hours |
| 5 | EPE + FFL | 0.1 to 1 mg/kg | Single Dose | 3 | 24 hours |
| 6 | EPE + FFL | 1.0 to 10.0 mg/kg | Single Dose | 3 | 24 hours |
| 7 | PEI + Tomato Red | 0.1 to 1 mg/kg | Single Dose | 3 | 24 hours |
| 8 | PEI + Tomato Red | 1.0 to 10.0 mg/kg | Single Dose | 3 | 24 hours |
| 9 | EPE + Tomato Red | 0.1 to 1 mg/kg | Single Dose | 3 | 24 hours |
| 10 | EPE + Tomato Red | 1.0 to 10.0 mg/kg | Single Dose | 3 | 24 hours |
| 11 | PEI + EGFP | 0.1 to 1 mg/kg | Single Dose | 3 | 24 hours |
| 12 | PEI + EGFP | 1.0 to 10.0 mg/kg | Single Dose | 3 | 24 hours |
| 13 | EPE + EGFP | 0.1 to 1 mg/kg | Single Dose | 3 | 24 hours |
| 14 | EPE + EGFP | 1.0 to 10.0 mg/kg | Single Dose | 3 | 24 hours |
| 15 | PEI + LacZ | 0.1 to 1 mg/kg | Single Dose | 3 | 24 hours |
| 16 | PEI + LacZ | 1.0 to 10.0 mg/kg | Single Dose | 3 | 24 hours |
| 17 | EPE + LacZ | 0.1 to 1 mg/kg | Single Dose | 3 | 24 hours |
| 18 | EPE + LacZ | 1.0 to 10.0 mg/kg | Single Dose | 3 | 24 ours |

Route of administration: inhalation (aerosol). FIG. 1 illustrates an example of aerosol administration of engineered polyribonucleotides to mice. The experiment can be conducted in any mice, such as wild-type C57B16 mice. The expression of a firefly luciferase (FFL, 1.64 kb), a Tomato Red (TR, 1.86 kb), an Enhanced Green Fluorescent Protein (EGFP, 0.94 kb), and a LacZ (3.3 kb) reporter is measured in a total number of 54 mice.

Example 5: In Vivo Uptake, Expression and Distribution of an Engineered Polyribonucleotide Encoding an ABCA3 Protein A total of 36 wild-type C57B16 mice are administered one or more constructs comprising the polyribonucleotides of TABLE 7 prepared with one or more formulations listed in TABLE 8. An endotracheal tube is used as the route of administration.

Lung tissue of each mouse is collected about 24 hours after endotracheal administration of each peptide. The tissue of one lung per mouse is flash frozen and analyzed by qPCR, western blot, and ELISA for the expression of ABCA3 protein. The tissue of one lung per mouse is fixed in formalin and analyzed for in situ presence of the engineered polyribonucleotide and histological analysis. Bronchoalveolar Lavage Fluid (BALF) is collected and the expression levels of the markers IL-10, MIP-1α, INF-α, TNF-α, IL-12, and IL-6 are analyzed to determine the immunogenicity of each engineered polyribonucleotide.

Example 6: In Vivo Dosing Study of an Engineered Polyribonucleotide Encoding an ABCA3 Protein Wild-type C57B16 mice are administered one or more constructs comprising the polyribonucleotides of TABLE 7 prepared in one or more formulations listed in TABLE 8. An endotracheal tube is used to administer the engineered polyribonucleotides to each mouse. Different dosages of each engineered polyribonucleotide are tested, including dosages ranging from 0.1 mg/kg to 1 mg/kg and 1 mg/kg to 10 mg/kg.

Lung tissue of each mouse is collected about 24 hours after endotracheal administration of each peptide. The tissue of one lung per mouse is flash frozen and analyzed by qPCR, western blot, and ELISA for the expression of ABCA3 protein. The tissue of one lung per mouse is fixed in formalin and analyzed for in situ presence of the engineered polyribonucleotide and histological analysis. Bronchoalveolar Lavage Fluid (BALF) is collected and the expression levels of the markers IL-10, MIP-1α, INF-α, TNF-α, IL-12, and IL-6 are analyzed to determine the immunogenicity of each engineered polyribonucleotide.

The metrics determined from the lung and biological samples are used to evaluate the safety and efficacy of each dosage.

Example 7: In Vivo Dosing Study of an Engineered Polyribonucleotide Encoding an ABCA3 Protein Wild-type C57B16 mice repeatedly inhale an aerosol comprising one or more constructs with the polyribonucleotides listed in TABLE 7. Different dosages of each engineered polyribonucleotide are tested, including dosages ranging from 0.1 mg/kg to 1 mg/kg and 1 mg/kg to 10 mg/kg.

Different mice receive repeated dosages at 8 hours, 24 hours, 48 hours, 72 hours, 96 hours, and 120 hours after an initial dosage. Lung tissue and biological sample of different mice is collected about 8 hours, 24 hours, 48 hours, 72 hours, 96 hours, and 120 hours after administration of each peptide. At each specified time, the tissue of one lung per mouse is flash frozen and analyzed by qPCR, western blot, and ELISA for the expression of ABCA3 protein. The tissue of one lung per mouse is fixed in formalin and analyzed for in situ presence of the engineered polyribonucleotide and histological analysis. Bronchoalveolar Lavage Fluid (BALF) is collected and the expression levels of the markers IL-10, MIP-1α, INF-α, TNF-α, IL-12, and IL-6 are analyzed to determine the immunogenicity of each engineered polyribonucleotide. Blood, liver and spleen are also collected, flash frozen, and processed for histological analysis.

The metrics determined from the lung and biological samples are used to evaluate the safety and efficacy of repeated administrations of aerosolized engineered polyribonucleotides.

Example 8: Expression of ABCA3 Ribonucleic Acid in Mammalian Cells

Figure 2:
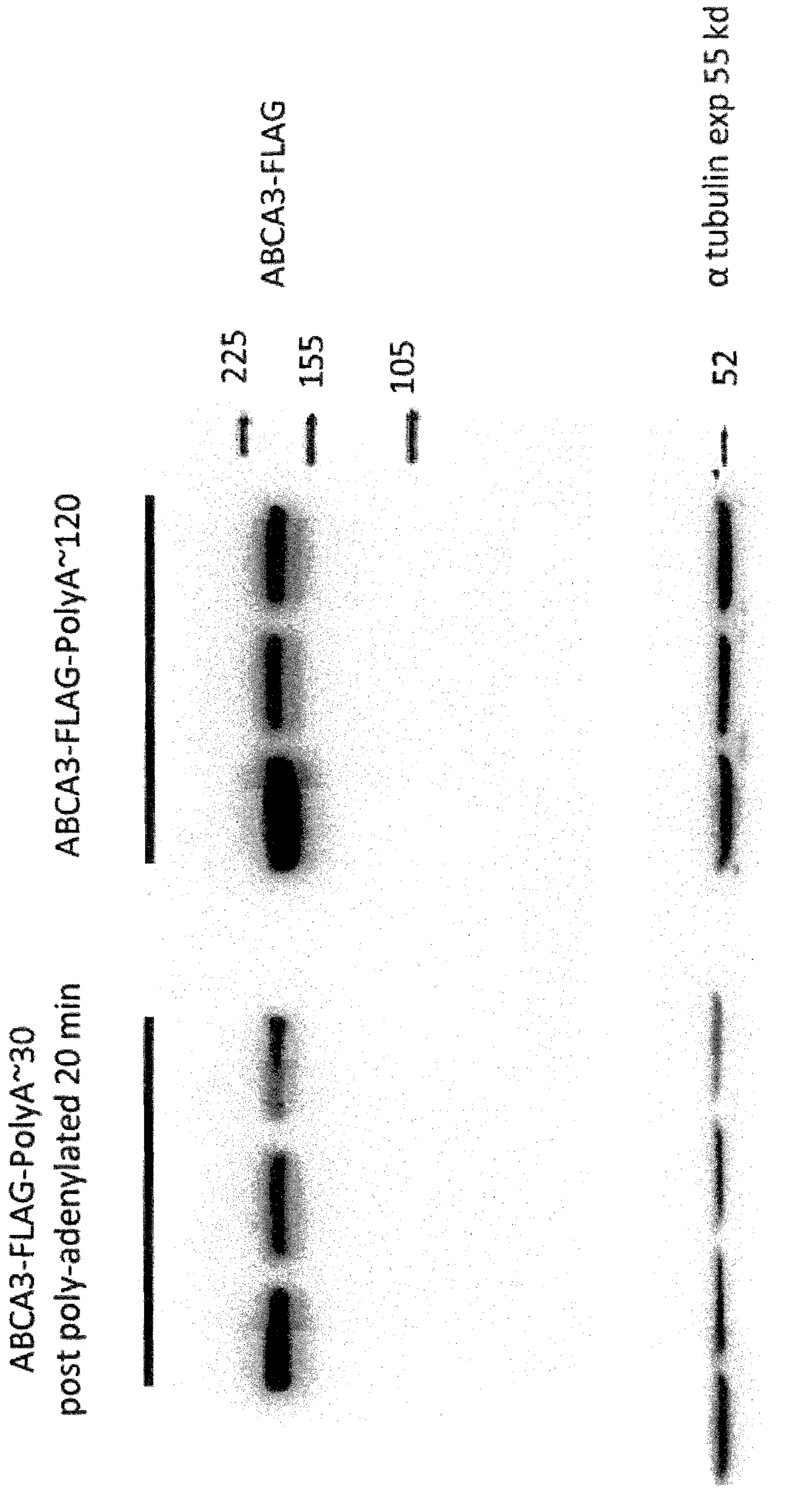
FIG. 2 is a western blot illustrating the translation of ABCA3 mRNAs with different UTRs in A549 cells 6 hours post-transfection.

This experiment demonstrates the expression (translation) of two ABCA3-FLAG mRNAs in-vitro. For this experiment, ABCA3-FLAG DNA lacking a 5' UTR (SEQ ID NO: 17) (FIG. 2: ABCA3-FLAG-PolyA-30 post poly-adenylated 20 minutes; made from a template with a 30A polyA tail that was post polyadenylated for 20 minutes to extend the tail) and ABCA3-FLAG DNA comprising a 5' human α-globin UTR (SEQ ID NO: 18) (FIG. 2: ABCA3-FLAG-PolyA-120, comprising a 5' UTR of SEQ ID NO: 5 at the DNA level and SEQ ID NO: 16 at the RNA level) were used to transcribe the corresponding mRNAs in vitro with the four canonical nucleotides, capped with a cap1 structure, and poly adenylated. These two ABCA3-FLAG mRNAs, ABCA3-FLAG-PolyA~30 post polyadenylated and ABCA3-FLAG-PolyA~100, were transfected into A549 cells. FIG. 2 is a western blot illustrating the translation of ABCA3 mRNAs in A549 cells 6 hours post-transfection. Biological triplicates are shown in the figure.

For this experiment, $2\times10^6$ A549 cells (p7) were transfected with 7.5 μg of ABCA3-FLAG-PolyA~30 or ABCA3-FLAG-PolyA~100 and harvested 6 hours post-transfection. Cells were scraped from the wells, pelleted, and the pellet was lysed in RIPA buffer. 75 μg of total protein was loaded on the gel. The blot was probed with M2 anti flag-HRP conjugated 1:10000 O/N, and developed using Femto Super signal substrate. Similar Western blot results have been obtained for MLE-15 cells.

Additional experiments demonstrating successful expression of ABC3A protein from transfected mRNA in A549 cells were conducted (data not shown). Briefly, A549 cells were transfected with mRNA encoding human ABC3A. 6 hours following transfection, cells were harvested and lysed, and ABC3A protein expression was detected by Western blot. For this experiment, codon optimized ABCA3-DNA having a CYBA 5' UTR and CYBA 3' UTR was used to transcribe the corresponding mRNAs in vitro.

Example 9: ABCA3 mRNA Expression In Vitro

The following experiment was conducted to compare the effect of incorporating specific chemically-modified nucleotides, in varying ratios and combinations, on translation efficiency in different cell types. The experiment described herein evaluated the translation in vitro from ABCA3 mRNAs (SEQ ID NO: 17) that had been prepared by in vitro transcription reactions comprising: 1) 50% Ψ; 2) 100% Ψ; 3) 25% $s^2U$+25% $m^5C$ (Mod 1); 4) 50% $I^5U$ (Mod 2); or 5) 35% $I^5U$+7.5% $I^5C$ (Mod 3). The ABCA3 mRNA template used in this experiment included a codon optimized open reading frame for ABCA3 in humans a polyA of about 30 A's in length, a cap1 structure, and it did not include a UTR (SEQ ID NO: 17).

Figure 3:
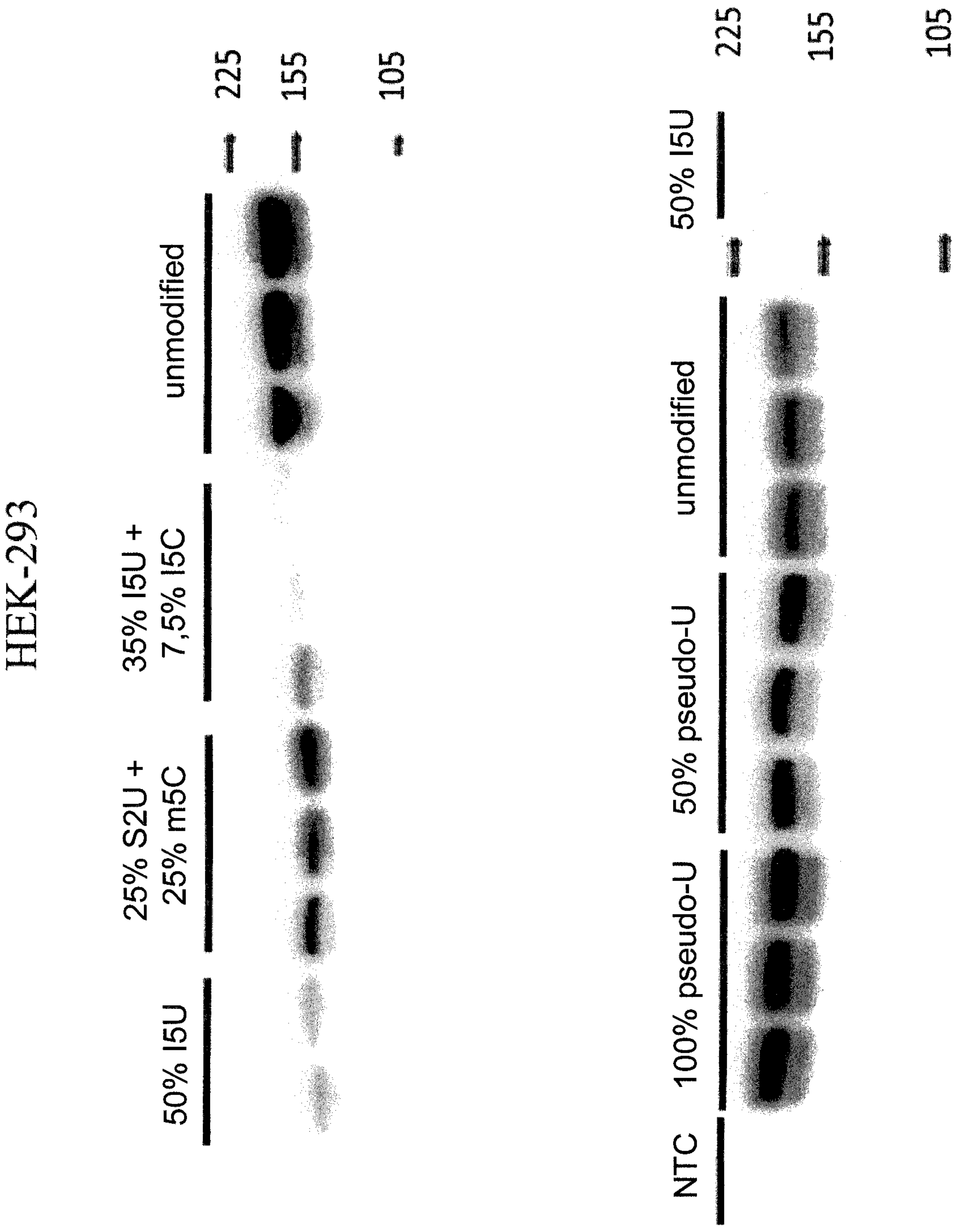
FIG. 3 is a western blot illustrating ABCA3 protein expression from mRNAs comprising various nucleotide modifications in HEK-293 cells.

ABCA-FLAG mRNA expression from HEK-293 cells (biological triplicates): Briefly, $1\times10^6$ A549 cells (biological triplicates) were transfected with 7.5 μg of ABCA3-FLAG/11.25 μl Messenger Max and harvested after 6 hrs. 50 μg of total protein was loaded on the gel. For ABCA3-FLAG detection: WB was probed with M2 anti flag-HRP conjugated 1:10000 overnight, and developed using Femto Super signal substrate. FIG. 3 is a western blot illustrating protein expression from different ABCA-FLAG mRNAs transcribed by in vitro transcription reactions comprising: 1) 50% Ψ; 2) 100% Ψ; 3) 25% $s^2U$+25% $m^5C$ (Mod 1); 4) 50% $I^5U$ (Mod 2); 5) 35% $I^5U$+7.5% $I^5C$ (Mod 3); or a control in HEK-293 cells. As shown in FIG. 3, NTC=mock transfected cells (no mRNA or plasmid).

Figure 4:
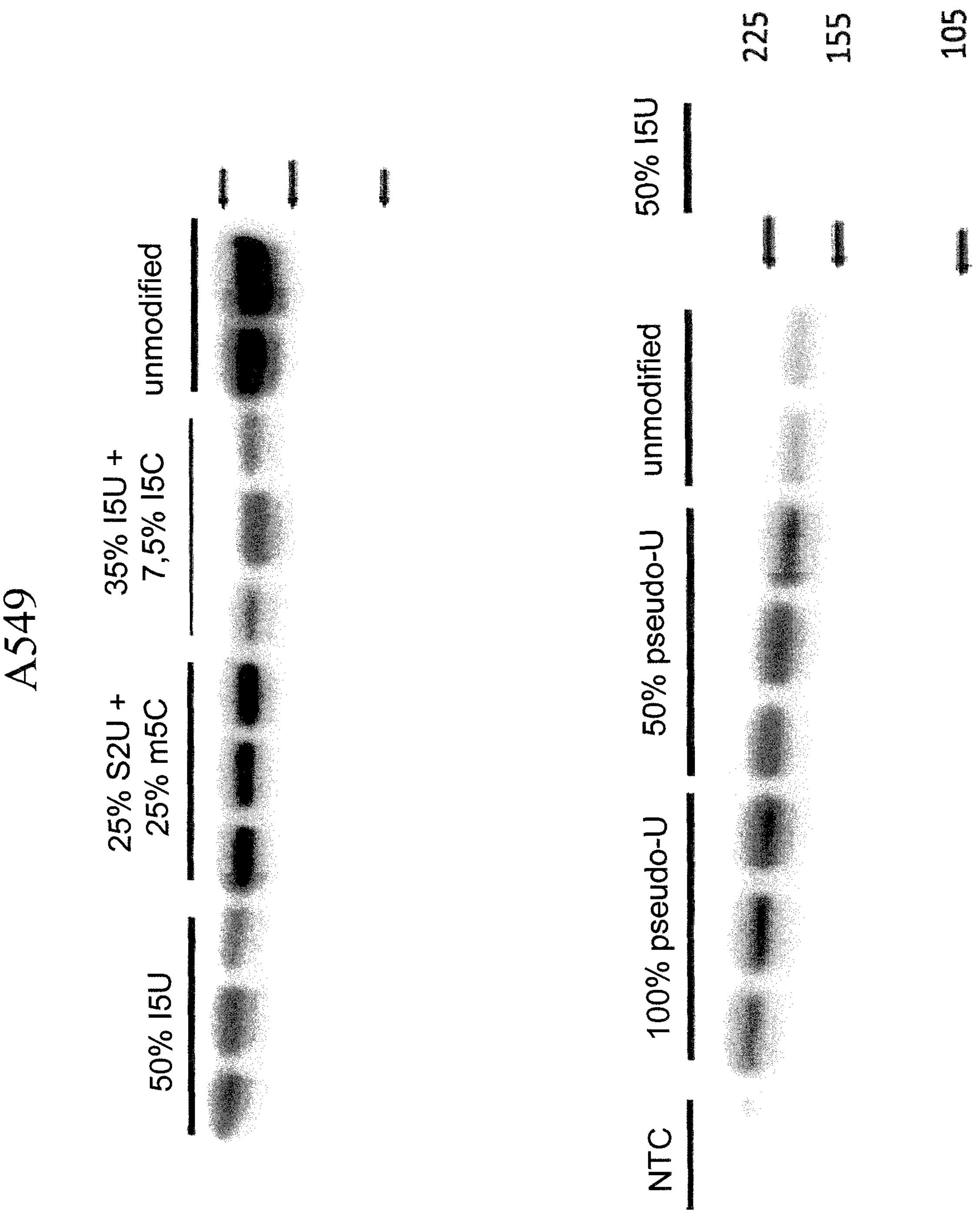
FIG. 4 is a western blot illustrating ABCA3 protein expression from mRNAs comprising various nucleotide modifications in A549 cells.

FIG. 4 is a western blot illustrating the results of a similar experiment in A549 cells. FIG. 4 illustrates the protein expression from different ABCA-FLAG mRNAs transcribed by in vitro transcription reactions comprising: 1) 50% Ψ; 2) 100% Ψ; 3) 25% $s^2U$+25% $m^5C$ (Mod 1); 4) 50% $I^5U$ (Mod 2); or 5) 35% $I^5U$+7.5% $I^5C$ (Mod 3) in A549 cells.

Figure 5:
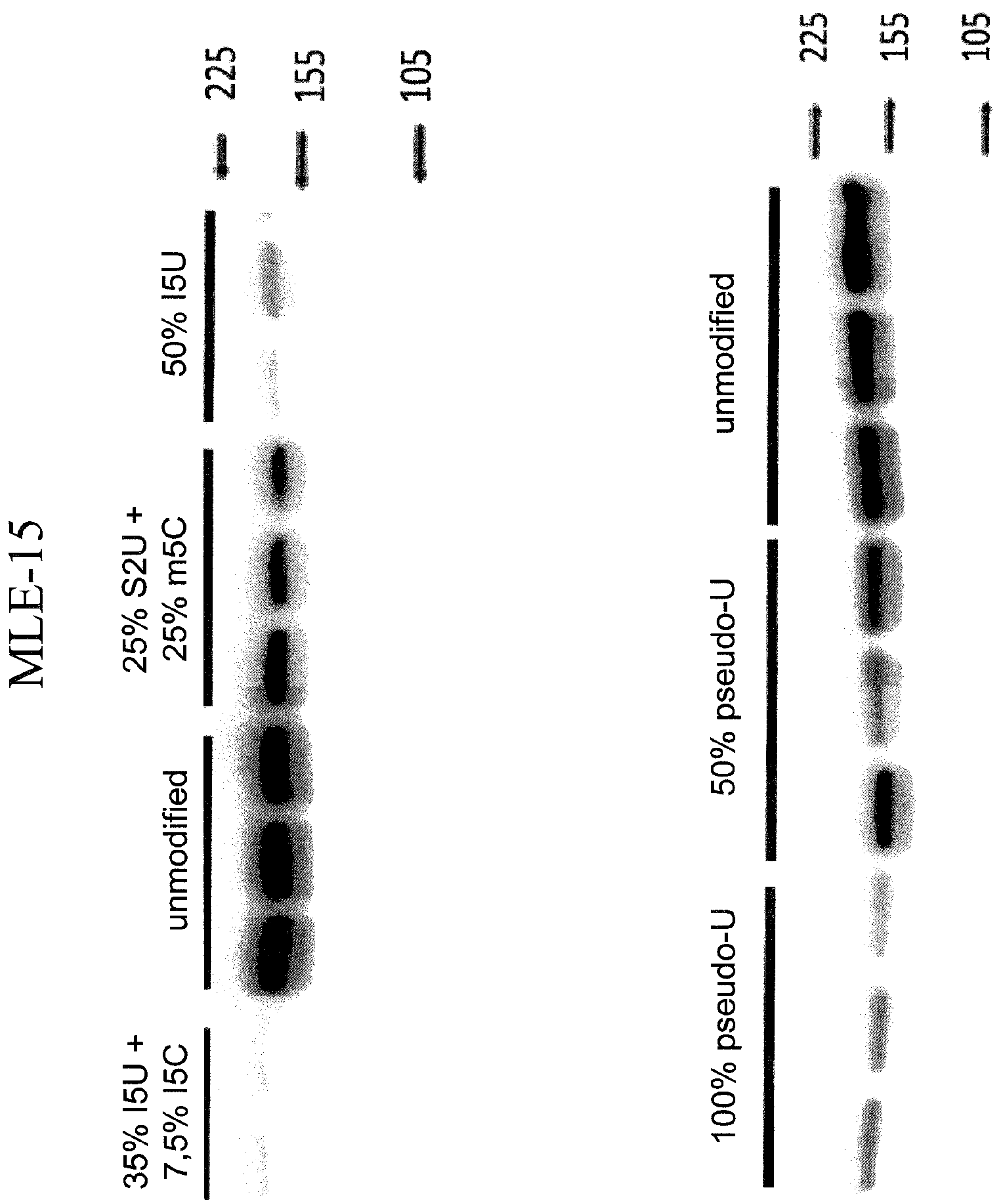
FIG. 5 is a western blot illustrating ABCA3 protein expression from mRNAs comprising various nucleotide modifications in MLE-15 cells.

Similarly, FIG. 5 is a western blot illustrating the results of ABCA3 mRNA expression in vitro in MLE-15 cells. FIG. 5 illustrates the protein expression from different ABCA-FLAG mRNAs transcribed by in vitro transcription reactions comprising: 1) 50% Ψ; 2) 100% Ψ; 3) 25% $s^2U$+25% $m^5C$ (Mod 1); 4) 50% $I^5U$ (Mod 2); or 5) 35% $I^5U$+7.5% $I^5C$ (Mod 3) in MLE-15 cells.

Figure 6:
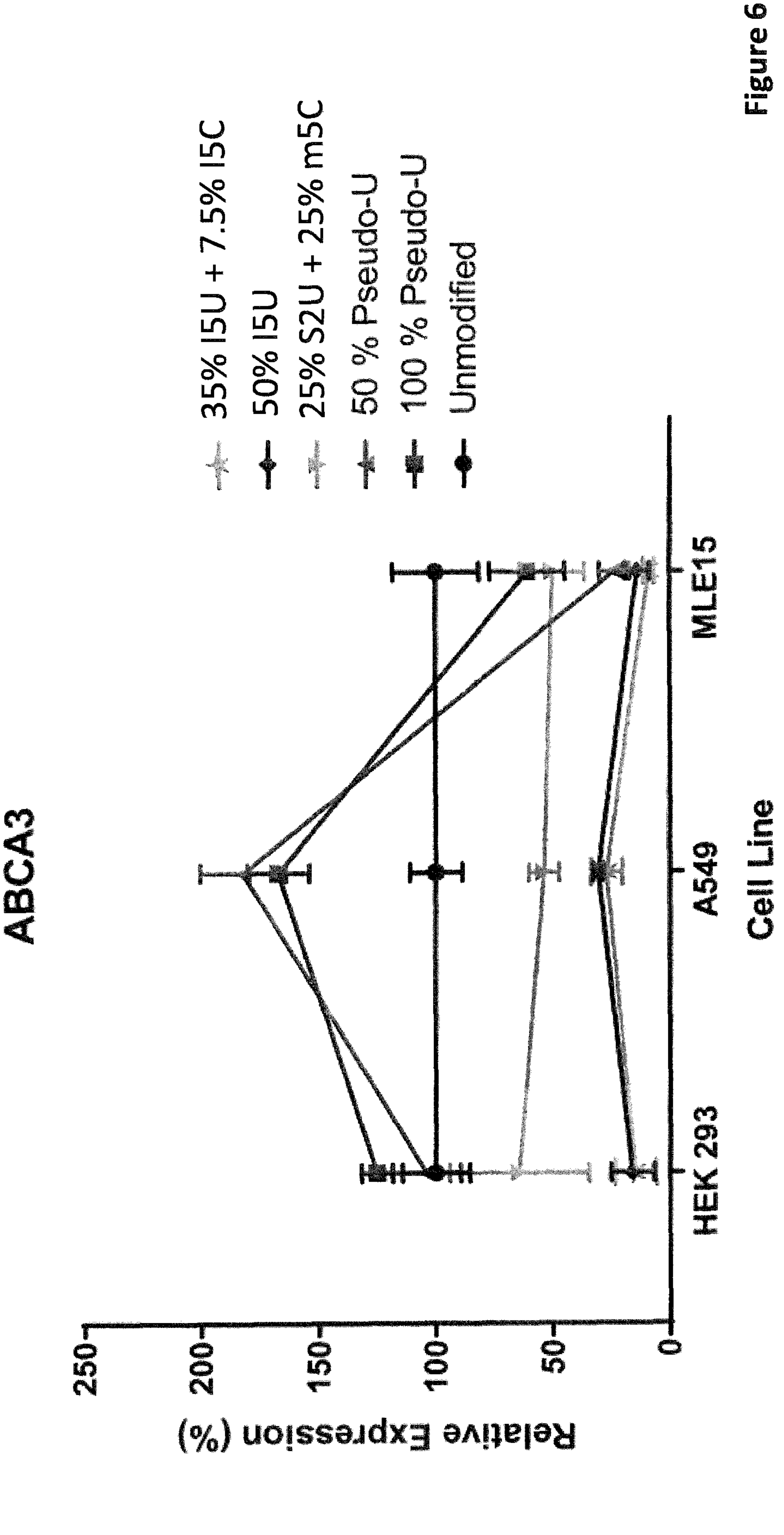
FIG. 6 illustrates a comparison of the ABCA3 protein expression levels measured by Western Blot 6 hours post mRNA transfection in HEK-293 cells, A549 cells, and MLE-15 cells.

FIG. 6 illustrates a comparison of the ABCA3 protein expression levels measured by Western Blot 6 hours post mRNA transfection in HEK-293 cells, A549 cells, and MLE-15 cells. The results are normalized to total protein staining (SYPRO Ruby). Each data point is the mean of 3 biological (transfection) replicates, error bars+/− standard deviation. All ABCA3 mRNA shown on this figure have the same sequence and were made from the same plasmid. The ABCA3 mRNA template used in this experiment included no UTRs, it had a codon optimized open reading frame for ABCA3, a polyA of about 30 A's in length, and a cap1 structure.

Example 10: Immunogenicity of ABCA3 mRNAs In Vitro

The immunogenicity of the aforementioned ABCA-FLAG mRNAs was tested in two cell lines by measuring cytokine production, namely, A549 adenocarcinomic human alveolar basal epithelial cells and HepG2 human liver carcinoma cells. Production of IL-6 in response to the transcripts was measured in A549 cells, while production of IP-10 was measured in HepG2 cells. Each cell line was transfected in triplicate with a titration of each RNA. Briefly, either 20,000 (A549) or 40,000 (HepG2) cells per well were plated 24 hours prior to transfection in 96 well plates. The cells were then transfected with a titration of each transcript, from 250 ng to 7 ng per well, using MessengerMax reagent at a RNA:MessengerMax ration of 1:1.5.

Culture supernatants were harvested at 18 hours post-transfection. Cell viability was measured immediately following supernatant removal using the CellTiter-Glo assay kit (Promega) which measures ATP levels as an indication of metabolically active cells. For IL-6 detection, A549 cell culture supernatants were diluted 1:20 in assay buffer and IL-6 levels were measured using the IL-6 High Sensitivity Human ELISA kit (Abcam ab46042). IP-10 was detected in undiluted HepG2 cell culture supernatants using the Human IP-10 ELISA Kit SimpleStep (Abeam ab173194).

Figure 7:
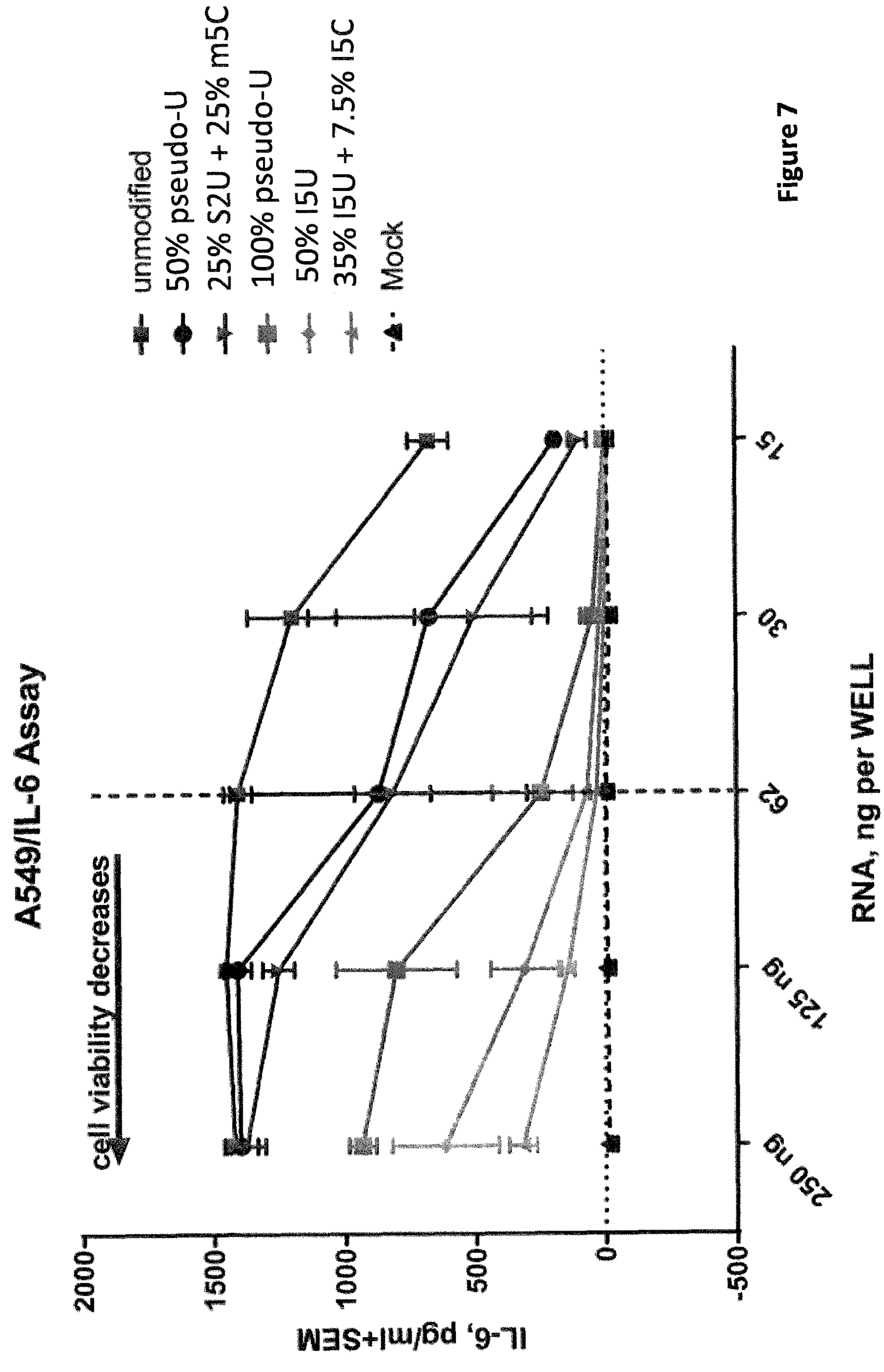
FIG. 7 illustrates the induction of IL-6 in A549 cells translating the ABCA3 protein from ABCA3-FLAG mRNAs comprising various nucleotide modifications.
Figure 8:
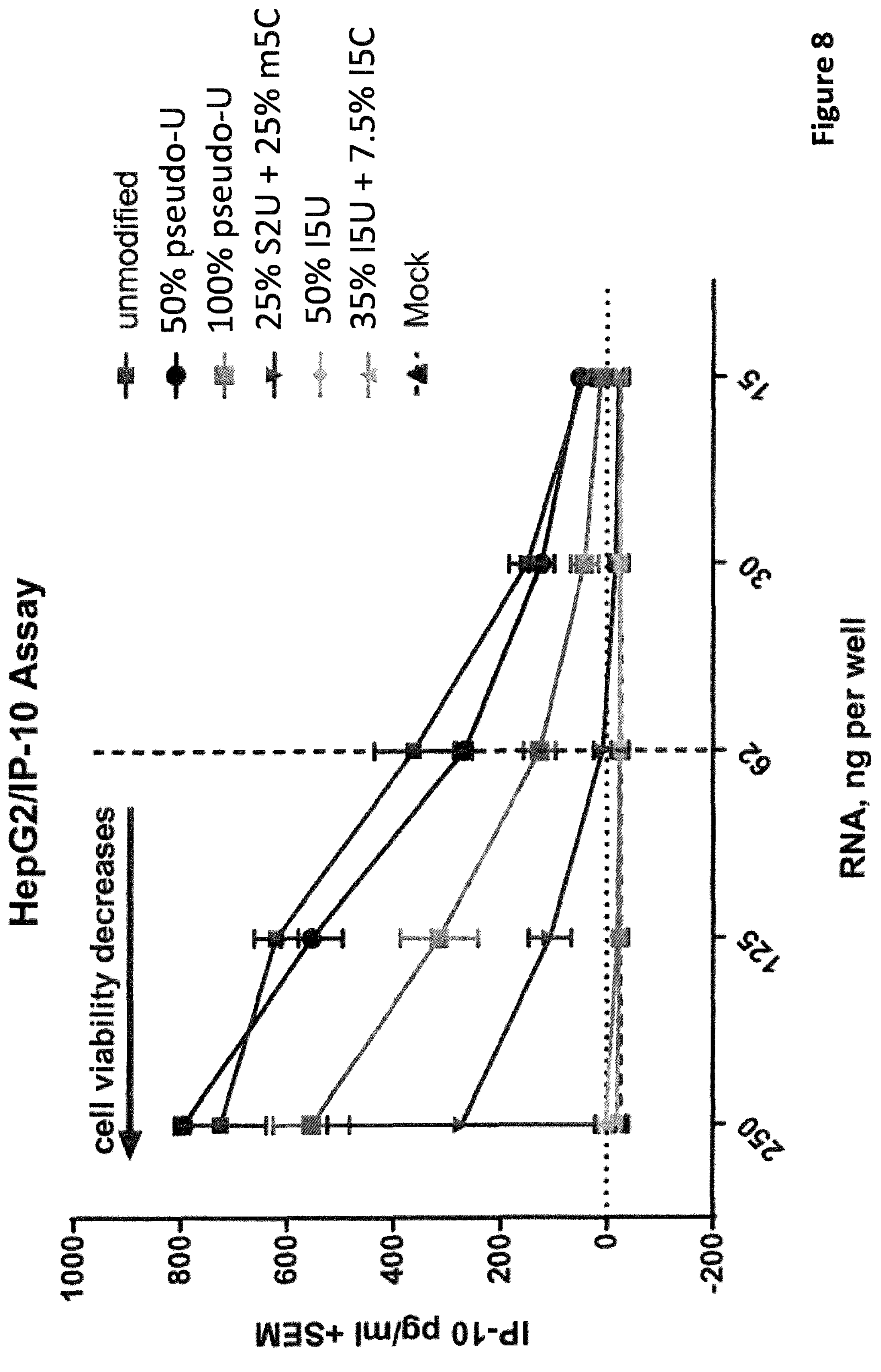
FIG. 8 illustrates induction of IP-10 in HepG2 cells translating the ABCA3 protein from ABCA3-FLAG mRNAs comprising various nucleotide modifications.

FIG. 7 illustrates the induction of IL-6 in A549 cells translating the ABCA3 protein from ABCA3-FLAG mRNAs comprising various nucleotide modifications. IL-6 expression was induced by various amounts of each ABCA-FLAG mRNA measured by ELISA. FIG. 7 illustrates cell viability after transfection with various amounts of each ABCA-FLAG mRNA measured using the CellTiter-Glo assay. FIG. 8 illustrates induction of IP-10 in HepG2 cells translating the ABCA3 protein from ABCA3-FLAG mRNAs comprising various nucleotide modifications. IP-10 expression was induced by various amounts of each ABCA-FLAG mRNA measured by ELISA. FIG. 8 illustrates cell viability after transfection with various amounts of each DNAI1 mRNA measured using the CellTiter-Glo assay.

Example 11: Cell Viability and Cytokine Induction

FIGS. 9-12 illustrate the results of a Cell Viability and Cytokine induction in vitro.

Method:

either A549 cells ($2\times10^4$/well) or HEPG2 cells ($4\times10^4$/well) were plated 24 hr prior to transfection on 96 well plates. A transfection was performed with messenger MAX, with an RNA to transfection reagent ratio of 1:1.5. This experiment use the following controls: Positive controls: 1. poly I:C was used as snim and transfected at the same concentrations; and 2. mRNA eGFP (trilink). Negative controls: 1. A549/HEP G2 treated with Opti Mem+Max reagent mix; and 2. A549/HEP G2 cells untreated. Biological duplicates were plated on 3 different 96 well plates.

Figure 9:
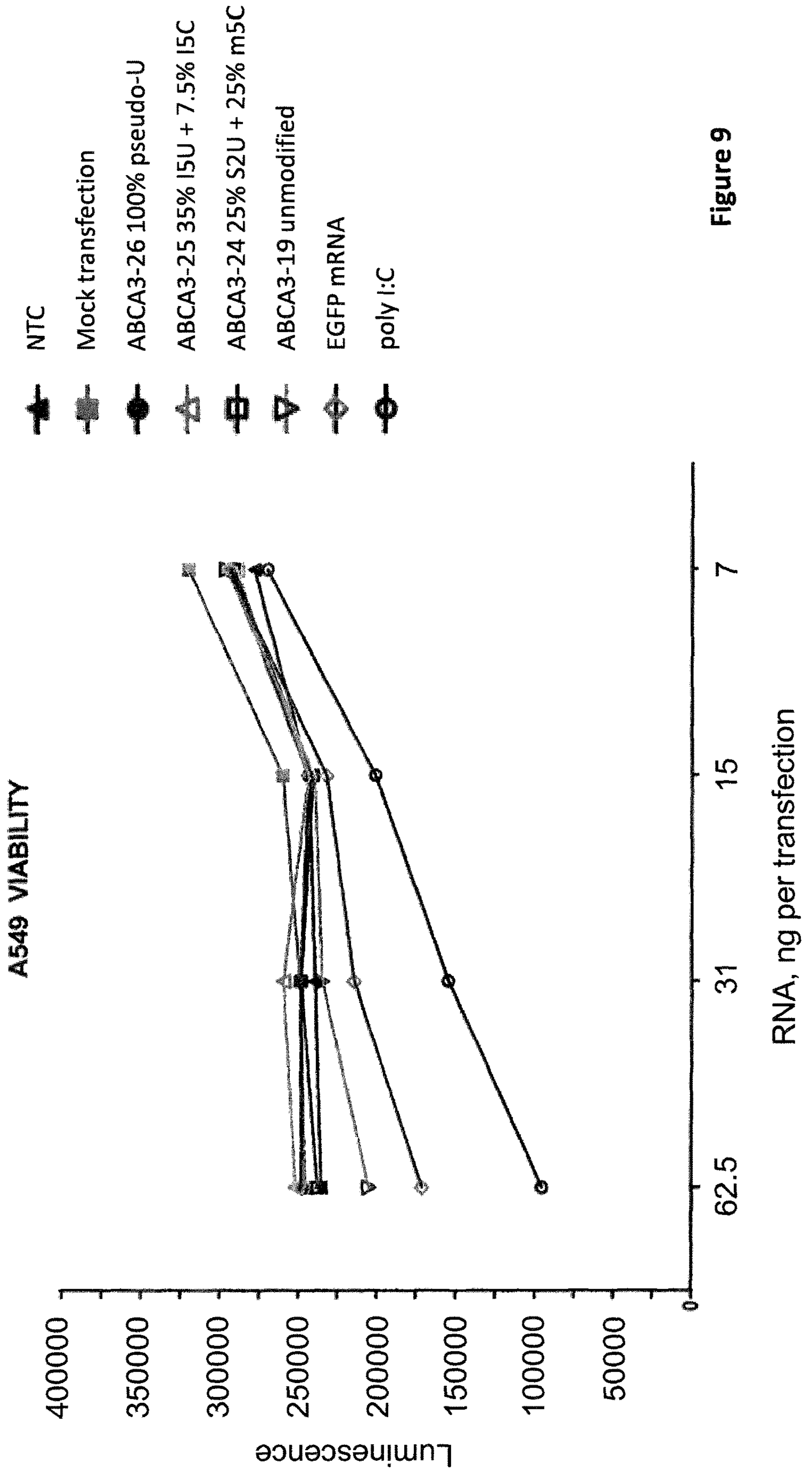
FIG. 9 illustrates the cell viability of A549 cells after transfection with mRNAs comprising various chemical modifications.
Figure 10:
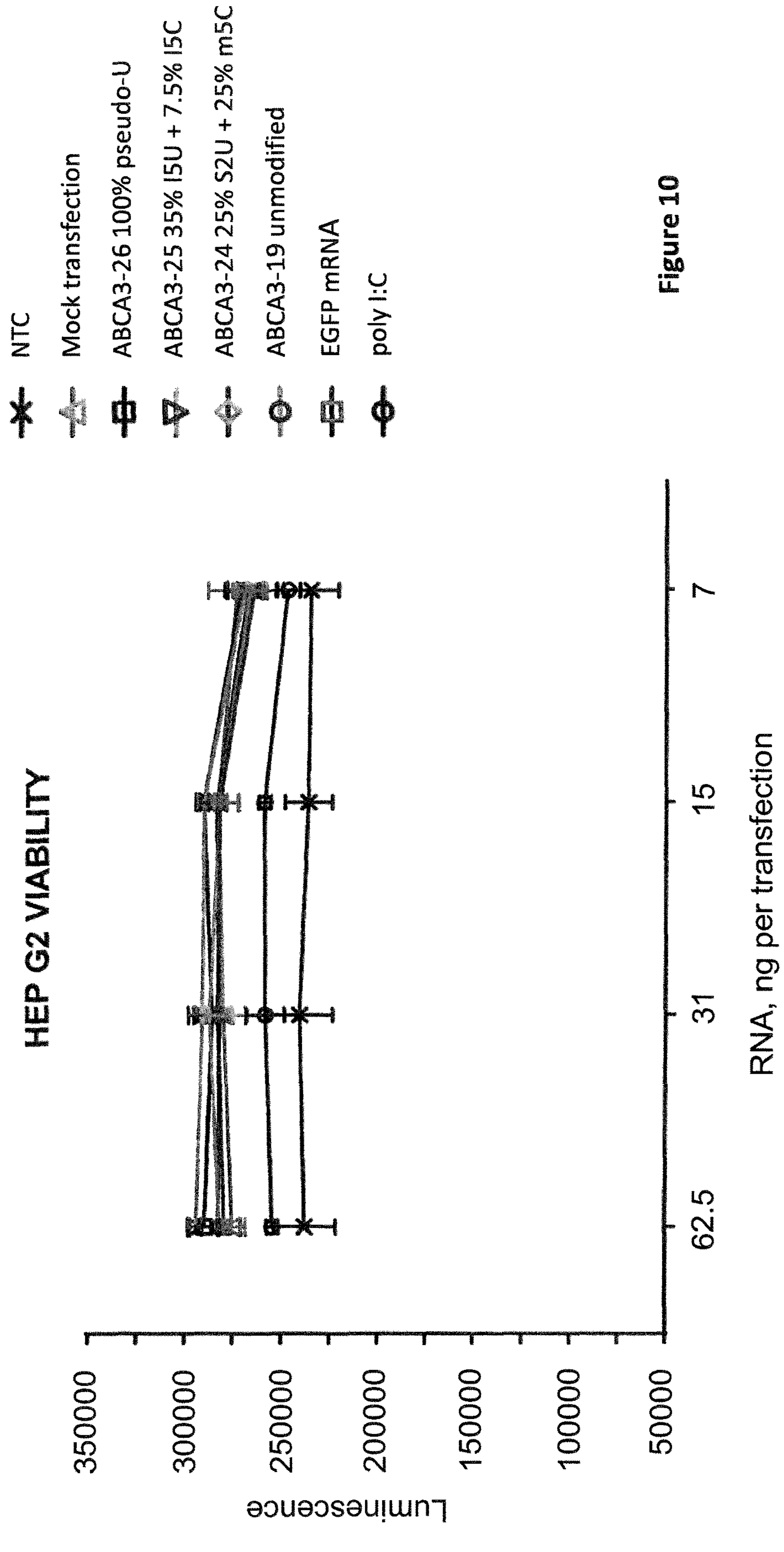
FIG. 10 illustrates the cell viability of HEP G2 cells after transfection with mRNAs comprising various chemical modifications.
Figure 11:
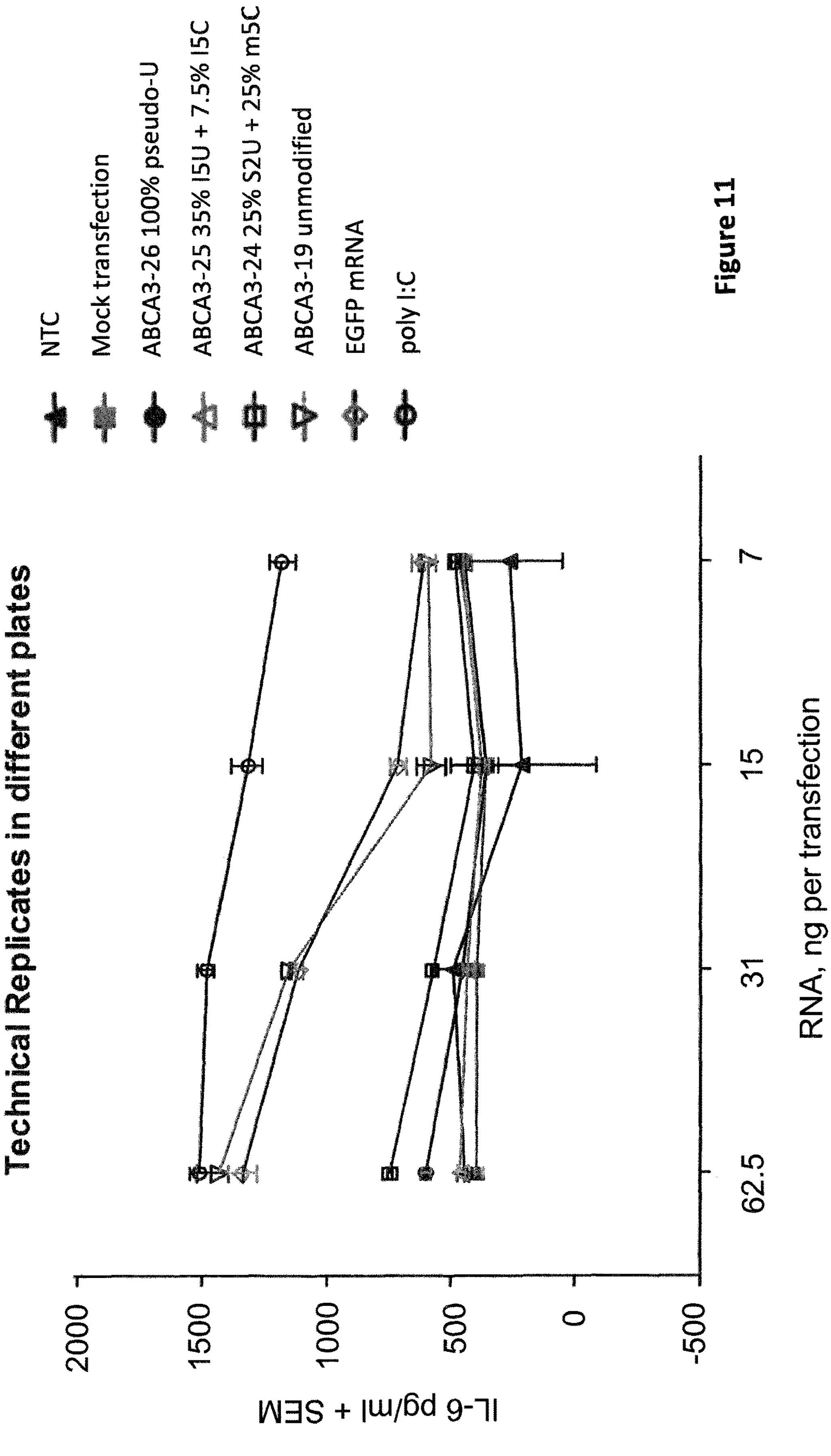
FIG. 11 illustrate the results of an ELISA assay measuring the levels of IL-6 from A549 cells after transfected with mRNAs comprising various chemical modifications.
Figure 12:
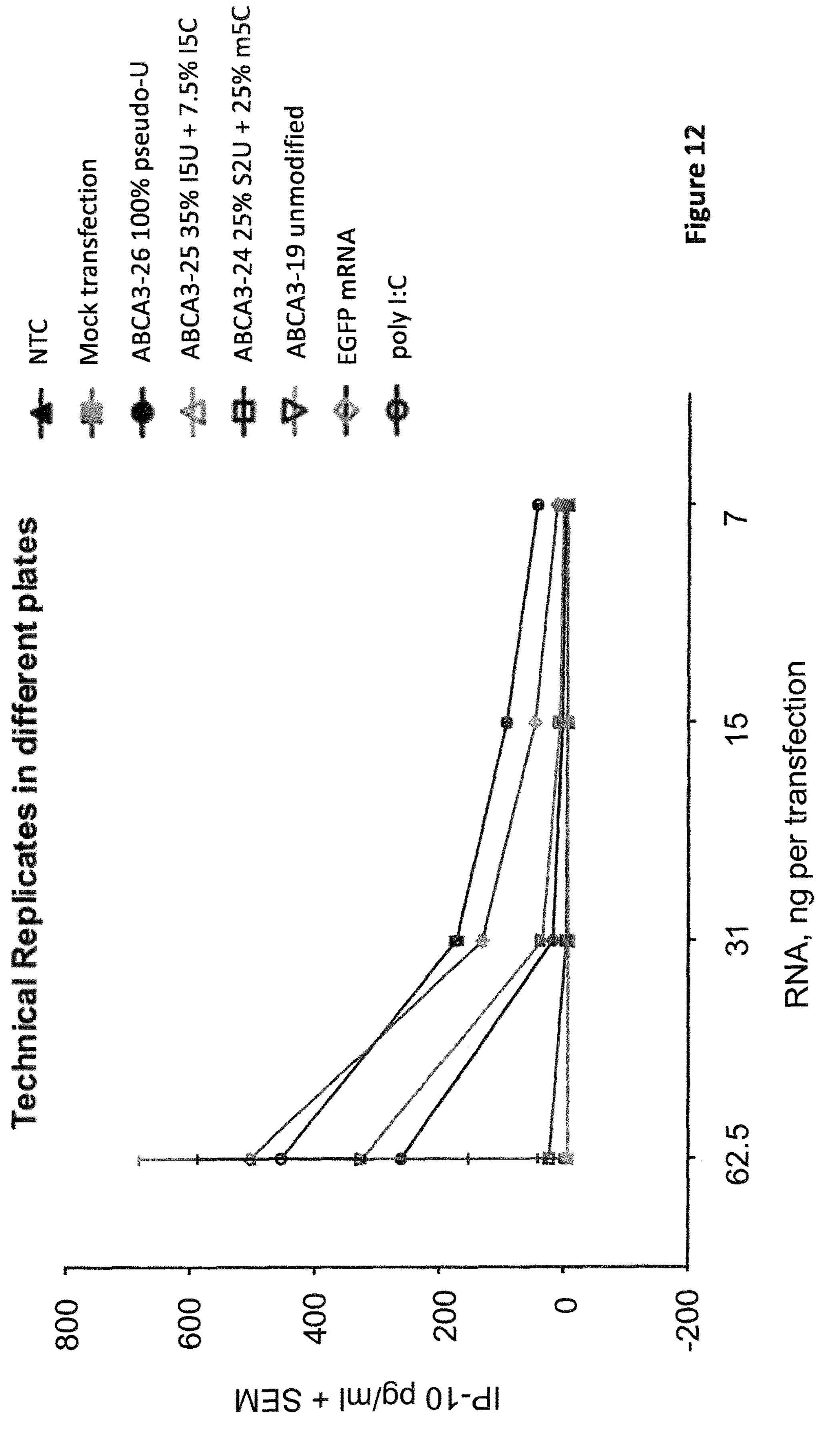
FIG. 12 illustrate the results of an ELISA assay measuring the levels of IP-10 from A549 cells after transfected with mRNAs comprising various chemical modifications.

The supernatant was harvested 18 hr post transfection and cell viability was assessed immediately after supernatant removal. FIG. 9 and FIG. 10 illustrate the cell viability of the A549 cells and HEP G2 respectively. FIG. 11 and FIG. 12 illustrate the results of the ELISA assays measuring the levels of IL-6 and IP-10. For IL-6 ELISA, the sample was diluted in assay buffer was 1:20 throughout the assay. For IP-10 an undiluted sample was tested.

Figure 13:
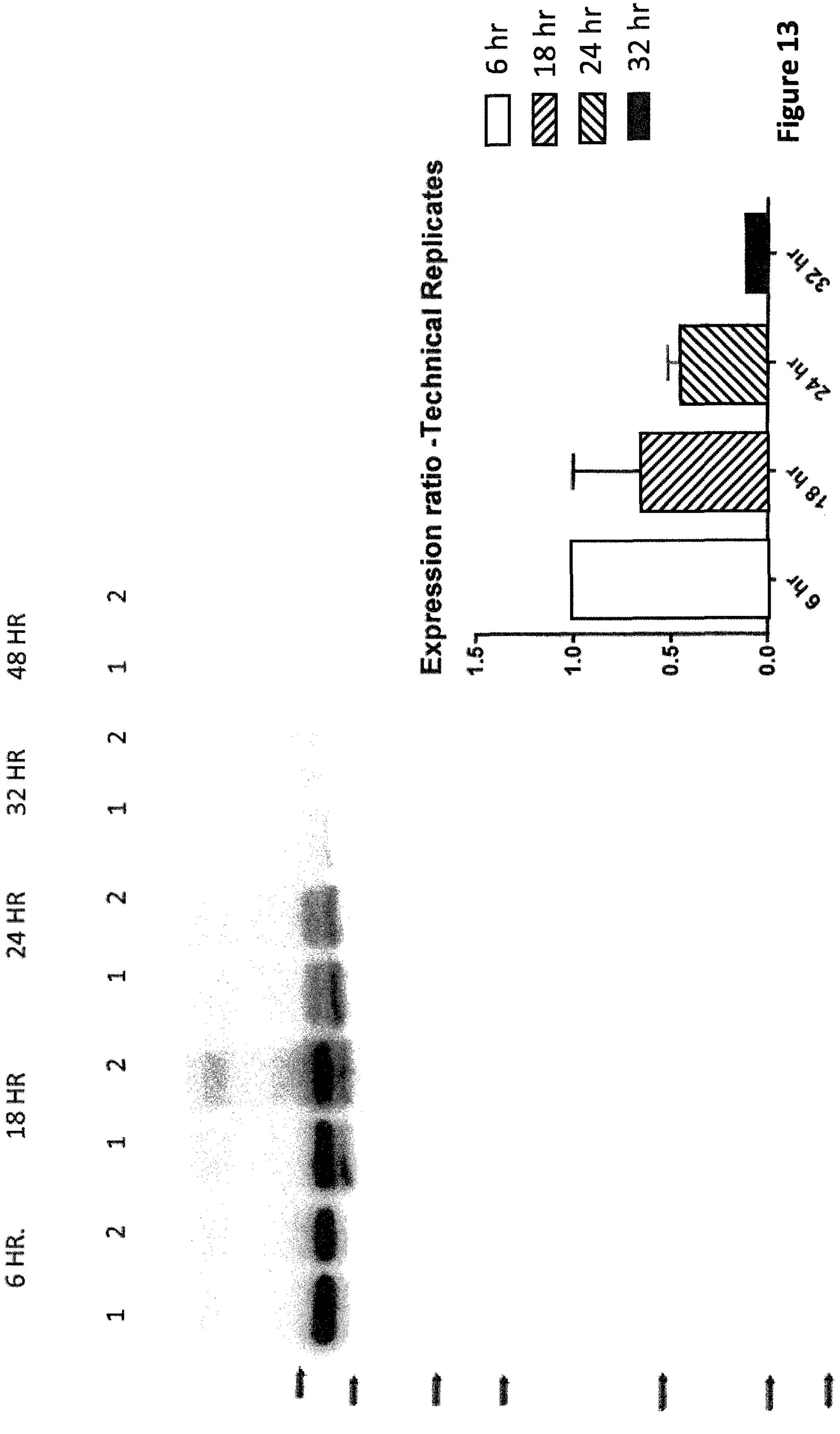
FIG. 13 is a western blot illustrating the time-course of translation of the ABCA3 polypeptide expressed from SEQ ID NO: 17 in lung cells in vitro.

Example 12: Time Course for Translation of ABCA3 mRNA in Lung Cells $1\times10^6$ A549 cells (human lung cells), passage 10, were transfected with 7.5 ug of RNA/11.5 Messenger Max in duplicates. The transfection media was changed at 4 hr post transfection and cells were harvested at different time points post transfection: 6 hr, 18 hr, 24 hr, 32 hr and 48 hr. The cells were subsequently washed with PBS and trypsinized for 5 min at room temperature. The trypsin reaction was stopped by adding FBS containing media, cells were collected, centrifuged and the pellet was washed twice with cold PBS. The pellet was then frozen. Once all the samples were collected, the frozen pellets were thawed on ice and lysed in RIPA buffer according to TTX protocol. 50 ug of protein was added to SDS-PAGE. FIG. 13 is a western blot illustrating the time-course of translation of the ABCA3 polypeptide expressed from SEQ ID NO: 17 in lung cells in vitro. For ABCA3-FLAG detection:WB was probed with M2 anti flag-HRP conjugated 1:10000 O/N, and developed using Femto Super signal substrate.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Exemplary sequences described in the application are provided below. The disclosure provides, in some embodiments, polynucleotides comprising, for example, the sequence set forth in SEQ ID NO: 17, 18, or 19, or a sequence at least 95%, 96%, 97%, 98%, or 99% identical to such sequences, or a polyribonucleotide sequence, such as an mRNA, corresponding to or encoded by any of the foregoing. In some embodiments, the disclosure provides polynucleotides comprising the sequence set forth in SEQ ID NO: 17 or 18, but in the absence of a FLAG and/or myc tag. In some embodiments, a 5'-UTR for use as part of a polynucleotide that encodes an ABC family member, comprises an untranslated region derived from a cytochrome b-245 alpha polypeptide gene or an untranslated region derived from an alpha-globin polypeptide gene, such as from a human gene. In some embodiments, a 5'-UTR for use as part of a polynucleotide that encodes an ABC family member, comprises the sequence set forth in SEQ ID NO: 5 or SEQ ID NO: 16. In certain embodiments of any of the foregoing, the polynucleotide or polyribonucleotide is modified (e.g., comprises nucleotide analogues, as described herein).

LISTING OF SEQUENCES

1) SEQ ID NO: 1
Summary: CYBA 5'
CGCGCCTAGCAGTGTCCCAGCCGGGTTCGTGTCGCC

2) SEQ ID NO: 2
Summary: CYBA 3'
CCTCGCCCCGGACCTGCCCTCCCGCCAGGTGCACCCACCTGCAATAAATGCAGCGAA

GCCGGGA

3) SEQ ID NO: 3
Summary: α-globin 5' UTR (HBA1)
CATAAACCCTGGCGCGCTCGCGGCCCGGCACTCTTCTGGTCCCCACAGACTCAGAGA

GAACCCACC

4) SEQ ID NO: 4
Summary: α-globin 5' UTR (HBA2)
(SEQ ID NO: 4)
CATAAACCCTGGCGCGCTCGCGGGCCGGCACTCTTCTGGTCCCCACAGACTCAGAGA

GAACCCACC

5) SEQ ID NO: 5
Summary: α-globin 5' UTR ETH

TCTTCTGGTCCCCACAGACTCAGAGAGAAC

6) SEQ ID NO: 6
Summary: ABCA3 5'
GCGGCCGCTGCGTCCGCCAGTAGCGGGTTGCAGGCGCACCCTCCCCTCCAGGGCG

GCCACGCAGCTGTCAGTGCCGCCGCCACTGCGAGGCTGGAGCGGAGCCCGGGTGG

CCGAGGGAGGGGACCCCGCGAGAGGGCCGCGCGCCGGCCGCCGCCGCCCCGGCG

CCCAGGCTCGGTGCTGGAGAGTCATGCCTGTGAGCCCTGGGCACCTCCTGATGTCCT

GCGAGGTCACGGTGTTCCCAAACCTCAGGGTTGCCCTGCCCCACTCCAGAGGCTCTC

AGGCCCCACCCCGGAGCCCTCTGTGCGGAGCCGCCTCCTCCTGGCCAGTTCCCCAG

TAGTCCTGAAGGGAGACCTGCTGTGTGGAGCCTCTTCTGGGACCCAGCCATGAGTGT

GGAGCTGAGCAACTGAACCTGAAACTCTTCCACTGTGAGTCAAGGAGGCTTTTCCGCA

CATGAAGGACGCTGAGCGGGAAGGACTCCTCTCTGCCTGCAGTTGTAGCGAGTGGAC

CAGCACCAGGGGCTCTCTAGACTGCCCCTCCTCCATCGCCTTCCCTGCCTCTCCAGG

ACAGAGCAGCCACGTCTGCACACCTCGCCCTCTTTACACTCAGTTTTCAGAGCACGTT

TCTCCTATTTCCTGCGGGTTGCAGCGCCTACTTGAACTTACTCAGACCACCTACTTCTC

TAGCAGCACTGGGCGTCCCTTTCAGCAAGACG

7) SEQ ID NO: 7
Summary: ABCA3 5'
GGGGTGGCGGCTGTCTCGCCATCAGGCAGGGACAGGACGGGCAAGCAGGGCCCAT

CTTACATCCTCTCTCTCCAAGTTTATCTCATCCTTTATTTTTAATCACTTTTTTCTATGAT

GGATATGAAAAATTCAAGGCAGTATGCACAGAATGGACGAGTGCAGCCCAGCCCTCA

TGCCCAGGATCAGCATGCGCATCTCCATGTCTGCATACTCTGGAGTTCACTTTCCCAG

AGCTGGGGCAGGCCGGGCAGTCTGCGGGCAAGCTCCGGGGTCTCTGGGTGGAGAG

CTGACCCAGGAAGGGCTGCAGCTGAGCTGGGGGTTGAATTTCTCCAGGCACTCCCTG

GAGAGAGGACCCAGTGACTTGTCCAAGTTTACACACGACACTAATCTCCCCTGGGGA

-continued

| LISTING OF SEQUENCES |
| --- |

GGAAGCGGGAAGCCAGCCAGGTTGAACTGTAGCGAGGCCCCCAGGCCGCCAGGAAT

GGACCATGCAGATCACTGTCAGTGGAGGGAAGCTGCTGACTGTGATTAGGTGCTGGG

GTCTTAGCGTCCAGCGCAGCCCGGGGGCATCCTGGAGGCTCTGCTCCTTAGGGCAT

GGTAGTCACCGCGAAGCCGGGCACCGTCCCACAGCATCTCCTAGAAGCAGCCGGCA

CAGGAGGGAAGGTGGCCAGGCTCGAAGCAGTCTCTGTTTCCAGCACTGCACCCTCAG

GAAGTCGCCCGCCCCAGGACACGCAGGGACCACCCTAAGGGCTGGGTGGCTGTCTC

AAGGACACATTGAATACGTTGTGACCATCCAGAAAATAAATGCTGAGGGGACACAGTC

8) SEQ ID NO: 8
Summary: ABCA3 mRNA
AUGGCUGUGCUCAGGCAGCUGGCGCUCCUCCUCUGGAAGAACUACACCCUGCAGA

AGCGGAAGGUCCUGGUGACGGUCCUGGAACUCUUCCUGCCAUUGCUGUUUUCUGG

GAUCCUCAUCUGGCUCCGCUUGAAGAUUCAGUCGGAAAAUGUGCCCAACGCCACCA

UCUACCCGGGCCAGUCCAUCCAGGAGCUGCCUCUGUUCUUCACCUUCCCUCCGCC

AGGAGACACCUGGGAGCUUGCCUACAUCCCUUCUCACAGUGACGCUGCCAAGACC

GUCACUGAGACAGUGCGCAGGGCACUUGUGAUCAACAUGCGAGUGCGCGGCUUUC

CCUCCGAGAAGGACUUUGAGGACUACAUUAGGUACGACAACUGCUCGUCCAGCGU

GCUGGCCGCCGUGGUCUUCGAGCACCCCUUCAACCACAGCAAGGAGCCCCUGCCG

CUGGCGGUGAAAUAUCACCUACGGUUCAGUUACACACGGAGAAAUUACAUGUGGAC

CCAAACAGGCUCCUUUUUCCUGAAAGAGACAGAAGGCUGGCACACUACUUCCCUUU

UCCCGCUUUUCCCAAACCCAGGACCAAGGGAACCUACAUCCCCUGAUGGCGGAGAA

CCUGGGUACAUCCGGGAAGGCUUCCUGGCCGUGCAGCAUGCUGUGGACCGGGCCA

UCAUGGAGUACCAUGCCGAUGCCGCCACACGCCAGCUGUUCCAGAGACUGACGGU

GACCAUCAAGAGGUUCCCGUACCCGCCGUUCAUCGCAGACCCCUUCCUCGUGGCC

AUCCAGUACCAGCUGCCCCUGCUGCUGCUGCUCAGCUUCACCUACACCGCGCUCA

CCAUUGCCCGUGCUGUCGUGCAGGAGAAGGAAAGGAGGCUGAAGGAGUACAUGCG

CAUGAUGGGGCUCAGCAGCUGGCUGCACUGGAGUGCCUGGUUCCUCUUGUUCUUC

CUCUUCCUCCUCAUCGCCGCCUCCUUCAUGACCCUGCUCUUCUGUGUCAAGGUGA

AGCCAAAUGUAGCCGUGCUGUCCCGCAGCGACCCCUCCCUGGUGCUCGCCUUCCU

GCUGUGCUUCGCCAUCUCUACCAUCUCCUUCAGCUUCAUGGUCAGCACCUUCUUCA

GCAAAGCCAACAUGGCAGCAGCCUUCGGAGGCUUCCUCUACUUCUUCACCUACAUC

CCCUACUUCUUCGUGGCCCCUCGGUACAACUGGAUGACUCUGAGCCAGAAGCUCU

GCUCCUGCCUCCUGUCUAAUGUCGCCAUGGCAAUGGGAGCCCAGCUCAUUGGGAA

AUUUGAGGCGAAAGGCAUGGGCAUCCAGUGGCGAGACCUCCUGAGUCCCGUCAAC

GUGGACGACGACUUCUGCUUCGGGCAGGUGCUGGGGAUGCUGCUGCUGGACUCU

GUGCUCUAUGGCCUGGUGACCUGGUACAUGGAGGCCGUCUUCCCAGGGCAGUUCG

GCGUGCCUCAGCCCUGGUACUUCUUCAUCAUGCCCUCCUAUUGGUGUGGGAAGCC

AAGGGCGGUUGCAGGGAAGGAGGAAGAAGACAGUGACCCCGAGAAAGCACUCAGAA

ACGAGUACUUUGAAGCCGAGCCAGAGGACCUGGUGGCGGGGAUCAAGAUCAAGCA

CCUGUCCAAGGUGUUCAGGGUGGGAAAUAAGGACAGGGCGGCCGUCAGAGACCUG

AACCUCAACCUGUACGAGGGACAGAUCACCGUCCUGCUGGGCCACAACGGUGCCG

LISTING OF SEQUENCES

GGAAGACCACCACCCUCUCCAUGCUCACAGGUCUCUUUCCCCCCACCAGUGGACGG

GCAUACAUCAGCGGGUAUGAAAUUUCCCAGGACAUGGUUCAGAUCCGGAAGAGCCU

GGGCCUGUGCCCGCAGCACGACAUCCUGUUUGACAACUUGACAGUCGCAGAGCAC

CUUUAUUUCUACGCCCAGCUGAAGGGCCUGUCACGUCAGAAGUGCCCUGAAGAAG

UCAAGCAGAUGCUGCACAUCAUCGGCCUGGAGGACAAGUGGAACUCACGGAGCCG

CUUCCUGAGCGGGGGCAUGAGGCGCAAGCUCUCCAUCGGCAUCGCCCUCAUCGCA

GGCUCCAAGGUGCUGAUACUGGACGAGCCCACCUCGGGCAUGGACGCCAUCUCCA

GGAGGGCCAUCUGGGAUCUUCUUCAGCGGCAGAAAAGUGACCGCACCAUCGUGCU

GACCACCCACUUCAUGGACGAGGCUGACCUGCUGGGAGACCGCAUCGCCAUCAUG

GCCAAGGGGGAGCUGCAGUGCUGCGGGUCCUCGCUGUUCCUCAAGCAGAAAUACG

GUGCCGGCUAUCACAUGACGCUGGUGAAGGAGCCGCACUGCAACCCGGAAGACAU

CUCCCAGCUGGUCCACCACCACGUGCCCAACGCCACGCUGGAGAGCAGCGCUGGG

GCCGAGCUGUCUUUCAUCCUUCCCAGAGAGAGCACGCACAGGUUUGAAGGUCUCU

UUGCUAAACUGGAGAAGAAGCAGAAAGAGCUGGGCAUUGCCAGCUUUGGGGCAUC

CAUCACCACCAUGGAGGAAGUCUUCCUUCGGGUCGGGAAGCUGGUGGACAGCAGU

AUGGACAUCCAGGCCAUCCAGCUCCCUGCCCUGCAGUACCAGCACGAGAGGCGCG

CCAGCGACUGGGCUGUGGACAGCAACCUCUGUGGGGCCAUGGACCCCUCCGACGG

CAUUGGAGCCCUCAUCGAGGAGGAGCGCACCGCUGUCAAGCUCAACACUGGGCUC

GCCCUGCACUGCCAGCAAUUCUGGGCCAUGUUCCUGAAGAAGGCCGCAUACAGCU

GGCGCGAGUGGAAAAUGGUGGCGGCACAGGUCCUGGUGCCUCUGACCUGCGUCAC

CCUGGCCCUCCUGGCCAUCAACUACUCCUCGGAGCUCUUCGACGACCCCAUGCUG

AGGCUGACCUUGGGCGAGUACGGCAGAACCGUCGUGCCCUUCUCAGUUCCCGGGA

CCUCCCAGCUGGGUCAGCAGCUGUCAGAGCAUCUGAAAGACGCACUGCAGGCUGA

GGGACAGGAGCCCCGCGAGGUGCUCGGUGACCUGGAGGAGUUCUUGAUCUUCAGG

GCUUCUGUGGAGGGGGGCGGCUUUAAUGAGCGGUGCCUUGUGGCAGCGUCCUUC

AGAGAUGUGGGAGAGCGCACGGUCGUCAACGCCUUGUUCAACAACCAGGCGUACC

ACUCUCCAGCCACUGCCCUGGCCGUCGUGGACAACCUUCUGUUCAAGCUGCUGUG

CGGGCCUCACGCCUCCAUUGUGGUCUCCAACUUCCCCCAGCCCCGGAGCGCCCUG

CAGGCUGCCAAGGACCAGUUUAACGAGGGCCGGAAGGGAUUCGACAUUGCCCUCA

ACCUGCUCUUCGCCAUGGCAUUCUUGGCCAGCACGUUCUCCAUCCUGGCGGUCAG

CGAGAGGGCCGUGCAGGCCAAGCAUGUGCAGUUUGUGAGUGGAGUCCACGUGGCC

AGUUUCUGGCUCUCUGCUCUGCUGUGGGACCUCAUCUCCUUCCUCAUCCCCAGUC

UGCUGCUGCUGGUGGUGUUUAAGGCCUUCGACGUGCGUGCCUUCACGCGGGACG

GCCACAUGGCUGACACCCUGCUGCUGCUCCUGCUCUACGGCUGGGCCAUCAUCCC

CCUCAUGUACCUGAUGAACUUCUUCUUCUUGGGGGCGGCCACUGCCUACACGAGG

CUGACCAUCUUCAACAUCCUGUCAGGCAUCGCCACCUUCCUGAUGGUCACCAUCAU

GCGCAUCCCAGCUGUAAAACUGGAAGAACUUUCCAAAACCCUGGAUCACGUGUUCC

UGGUGCUGCCCAACCACUGUCUGGGGAUGGCAGUCAGCAGUUUCUACGAGAACUA

-continued

| LISTING OF SEQUENCES |
|---|
| CGAGACGCGGAGGUACUGCACCUCCUCCGAGGUCGCCGCCCACUACUGCAAGAAA |
| UAUAACAUCCAGUACCAGGAGAACUUCUAUGCCUGGAGCGCCCCGGGGGUCGGCC |
| GGUUUGUGGCCUCCAUGGCCGCCUCAGGGUGCGCCUACCUCAUCCUGCUCUUCCU |
| CAUCGAGACCAACCUGCUUCAGAGACUCAGGGGCAUCCUCUGCGCCCUCCGGAGG |
| AGGCGGACACUGACAGAAUUAUACACCCGGAUGCCUGUGCUUCCUGAGGACCAAGA |
| UGUAGCGGACGAGAGGACCCGCAUCCUGGCCCCCAGCCCGGACUCCCUGCUCCAC |
| ACACCUCUGAUUAUCAAGGAGCUCUCCAAGGUGUACGAGCAGCGGGUGCCCCUCC |
| UGGCCGUGGACAGGCUCUCCCUCGCGGUGCAGAAAGGGGAGUGCUUCGGCCUGC |
| UGGGCUUCAAUGGAGCCGGGAAGACCACGACUUUCAAAAUGCUGACCGGGGAGGA |
| GAGCCUCACUUCUGGGGAUGCCUUUGUCGGGGGUCACAGAAUCAGCUCUGAUGUC |
| GGAAAGGUGCGGCAGCGGAUCGGCUACUGCCCGCAGUUUGAUGCCUUGCUGGACC |
| ACAUGACAGGCCGGGAGAUGCUGGUCAUGUACGCUCGGCUCCGGGGCAUCCCUGA |
| GCGCCACAUCGGGGCCUGCGUGGAGAACACUCUGCGGGGCCUGCUGCUGGAGCCA |
| CAUGCCAACAAGCUGGUCAGGACGUACAGUGGUGGUAACAAGCGGAAGCUGAGCA |
| CCGGCAUCGCCCUGAUCGGAGAGCCUGCUGUCAUCUUCCUGGACGAGCCGUCCAC |
| UGGCAUGGACCCCGUGGCCCGGCGCCUGCUUUGGGACACCGUGGCACGAGCCCGA |
| GAGUCUGGCAAGGCCAUCAUCAUCACCUCCCACAGCAUGGAGGAGUGUGAGGCCC |
| UGUGCACCCGGCUGGCCAUCAUGGUGCAGGGGCAGUUCAAGUGCCUGGGCAGCCC |
| CCAGCACCUCAAGAGCAAGUUCGGCAGCGGCUACUCCCUGCGGGCCAAGGUGCAG |
| AGUGAAGGGCAACAGGAGGCGCUGGAGGAGUUCAAGGCCUUCGUGGACCUGACCU |
| UUCCAGGCAGCGUCCUGGAAGAUGAGCACCAAGGCAUGGUCCAUUACCACCUGCC |
| GGGCCGUGACCUCAGCUGGGCGAAGGUUUUCGGUAUUCUGGAGAAAGCCAAGGAA |
| AAGUACGGCGUGGACGACUACUCCGUGAGCCAGAUCUCGCUGGAACAGGUCUUCC |
| UGAGCUUCGCCCACCUGCAGCCGCCCACCGCAGAGGAGGGGCGA |
| 9) SEQ ID NO: 9<br>Summary: ABCA3 DNA ORF (Wild-Typa)<br>ATGGCTGTGCTCAGGCAGCTGGCGCTCCTCCTCTGGAAGAACTACACCCTGCAGAAG |
| CGGAAGGTCCTGGTGACGGTCCTGGAACTCTTCCTGCCATTGCTGTTTTCTGGGATCC |
| TCATCTGGCTCCGCTTGAAGATTCAGTCGGAAAATGTGCCCAACGCCACCATCTACCC |
| GGGCCAGTCCATCCAGGAGCTGCCTCTGTTCTTCACCTTCCCTCCGCCAGGAGACAC |
| CTGGGAGCTTGCCTACATCCCTTCTCACAGTGACGCTGCCAAGACCGTCACTGAGAC |
| AGTGCGCAGGGCACTTGTGATCAACATGCGAGTGCGCGGCTTTCCCTCCGAGAAGGA |
| CTTTGAGGACTACATTAGGTACGACAACTGCTCGTCCAGCGTGCTGGCCGCCGTGGT |
| CTTCGAGCACCCCTTCAACCACAGCAAGGAGCCCCTGCCGCTGGCGGTGAAATATCA |
| CCTACGGTTCAGTTACACACGGAGAAATTACATGTGGACCCAAACAGGCTCCTTTTTC |
| CTGAAAGAGACAGAAGGCTGGCACACTACTTCCCTTTTCCCGCTTTTCCCAAACCCAG |
| GACCAAGGGAACCTACATCCCCTGATGGCGGAGAACCTGGGTACATCCGGGAAGGCT |
| TCCTGGCCGTGCAGCATGCTGTGGACCGGGCCATCATGGAGTACCATGCCGATGCCG |
| CCACACGCCAGCTGTTCCAGAGACTGACGGTGACCATCAAGAGGTTCCCGTACCCGC |
| CGTTCATCGCAGACCCCTTCCTCGTGGCCATCCAGTACCAGCTGCCCCTGCTGCTGC |

-continued

LISTING OF SEQUENCES

TGCTCAGCTTCACCTACACCGCGCTCACCATTGCCCGTGCTGTCGTGCAGGAGAAGG

AAAGGAGGCTGAAGGAGTACATGCGCATGATGGGGCTCAGCAGCTGGCTGCACTGG

AGTGCCTGGTTCCTCTTGTTCTTCCTCTTCCTCCTCATCGCCGCCTCCTTCATGACCCT

GCTCTTCTGTGTCAAGGTGAAGCCAAATGTAGCCGTGCTGTCCCGCAGCGACCCCTC

CCTGGTGCTCGCCTTCCTGCTGTGCTTCGCCATCTCTACCATCTCCTTCAGCTTCATG

GTCAGCACCTTCTTCAGCAAAGCCAACATGGCAGCAGCCTTCGGAGGCTTCCTCTACT

TCTTCACCTACATCCCCTACTTCTTCGTGGCCCCTCGGTACAACTGGATGACTCTGAG

CCAGAAGCTCTGCTCCTGCCTCCTGTCTAATGTCGCCATGGCAATGGGAGCCCAGCT

CATTGGGAAATTTGAGGCGAAAGGCATGGGCATCCAGTGGCGAGACCTCCTGAGTCC

CGTCAACGTGGACGACGACTTCTGCTTCGGGCAGGTGCTGGGGATGCTGCTGCTGGA

CTCTGTGCTCTATGGCCTGGTGACCTGGTACATGGAGGCCGTCTTCCCAGGGCAGTT

CGGCGTGCCTCAGCCCTGGTACTTCTTCATCATGCCCTCCTATTGGTGTGGGAAGCCA

AGGGCGGTTGCAGGGAAGGAGGAAGAAGACAGTGACCCCGAGAAAGCACTCAGAAA

CGAGTACTTTGAAGCCGAGCCAGAGGACCTGGTGGCGGGGATCAAGATCAAGCACCT

GTCCAAGGTGTTCAGGGTGGGAAATAAGGACAGGGCGGCCGTCAGAGACCTGAACC

TCAACCTGTACGAGGGACAGATCACCGTCCTGCTGGGCCACAACGGTGCCGGGAAG

ACCACCACCCTCTCCATGCTCACAGGTCTCTTTCCCCCCACCAGTGGACGGGCATACA

TCAGCGGGTATGAAATTTCCCAGGACATGGTTCAGATCCGGAAGAGCCTGGGCCTGT

GCCCGCAGCACGACATCCTGTTTGACAACTTGACAGTCGCAGAGCACCTTTATTTCTA

CGCCCAGCTGAAGGGCCTGTCACGTCAGAAGTGCCCTGAAGAAGTCAAGCAGATGCT

GCACATCATCGGCCTGGAGGACAAGTGGAACTCACGGAGCCGCTTCCTGAGCGGGG

GCATGAGGCGCAAGCTCTCCATCGGCATCGCCCTCATCGCAGGCTCCAAGGTGCTGA

TACTGGACGAGCCCACCTCGGGCATGGACGCCATCTCCAGGAGGGCCATCTGGGAT

CTTCTTCAGCGGCAGAAAAGTGACCGCACCATCGTGCTGACCACCCACTTCATGGAC

GAGGCTGACCTGCTGGGAGACCGCATCGCCATCATGGCCAAGGGGGAGCTGCAGTG

CTGCGGGTCCTCGCTGTTCCTCAAGCAGAAATACGGTGCCGGCTATCACATGACGCT

GGTGAAGGAGCCGCACTGCAACCCGGAAGACATCTCCCAGCTGGTCCACCACCACGT

GCCCAACGCCACGCTGGAGAGCAGCGCTGGGGCCGAGCTGTCTTTCATCCTTCCCAG

AGAGAGCACGCACAGGTTTGAAGGTCTCTTTGCTAAACTGGAGAAGAAGCAGAAAGA

GCTGGGCATTGCCAGCTTTGGGGCATCCATCACCACCATGGAGGAAGTOTTCCTTCG

GGTCGGGAAGCTGGTGGACAGCAGTATGGACATCCAGGCCATCCAGCTCCCTGCCCT

GCAGTACCAGCACGAGAGGCGCGCCAGCGACTGGGCTGTGGACAGCAACCTCTGTG

GGGCCATGGACCCCTCCGACGGCATTGGAGCCCTCATCGAGGAGGAGCGCACCGCT

GTCAAGCTCAACACTGGGCTCGCCCTGCACTGCCAGCAATTCTGGGCCATGTTCCTG

AAGAAGGCCGCATACAGCTGGCGCGAGTGGAAAATGGTGGCGGCACAGGTCCTGGT

GCCTCTGACCTGCGTCACCCTGGCCCTCCTGGCCATCAACTACTCCTCGGAGCTCTT

CGACGACCCCATGCTGAGGCTGACCTTGGGCGAGTACGGCAGAACCGTCGTGCCCT

TCTCAGTTCCCGGGACCTCCCAGCTGGGTCAGCAGCTGTCAGAGCATCTGAAAGAC G

-continued

| LISTING OF SEQUENCES |
|---|
| CACTGCAGGCTGAGGGACAGGAGCCCCGCGAGGTGCTCGGTGACCTGGAGGAGTTC |
| TTGATCTTCAGGGCTTCTGTGGAGGGGGGCGGCTTTAATGAGCGGTGCCTTGTGGCA |
| GCGTCCTTCAGAGATGTGGGAGAGCGCACGGTCGTCAACGCCTTGTTCAACAACCAG |
| GCGTACCACTCTCCAGCCACTGCCCTGGCCGTCGTGGACAACCTTCTGTTCAAGCTG |
| CTGTGCGGGCCTCACGCCTCCATTGTGGTCTCCAACTTCCCCCAGCCCCGGAGCGCC |
| CTGCAGGCTGCCAAGGACCAGTTTAACGAGGGCCGGAAGGGATTCGACATTGCCCTC |
| AACCTGCTCTTCGCCATGGCATTCTTGGCCAGCACGTTCTCCATCCTGGCGGTCAGC |
| GAGAGGGCCGTGCAGGCCAAGCATGTGCAGTTTGTGAGTGGAGTCCACGTGGCCAG |
| TTTCTGGCTCTCTGCTCTGCTGTGGGACCTCATCTCCTTCCTCATCCCCAGTCTGCTG |
| CTGCTGGTGGTGTTTAAGGCCTTCGACGTGCGTGCCTTCACGCGGGACGGCCACATG |
| GCTGACACCCTGCTGCTGCTCCTGCTCTACGGCTGGGCCATCATCCCCCTCATGTAC |
| CTGATGAACTTCTTCTTCTTGGGGGCGGCCACTGCCTACACGAGGCTGACCATCTTCA |
| ACATCCTGTCAGGCATCGCCACCTTCCTGATGGTCACCATCATGCGCATCCCAGCTGT |
| AAAACTGGAAGAACTTTCCAAAACCCTGGATCACGTGTTCCTGGTGCTGCCCAACCAC |
| TGTCTGGGGATGGCAGTCAGCAGTTTCTACGAGAACTACGAGACGCGGAGGTACTGC |
| ACCTCCTCCGAGGTCGCCGCCCACTACTGCAAGAAATATAACATCCAGTACCAGGAG |
| AACTTCTATGCCTGGAGCGCCCCGGGGGTCGGCCGGTTTGTGGCCTCCATGGCCGC |
| CTCAGGGTGCGCCTACCTCATCCTGCTCTTCCTCATCGAGACCAACCTGCTTCAGAGA |
| CTCAGGGGCATCCTCTGCGCCCTCCGGAGGAGGCGGACACTGACAGAATTATACACC |
| CGGATGCCTGTGCTTCCTGAGGACCAAGATGTAGCGGACGAGAGGACCCGCATCCTG |
| GCCCCCAGCCCGGACTCCCTGCTCCACACACCTCTGATTATCAAGGAGCTCTCCAAG |
| GTGTACGAGCAGCGGGTGCCCCTCCTGGCCGTGGACAGGCTCTCCCTCGCGGTGCA |
| GAAAGGGGAGTGCTTCGGCCTGCTGGGCTTCAATGGAGCCGGGAAGACCACGACTTT |
| CAAAATGCTGACCGGGGAGGAGAGCCTCACTTCTGGGGATGCCTTTGTCGGGGGTCA |
| CAGAATCAGCTCTGATGTCGGAAAGGTGCGGCAGCGGATCGGCTACTGCCCGCAGTT |
| TGATGCCTTGCTGGACCACATGACAGGCCGGGAGATGCTGGTCATGTACGCTCGGCT |
| CCGGGGCATCCCTGAGCGCCACATCGGGGCCTGCGTGGAGAACACTCTGCGGGGCC |
| TGCTGCTGGAGCCACATGCCAACAAGCTGGTCAGGACGTACAGTGGTGGTAACAAGC |
| GGAAGCTGAGCACCGGCATCGCCCTGATCGGAGAGCCTGCTGTCATCTTCCTGGACG |
| AGCCGTCCACTGGCATGGACCCCGTGGCCCGGCGCCTGCTTTGGGACACCGTGGCA |
| CGAGCCCGAGAGTCTGGCAAGGCCATCATCATCACCTCCCACAGCATGGAGGAGTGT |
| GAGGCCCTGTGCACCCGGCTGGCCATCATGGTGCAGGGGCAGTTCAAGTGCCTGGG |
| CAGCCCCCAGCACCTCAAGAGCAAGTTCGGCAGCGGCTACTCCCTGCGGGCCAAGG |
| TGCAGAGTGAAGGGCAACAGGAGGCGCTGGAGGAGTTCAAGGCCTTCGTGGACCTG |
| ACCTTTCCAGGCAGCGTCCTGGAAGATGAGCACCAAGGCATGGTCCATTACCACCTG |
| CCGGGCCGTGACCTCAGCTGGGCGAAGGTTTTCGGTATTCTGGAGAAAGCCAAGGAA |
| AAGTACGGCGTGGACGACTACTCCGTGAGCCAGATCTCGCTGGAACAGGTCTTCCTG |
| AGCTTCGCCCACCTGCAGCCGCCCACCGCAGAGGAGGGGCGA |

-continued

| LISTING OF SEQUENCES |
|---|

10) SEQ ID NO: 10
Summary: a nativa ABCA3 DNA saquanca with a 5' CYBA UTR and a 3' CYBA UTR (SEQ ID NO: 10)

CGCGCCTAGCAGTGTCCCAGCCGGGTTCGTGTCGCCGCCACCATGGCTGTGCTCAG

GCAGCTGGCGCTCCTCCTCTGGAAGAACTACACCCTGCAGAAGCGGAAGGTCCTGGT

GACGGTCCTGGAACTCTTCCTGCCATTGCTGTTTTCTGGGATCCTCATCTGGCTCCGC

TTGAAGATTCAGTCGGAAAATGTGCCCAACGCCACCATCTACCCGGGCCAGTCCATC

CAGGAGCTGCCTCTGTTCTTCACCTTCCCTCCGCCAGGAGACACCTGGGAGCTTGCC

TACATCCCTTCTCACAGTGACGCTGCCAAGACCGTCACTGAGACAGTGCGCAGGGCA

CTTGTGATCAACATGCGAGTGCGCGGCTTTCCCTCCGAGAAGGACTTTGAGGACTAC

ATTAGGTACGACAACTGCTCGTCCAGCGTGCTGGCCGCCGTGGTCTTCGAGCACCCC

TTCAACCACAGCAAGGAGCCCCTGCCGCTGGCGGTGAAATATCACCTACGGTTCAGT

TACACACGGAGAAATTACATGTGGACCCAAACAGGCTCCTTTTTCCTGAAAGAGACAG

AAGGCTGGCACACTACTTCCCTTTTCCCGCTTTTCCCAAACCCAGGACCAAGGGAACC

TACATCCCCTGATGGCGGAGAACCTGGGTACATCCGGGAAGGCTTCCTGGCCGTGCA

GCATGCTGTGGACCGGGCCATCATGGAGTACCATGCCGATGCCGCCACACGCCAGC

TGTTCCAGAGACTGACGGTGACCATCAAGAGGTTCCCGTACCCGCCGTTCATCGCAG

ACCCCTTCCTCGTGGCCATCCAGTACCAGCTGCCCCTGCTGCTGCTGCTCAGCTTCA

CCTACACCGCGCTCACCATTGCCCGTGCTGTCGTGCAGGAGAAGGAAAGGAGGCTGA

AGGAGTACATGCGCATGATGGGGCTCAGCAGCTGGCTGCACTGGAGTGCCTGGTTCC

TCTTGTTCTTCCTCTTCCTCCTCATCGCCGCCTCCTTCATGACCCTGCTCTTCTGTGTC

AAGGTGAAGCCAAATGTAGCCGTGCTGTCCCGCAGCGACCCCTCCCTGGTGCTCGCC

TTCCTGCTGTGCTTCGCCATCTCTACCATCTCCTTCAGCTTCATGGTCAGCACCTTCTT

CAGCAAAGCCAACATGGCAGCAGCCTTCGGAGGCTTCCTCTACTTCTTCACCTACATC

CCCTACTTCTTCGTGGCCCCTCGGTACAACTGGATGACTCTGAGCCAGAAGCTCTGCT

CCTGCCTCCTGTCTAATGTCGCCATGGCAATGGGAGCCCAGCTCATTGGGAAATTTGA

GGCGAAAGGCATGGGCATCCAGTGGCGAGACCTCCTGAGTCCCGTCAACGTGGACG

ACGACTTCTGCTTCGGGCAGGTGCTGGGGATGCTGCTGCTGGACTCTGTGCTCTATG

GCCTGGTGACCTGGTACATGGAGGCCGTCTTCCCAGGGCAGTTCGGCGTGCCTCAG

CCCTGGTACTTCTTCATCATGCCCTCCTATTGGTGTGGGAAGCCAAGGGCGGTTGCA

GGGAAGGAGGAAGAAGACAGTGACCCCGAGAAAGCACTCAGAAACGAGTACTTTGAA

GCCGAGCCAGAGGACCTGGTGGCGGGGATCAAGATCAAGCACCTGTCCAAGGTGTT

CAGGGTGGGAAATAAGGACAGGGCGGCCGTCAGAGACCTGAACCTCAACCTGTACG

AGGGACAGATCACCGTCCTGCTGGGCCACAACGGTGCCGGGAAGACCACCACCCTC

TCCATGCTCACAGGTCTCTTTCCCCCCACCAGTGGACGGGCATACATCAGCGGGTAT

GAAATTTCCCAGGACATGGTTCAGATCCGGAAGAGCCTGGGCCTGTGCCCGCAGCAC

GACATCCTGTTTGACAACTTGACAGTCGCAGAGCACCTTTATTTCTACGCCCAGCTGA

AGGGCCTGTCACGTCAGAAGTGCCCTGAAGAAGTCAAGCAGATGCTGCACATCATCG

GCCTGGAGGACAAGTGGAACTCACGGAGCCGCTTCCTGAGCGGGGGCATGAGGCGC

AAGCTCTCCATCGGCATCGCCCTCATCGCAGGCTCCAAGGTGCTGATACTGGACGAG

-continued

| LISTING OF SEQUENCES |
|---|
| CCCACCTCGGGCATGGACGCCATCTCCAGGAGGGCCATCTGGGATCTTCTTCAGCGG |
| CAGAAAAGTGACCGCACCATCGTGCTGACCACCCACTTCATGGACGAGGCTGACCTG |
| CTGGGAGACCGCATCGCCATCATGGCCAAGGGGGAGCTGCAGTGCTGCGGGTCCTC |
| GCTGTTCCTCAAGCAGAAATACGGTGCCGGCTATCACATGACGCTGGTGAAGGAGCC |
| GCACTGCAACCCGGAAGACATCTCCCAGCTGGTCCACCACCACGTGCCCAACGCCAC |
| GCTGGAGAGCAGCGCTGGGGCCGAGCTGTCTTTCATCCTTCCCAGAGAGAGCACGC |
| ACAGGTTTGAAGGTCTCTTTGCTAAACTGGAGAAGAAGCAGAAAGAGCTGGGCATTGC |
| CAGCTTTGGGGCATCCATCACCACCATGGAGGAAGTCTTCCTTCGGGTCGGGAAGCT |
| GGTGGACAGCAGTATGGACATCCAGGCCATCCAGCTCCCTGCCCTGCAGTACCAGCA |
| CGAGAGGCGCGCCAGCGACTGGGCTGTGGACAGCAACCTCTGTGGGGCCATGGACC |
| CCTCCGACGGCATTGGAGCCCTCATCGAGGAGGAGCGCACCGCTGTCAAGCTCAACA |
| CTGGGCTCGCCCTGCACTGCCAGCAATTCTGGGCCATGTTCCTGAAGAAGGCCGCAT |
| ACAGCTGGCGCGAGTGGAAAATGGTGGCGGCACAGGTCCTGGTGCCTCTGACCTGC |
| GTCACCCTGGCCCTCCTGGCCATCAACTACTCCTCGGAGCTCTTCGACGACCCCATG |
| CTGAGGCTGACCTTGGGCGAGTACGGCAGAACCGTCGTGCCCTTCTCAGTTCCCGGG |
| ACCTCCCAGCTGGGTCAGCAGCTGTCAGAGCATCTGAAAGACGCACTGCAGGCTGAG |
| GGACAGGAGCCCCGCGAGGTGCTCGGTGACCTGGAGGAGTTCTTGATCTTCAGGGC |
| TTCTGTGGAGGGGGGCGGCTTTAATGAGCGGTGCCTTGTGGCAGCGTCCTTCAGAGA |
| TGTGGGAGAGCGCACGGTCGTCAACGCCTTGTTCAACAACCAGGCGTACCACTCTCC |
| AGCCACTGCCCTGGCCGTCGTGGACAACCTTCTGTTCAAGCTGCTGTGCGGGCCTCA |
| CGCCTCCATTGTGGTCTCCAACTTCCCCCAGCCCCGGAGCGCCCTGCAGGCTGCCAA |
| GGACCAGTTTAACGAGGGCCGGAAGGGATTCGACATTGCCCTCAACCTGCTCTTCGC |
| CATGGCATTCTTGGCCAGCACGTTCTCCATCCTGGCGGTCAGCGAGAGGGCCGTGCA |
| GGCCAAGCATGTGCAGTTTGTGAGTGGAGTCCACGTGGCCAGTTTCTGGCTCTCTGC |
| TCTGCTGTGGGACCTCATCTCCTTCCTCATCCCCAGTCTGCTGCTGCTGGTGGTGTTT |
| AAGGCCTTCGACGTGCGTGCCTTCACGCGGGACGGCCACATGGCTGACACCCTGCT |
| GCTGCTCCTGCTCTACGGCTGGGCCATCATCCCCCTCATGTACCTGATGAACTTCTTC |
| TTCTTGGGGGCGGCCACTGCCTACACGAGGCTGACCATCTTCAACATCCTGTCAGGC |
| ATCGCCACCTTCCTGATGGTCACCATCATGCGCATCCCAGCTGTAAAACTGGAAGAAC |
| TTTCCAAAACCCTGGATCACGTGTTCCTGGTGCTGCCCAACCACTGTCTGGGGATGGC |
| AGTCAGCAGTTTCTACGAGAACTACGAGACGCGGAGGTACTGCACCTCCTCCGAGGT |
| CGCCGCCCACTACTGCAAGAAATATAACATCCAGTACCAGGAGAACTTCTATGCCTGG |
| AGCGCCCCGGGGGTCGGCCGGTTTGTGGCCTCCATGGCCGCCTCAGGGTGCGCCTA |
| CCTCATCCTGCTCTTCCTCATCGAGACCAACCTGCTTCAGAGACTCAGGGGCATCCTC |
| TGCGCCCTCCGGAGGAGGCGGACACTGACAGAATTATACACCCGGATGCCTGTGCTT |
| CCTGAGGACCAAGATGTAGCGGACGAGAGGACCCGCATCCTGGCCCCCAGCCCGGA |
| CTCCCTGCTCCACACACCTCTGATTATCAAGGAGCTCTCCAAGGTGTACGAGCAGCG |
| GGTGCCCCTCCTGGCCGTGGACAGGCTCTCCCTCGCGGTGCAGAAAGGGGAGTGCT |
| TCGGCCTGCTGGGCTTCAATGGAGCCGGGAAGACCACGACTTTCAAAATGCTGACCG |

-continued

LISTING OF SEQUENCES

GGGAGGAGAGCCTCACTTCTGGGGATGCCTTTGTCGGGGGTCACAGAATCAGCTCTG

ATGTCGGAAAGGTGCGGCAGCGGATCGGCTACTGCCCGCAGTTTGATGCCTTGCTGG

ACCACATGACAGGCCGGGAGATGCTGGTCATGTACGCTCGGCTCCGGGGCATCCCT

GAGCGCCACATCGGGGCCTGCGTGGAGAACACTCTGCGGGGCCTGCTGCTGGAGCC

ACATGCCAACAAGCTGGTCAGGACGTACAGTGGTGGTAACAAGCGGAAGCTGAGCAC

CGGCATCGCCCTGATCGGAGAGCCTGCTGTCATCTTCCTGGACGAGCCGTCCACTGG

CATGGACCCCGTGGCCCGGCGCCTGCTTTGGGACACCGTGGCACGAGCCCGAGAGT

CTGGCAAGGCCATCATCATCACCTCCCACAGCATGGAGGAGTGTGAGGCCCTGTGCA

CCCGGCTGGCCATCATGGTGCAGGGGCAGTTCAAGTGCCTGGGCAGCCCCCAGCAC

CTCAAGAGCAAGTTCGGCAGCGGCTACTCCCTGCGGGCCAAGGTGCAGAGTGAAGG

GCAACAGGAGGCGCTGGAGGAGTTCAAGGCCTTCGTGGACCTGACCTTTCCAGGCA

GCGTCCTGGAAGATGAGCACCAAGGCATGGTCCATTACCACCTGCCGGGCCGTGACC

TCAGCTGGGCGAAGGTTTTCGGTATTCTGGAGAAAGCCAAGGAAAAGTACGGCGTGG

ACGACTACTCCGTGAGCCAGATCTCGCTGGAACAGGTCTTCCTGAGCTTCGCCCACC

TGCAGCCGCCCACCGCAGAGGAGGGGCGAACGCGTACGCGACCGCTCGAGCAGAAA

CTCATCTCAGAAGAGGATCTGGCAGCAAATGATATCCTGGATTACAAGGATGACGACG

ATAAGGTTTGACCTCGCCCCGGACCTGCCCTCCCGCCAGGTGCACCCACCTGCAATA

AATGCAGCGAAGCCGGGAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAAAAA

AAAAAAAAAAAAAAAAAAAAATT

11) SEQ ID NO: 11
Summary: a nativa ABCA3 mRNA saquanca with a 5' CYBA UTR and a 3' CYBA UTR
(SEQ ID NO: 11)
CGCGCCUAGCAGUGUCCCAGCCGGGUUCGUGUCGCCGCCACCAUGGCUGUGCUCA

GGCAGCUGGCGCUCCUCCUCUGGAAGAACUACACCCUGCAGAAGCGGAAGGUCCU

GGUGACGGUCCUGGAACUCUUCCUGCCAUUGCUGUUUUCUGGGAUCCUCAUCUGG

CUCCGCUUGAAGAUUCAGUCGGAAAAUGUGCCCAACGCCACCAUCUACCCGGGCCA

GUCCAUCCAGGAGCUGCCUCUGUUCUUCACCUUCCCUCCGCCAGGAGACACCUGG

GAGCUUGCCUACAUCCCUUCUCACAGUGACGCUGCCAAGACCGUCACUGAGACAGU

GCGCAGGGCACUUGUGAUCAACAUGCGAGUGCGCGGCUUUCCCUCCGAGAAGGAC

UUUGAGGACUACAUUAGGUACGACAACUGCUCGUCCAGCGUGCUGGCCGCCGUGG

UCUUCGAGCACCCCUUCAACCACAGCAAGGAGCCCCUGCCGCUGGCGGUGAAAUAU

CACCUACGGUUCAGUUACACACGGAGAAAUUACAUGUGGACCCAAACAGGCUCCUU

UUUCCUGAAAGAGACAGAAGGCUGGCACACUACUUCCCUUUUCCCGCUUUUCCCAA

ACCCAGGACCAAGGGAACCUACAUCCCCUGAUGGCGGAGAACCUGGGUACAUCCG

GGAAGGCUUCCUGGCCGUGCAGCAUGCUGUGGACCGGGCCAUCAUGGAGUACCAU

GCCGAUGCCGCCACACGCCAGCUGUUCCAGAGACUGACGGUGACCAUCAAGAGGU

UCCCGUACCCGCCGUUCAUCGCAGACCCCUUCCUCGUGGCCAUCCAGUACCAGCU

GCCCCUGCUGCUGCUGCUCAGCUUCACCUACACCGCGCUCACCAUUGCCCGUGCU

GUCGUGCAGGAGAAGGAAAGGAGGCUGAAGGAGUACAUGCGCAUGAUGGGGCUCA

-continued

LISTING OF SEQUENCES

GCAGCUGGCUGCACUGGAGUGCCUGGUUCCUCUUGUUCUUCCUCUUCCUCCUCAU

CGCCGCCUCCUUCAUGACCCUGCUCUUCUGUGUCAAGGUGAAGCCAAAUGUAGCC

GUGCUGUCCCGCAGCGACCCCUCCCUGGUGCUCGCCUUCCUGCUGUGCUUCGCCA

UCUCUACCAUCUCCUUCAGCUUCAUGGUCAGCACCUUCUUCAGCAAAGCCAACAUG

GCAGCAGCCUUCGGAGGCUUCCUCUACUUCUUCACCUACAUCCCCUACUUCUUCGU

GGCCCCUCGGUACAACUGGAUGACUCUGAGCCAGAAGCUCUGCUCCUGCCUCCUG

UCUAAUGUCGCCAUGGCAAUGGGAGCCCAGCUCAUUGGGAAAUUUGAGGCGAAAG

GCAUGGGCAUCCAGUGGCGAGACCUCCUGAGUCCCGUCAACGUGGACGACGACUU

CUGCUUCGGGCAGGUGCUGGGGAUGCUGCUGCUGGACUCUGUGCUCUAUGGCCU

GGUGACCUGGUACAUGGAGGCCGUCUUCCCAGGGCAGUUCGGCGUGCCUCAGCCC

UGGUACUUCUUCAUCAUGCCCUCCUAUUGGUGUGGGAAGCCAAGGGCGGUUGCAG

GGAAGGAGGAAGAAGACAGUGACCCCGAGAAAGCACUCAGAAACGAGUACUUUGAA

GCCGAGCCAGAGGACCUGGUGGCGGGGAUCAAGAUCAAGCACCUGUCCAAGGUGU

UCAGGGUGGGAAAUAAGGACAGGGCGGCCGUCAGAGACCUGAACCUCAACCUGUA

CGAGGGACAGAUCACCGUCCUGCUGGGCCACAACGGUGCCGGGAAGACCACCACC

CUCUCCAUGCUCACAGGUCUCUUUCCCCCCACCAGUGGACGGGCAUACAUCAGCG

GGUAUGAAAUUUCCCAGGACAUGGUUCAGAUCCGGAAGAGCCUGGGCCUGUGCCC

GCAGCACGACAUCCUGUUUGACAACUUGACAGUCGCAGAGCACCUUUAUUUCUACG

CCCAGCUGAAGGGCCUGUCACGUCAGAAGUGCCCUGAAGAAGUCAAGCAGAUGCU

GCACAUCAUCGGCCUGGAGGACAAGUGGAACUCACGGAGCCGCUUCCUGAGCGGG

GGCAUGAGGCGCAAGCUCUCCAUCGGCAUCGCCCUCAUCGCAGGCUCCAAGGUGC

UGAUACUGGACGAGCCCACCUCGGGCAUGGACGCCAUCUCCAGGAGGGCCAUCUG

GGAUCUUCUUCAGCGGCAGAAAAGUGACCGCACCAUCGUGCUGACCACCCACUUCA

UGGACGAGGCUGACCUGCUGGGAGACCGCAUCGCCAUCAUGGCCAAGGGGGAGCU

GCAGUGCUGCGGGUCCUCGCUGUUCCUCAAGCAGAAAUACGGUGCCGGCUAUCAC

AUGACGCUGGUGAAGGAGCCGCACUGCAACCCGGAAGACAUCUCCCAGCUGGUCC

ACCACCACGUGCCCAACGCCACGCUGGAGAGCAGCGCUGGGGCCGAGCUGUCUUU

CAUCCUUCCCAGAGAGAGCACGCACAGGUUUGAAGGUCUCUUUGCUAAACUGGAGA

AGAAGCAGAAAGAGCUGGGCAUUGCCAGCUUUGGGGCAUCCAUCACCACCAUGGA

GGAAGUCUUCCUUCGGGUCGGGAAGCUGGUGGACAGCAGUAUGGACAUCCAGGCC

AUCCAGCUCCCUGCCCUGCAGUACCAGCACGAGAGGCGCGCCAGCGACUGGGCUG

UGGACAGCAACCUCUGUGGGGCCAUGGACCCCUCCGACGGCAUUGGAGCCCUCAU

CGAGGAGGAGCGCACCGCUGUCAAGCUCAACACUGGGCUCGCCCUGCACUGCCAG

CAAUUCUGGGCCAUGUUCCUGAAGAAGGCCGCAUACAGCUGGCGCGAGUGGAAAA

UGGUGGCGGCACAGGUCCUGGUGCCUCUGACCUGCGUCACCCUGGCCCUCCUGG

CCAUCAACUACUCCUCGGAGCUCUUCGACGACCCCAUGCUGAGGCUGACCUUGGG

CGAGUACGGCAGAACCGUCGUGCCCUUCUCAGUUCCCGGGACCUCCCAGCUGGGU

CAGCAGCUGUCAGAGCAUCUGAAAGACGCACUGCAGGCUGAGGGACAGGAGCCCC

-continued

| LISTING OF SEQUENCES |
|---|
| GCGAGGUGCUCGGUGACCUGGAGGAGUUCUUGAUCUUCAGGGCUUCUGUGGAGG |
| GGGGCGGCUUUAAUGAGCGGUGCCUUGUGGCAGCGUCCUUCAGAGAUGUGGGAG |
| AGCGCACGGUCGUCAACGCCUUGUUCAACAACCAGGCGUACCACUCUCCAGCCACU |
| GCCCUGGCCGUCGUGGACAACCUUCUGUUCAAGCUGCUGUGCGGGCCUCACGCCU |
| CCAUUGUGGUCUCCAACUUCCCCCAGCCCCGGAGCGCCCUGCAGGCUGCCAAGGA |
| CCAGUUUAACGAGGGCCGGAAGGGAUUCGACAUUGCCCUCAACCUGCUCUUCGCC |
| AUGGCAUUCUUGGCCAGCACGUUCUCCAUCCUGGCGGUCAGCGAGAGGGCCGUGC |
| AGGCCAAGCAUGUGCAGUUUGUGAGUGGAGUCCACGUGGCCAGUUUCUGGCUCUC |
| UGCUCUGCUGUGGGACCUCAUCUCCUUCCUCAUCCCCAGUCUGCUGCUGCUGGUG |
| GUGUUUAAGGCCUUCGACGUGCGUGCCUUCACGCGGGACGGCCACAUGGCUGACA |
| CCCUGCUGCUGCUCCUGCUCUACGGCUGGGCCAUCAUCCCCCUCAUGUACCUGAU |
| GAACUUCUUCUUCUUGGGGGCGGCCACUGCCUACACGAGGCUGACCAUCUUCAAC |
| AUCCUGUCAGGCAUCGCCACCUUCCUGAUGGUCACCAUCAUGCGCAUCCCAGCUG |
| UAAAACUGGAAGAACUUUCCAAAACCCUGGAUCACGUGUUCCUGGUGCUGCCCAAC |
| CACUGUCUGGGGAUGGCAGUCAGCAGUUUCUACGAGAACUACGAGACGCGGAGGU |
| ACUGCACCUCCUCCGAGGUCGCCGCCCACUACUGCAAGAAAUAUAACAUCCAGUAC |
| CAGGAGAACUUCUAUGCCUGGAGCGCCCCGGGGGUCGGCCGGUUUGUGGCCUCCA |
| UGGCCGCCUCAGGGUGCGCCUACCUCAUCCUGCUCUUCCUCAUCGAGACCAACCU |
| GCUUCAGAGACUCAGGGGCAUCCUCUGCGCCCUCCGGAGGAGGCGGACACUGACA |
| GAAUUAUACACCCGGAUGCCUGUGCUUCCUGAGGACCAAGAUGUAGCGGACGAGA |
| GGACCCGCAUCCUGGCCCCCAGCCCGGACUCCCUGCUCCACACACCUCUGAUUAU |
| CAAGGAGCUCUCCAAGGUGUACGAGCAGCGGGUGCCCCUCCUGGCCGUGGACAGG |
| CUCUCCCUCGCGGUGCAGAAAGGGGAGUGCUUCGGCCUGCUGGGCUUCAAUGGAG |
| CCGGGAAGACCACGACUUUCAAAAUGCUGACCGGGGAGGAGAGCCUCACUUCUGG |
| GGAUGCCUUUGUCGGGGGUCACAGAAUCAGCUCUGAUGUCGGAAAGGUGCGGCAG |
| CGGAUCGGCUACUGCCCGCAGUUUGAUGCCUUGCUGGACCACAUGACAGGCCGGG |
| AGAUGCUGGUCAUGUACGCUCGGCUCCGGGGCAUCCCUGAGCGCCACAUCGGGGC |
| CUGCGUGGAGAACACUCUGCGGGGCCUGCUGCUGGAGCCACAUGCCAACAAGCUG |
| GUCAGGACGUACAGUGGUGGUAACAAGCGGAAGCUGAGCACCGGCAUCGCCCUGA |
| UCGGAGAGCCUGCUGUCAUCUUCCUGGACGAGCCGUCCACUGGCAUGGACCCCGU |
| GGCCCGGCGCCUGCUUUGGGACACCGUGGCACGAGCCCGAGAGUCUGGCAAGGCC |
| AUCAUCAUCACCUCCCACAGCAUGGAGGAGUGUGAGGCCCUGUGCACCCGGCUGG |
| CCAUCAUGGUGCAGGGGCAGUUCAAGUGCCUGGGCAGCCCCCAGCACCUCAAGAG |
| CAAGUUCGGCAGCGGCUACUCCCUGCGGGCCAAGGUGCAGAGUGAAGGGCAACAG |
| GAGGCGCUGGAGGAGUUCAAGGCCUUCGUGGACCUGACCUUUCCAGGCAGCGUCC |
| UGGAAGAUGAGCACCAAGGCAUGGUCCAUUACCACCUGCCGGGCCGUGACCUCAG |
| CUGGGCGAAGGUUUUCGGUAUUCUGGAGAAAGCCAAGGAAAAGUACGGCGUGGAC |
| GACUACUCCGUGAGCCAGAUCUCGCUGGAACAGGUCUUCCUGAGCUUCGCCCACC |
| UGCAGCCGCCCACCGCAGAGGAGGGGCGAACGCGUACGCGACCGCUCGAGCAGAA |

-continued

LISTING OF SEQUENCES

ACUCAUCUCAGAAGAGGAUCUGGCAGCAAAUGAUAUCCUGGAUUACAAGGAUGACG

ACGAUAAGGUUUGACCUCGCCCCGGACCUGCCCUCCCGCCAGGUGCACCCACCUG

CAAUAAAUGCAGCGAAGCCGGGAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAUU

12) SEQ ID NO: 12
Summary: a codon optimizad ABCA3 DNA saquanca with a 5′ CYBA UTR and a 3′ CYBA UTR (SEQ ID NO: 12)
AGACCGCGCCTAGCAGTGTCCCAGCCGGGTTCGTGTCGCCGCCACCATGGCCGTGC

TGAGACAGCTGGCTCTGCTGCTGTGGAAGAACTACACCCTGCAGAAACGGAAGGTGC

TCGTGACCGTGCTGGAACTGTTCCTGCCCCTGCTGTTCAGCGGCATCCTGATCTGGC

TGCGGCTGAAGATCCAGAGCGAGAACGTGCCCAACGCCACCATCTACCCCGGCCAG

AGCATCCAGGAACTGCCCCTGTTCTTCACCTTCCCCCCACCCGGCGATACCTGGGAG

CTGGCCTATATCCCTAGCCACAGCGACGCCGCCAAGACCGTGACAGAGACAGTGCG

GAGAGCCCTCGTGATCAACATGAGAGTGCGGGGCTTCCCCAGCGAGAAGGACTTCGA

GGACTACATCAGATACGACAACTGCAGCAGCAGCGTGCTGGCCGCCGTGGTGTTTGA

GCACCCCTTCAACCACAGCAAAGAGCCCCTGCCTCTGGCCGTGAAGTACCACCTGAG

ATTCAGCTACACCCGGCGGAACTACATGTGGACCCAGACCGGCTCATTCTTCCTGAAA

GAGACAGAGGGCTGGCACACCACCAGCCTGTTCCCTCTGTTCCCCAACCCTGGCCCC

AGAGAGCCTACATCTCCTGACGGCGGCGAGCCCGGCTATATCAGAGAAGGATTCCTG

GCCGTGCAGCACGCCGTGGACAGAGCCATCATGGAATACCACGCCGATGCCGCCAC

CCGGCAGCTGTTTCAGAGACTGACCGTGACCATCAAGCGGTTCCCTTACCCCCCCTTT

ATCGCCGACCCTTTCCTGGTGGCCATCCAGTACCAGCTGCCACTCCTCCTGCTGCTG

AGCTTTACCTACACCGCCCTGACAATCGCCAGAGCCGTGGTGCAGGAAAAAGAGCGG

CGGCTGAAAGAGTACATGCGGATGATGGGCCTGTCCAGCTGGCTGCATTGGAGCGC

CTGGTTTCTGCTGTTCTTCCTGTTCCTGCTGATCGCCGCCAGCTTCATGACACTGCTG

TTTTGCGTGAAAGTGAAGCCCAACGTGGCAGTGCTGAGCCGCAGCGATCCTAGCCTG

GTGCTGGCCTTCCTGCTGTGCTTCGCCATCAGCACCATCAGCTTCAGCTTTATGGTGT

CCACCTTCTTCAGCAAGGCCAACATGGCCGCTGCCTTCGGCGGCTTCCTGTACTTCTT

TACCTATATTCCCTACTTCTTCGTGGCCCCTCGGTACAACTGGATGACCCTGAGCCAG

AAGCTGTGCAGCTGCCTGCTGAGCAACGTGGCCATGGCTATGGGAGCCCAGCTGATC

GGCAAGTTCGAGGCCAAGGGCATGGGCATCCAGTGGCGGGATCTGCTGAGCCCCGT

GAACGTGGACGACGACTTCTGCTTCGGCCAGGTGCTGGGCATGCTGCTGCTGGACTC

CGTGCTGTATGGCCTCGTGACCTGGTATATGGAAGCCGTGTTCCCTGGCCAGTTCGG

CGTGCCCCAGCCCTGGTACTTCTTCATCATGCCTAGCTATTGGTGCGGCAAGCCCAG

GGCCGTGGCCGGCAAAGAGGAAGAGGATAGCGACCCCGAGAAGGCCCTGCGGAAC

GAGTACTTTGAGGCCGAGCCCGAGGATCTGGTGGCCGGAATCAAGATCAAGCACCTG

AGCAAGGTGTTCCGCGTGGGCAACAAGGATAGAGCCGCTGTGCGGGACCTGAACCT

GAATCTGTACGAGGGCCAGATCACCGTGCTGCTGGGCCATAATGGCGCCGGAAAGAC

CACCACCCTGAGCATGCTGACCGGCCTGTTTCCCCCAACAAGCGGCAGGGCCTACAT

-continued

LISTING OF SEQUENCES

CAGCGGCTACGAGATCAGCCAGGACATGGTGCAGATCCGGAAGTCCCTGGGCCTGT

GCCCCCAGCACGACATCCTGTTCGACAACCTGACCGTGGCCGAGCACCTGTACTTTT

ACGCTCAGCTGAAGGGCCTGAGCCGGCAGAAATGCCCCGAGGAAGTGAAGCAGATG

CTGCACATCATCGGCCTGGAAGATAAGTGGAACAGCCGGTCCCGGTTCCTGTCCGGC

GGAATGAGAAGAAAGCTGAGCATCGGAATCGCCCTGATTGCCGGCAGCAAGGTGCTG

ATCCTGGACGAGCCTACCAGCGGCATGGACGCCATCTCCAGAAGGGCCATCTGGGA

CCTGCTGCAGCGGCAGAAGTCCGACAGAACCATCGTGCTGACCACCCACTTCATGGA

CGAGGCCGACCTGCTGGGCGACCGGATCGCTATTATGGCCAAGGGGGAGCTGCAGT

GCTGCGGCAGCAGCCTGTTTCTGAAGCAGAAATACGGCGCTGGCTACCACATGACCC

TCGTGAAAGAGCCTCACTGCAACCCCGAGGACATCTCCCAGCTGGTGCACCACCACG

TGCCAAATGCCACCCTGGAAAGCTCTGCCGGCGCTGAGCTGAGCTTCATCCTGCCCA

GAGAGAGCACCCACAGATTCGAGGGCCTGTTCGCCAAGCTGGAAAAGAAACAGAAAG

AGCTGGGCATTGCCAGCTTCGGCGCCAGCATCACAACAATGGAAGAGGTGTTCCTGA

GAGTGGGCAAGCTGGTGGACAGCTCCATGGACATCCAGGCTATCCAGCTGCCCGCC

CTGCAGTATCAGCACGAGAGAAGGGCTAGCGACTGGGCCGTGGACTCCAATCTGTGC

GGCGCCATGGATCCCTCCGATGGAATCGGCGCCCTGATCGAAGAGGAACGGACCGC

CGTGAAGCTGAACACAGGACTGGCCCTGCACTGCCAGCAGTTCTGGGCCATGTTCCT

GAAGAAAGCCGCCTACAGCTGGCGCGAGTGGAAAATGGTGGCCGCACAGGTGCTGG

TGCCCCTGACCTGTGTGACACTGGCACTGCTGGCCATCAACTACAGCAGCGAGCTGT

TCGACGACCCCATGCTGAGACTGACACTGGGCGAGTACGGCAGGACCGTGGTGCCT

TTTTCTGTGCCCGGCACCTCACAGCTGGGCCAGCAGCTGTCTGAACACCTGAAGGAT

GCCCTGCAGGCCGAAGGCCAGGAACCCAGAGAAGTGCTGGGCGATCTGGAAGAGTT

CCTGATCTTCCGGGCCAGCGTGGAAGGCGGCGGATTCAACGAGAGATGCCTGGTGG

CTGCCTCCTTCCGGGATGTGGGCGAGAGAACAGTCGTGAACGCCCTGTTCAACAATC

AGGCCTACCACAGCCCCGCCACCGCTCTGGCTGTGGTGGACAACCTGCTGTTTAAGC

TGCTGTGTGGCCCCCACGCCTCCATCGTGGTGTCCAATTTCCCCCAGCCCAGAAGCG

CTCTGCAGGCTGCCAAGGACCAGTTCAACGAGGGCCGGAAGGGCTTCGACATTGCTC

TGAATCTGCTGTTTGCCATGGCCTTTCTGGCCTCCACCTTCAGCATCCTGGCTGTGTC

CGAGAGAGCCGTGCAGGCCAAGCACGTGCAGTTTGTGTCTGGCGTGCACGTGGCCA

GCTTTTGGCTGTCTGCCCTGCTGTGGGACCTGATCAGCTTCCTGATCCCCAGCCTCCT

GCTGCTGGTGGTGTTCAAGGCCTTCGACGTGCGGGCCTTCACCAGGGATGGACACAT

GGCCGACACCTTGTTGTTGCTGCTGCTGTACGGCTGGGCCATCATCCCCCTGATGTA

CCTGATGAACTTCTTCTTCCTGGGCGCTGCCACCGCCTACACCAGACTGACCATCTTC

AACATCCTGAGCGGGATCGCCACCTTCCTGATGGTCACAATCATGCGGATCCCTGCC

GTGAAACTGGAAGAACTGAGCAAGACCCTGGACCATGTGTTTCTGGTGCTGCCCAAC

CACTGCCTGGGCATGGCCGTGTCTAGCTTCTACGAGAACTACGAGACACGGCGGTAC

TGCACCTCCAGCGAAGTGGCCGCCCACTACTGCAAGAAGTATAACATCCAGTATCAG

GAAAACTTCTACGCTTGGAGCGCACCCGGCGTGGGCAGATTTGTGGCCTCTATGGCC

-continued

LISTING OF SEQUENCES

GCCAGCGGCTGCGCCTATCTGATCCTGCTGTTCCTGATCGAGACTAACCTGCTGCAG

AGACTGAGAGGCATCCTGTGCGCCCTGCGGCGGAGAAGAACACTGACCGAGCTGTA

CACCCGGATGCCCGTGCTGCCTGAGGACCAGGATGTGGCCGACGAGCGGACAAGAA

TCCTGGCCCCTAGCCCCGATAGCCTGCTGCACACCCCCCTGATCATCAAAGAACTGT

CCAAGGTGTACGAGCAGCGGGTGCCACTGCTGGCTGTGGACAGACTGAGTCTGGCT

GTGCAGAAAGGCGAGTGCTTCGGACTGCTGGGCTTCAACGGCGCAGGCAAGACCAC

AACCTTCAAGATGCTGACAGGCGAGGAAAGCCTGACCTCCGGCGACGCCTTTGTGGG

CGGACACAGGATCTCTTCCGATGTGGGCAAAGTGCGGCAGCGGATCGGCTACTGCC

CTCAGTTCGACGCCCTGCTGGATCACATGACCGGCAGGGAAATGCTCGTGATGTACG

CCCGGCTGAGGGGCATCCCCGAGAGACACATTGGCGCCTGCGTGGAAAACACCCTG

CGGGGCCTGCTGCTGGAACCCCACGCTAACAAACTCGTGCGGACCTACAGCGGCGG

CAACAAGAGAAAGCTGTCTACCGGCATTGCACTGATCGGCGAGCCAGCCGTGATCTT

TCTGGATGAGCCCAGCACAGGCATGGACCCCGTGGCTCGGAGACTGCTGTGGGATA

CAGTGGCCAGAGCCAGAGAGTCCGGCAAGGCCATCATTATCACCAGCCACAGCATGG

AAGAGTGCGAGGCCCTGTGTACAAGACTGGCAATTATGGTGCAGGGACAGTTCAAGT

GTCTGGGCAGCCCTCAGCACCTGAAGTCCAAGTTCGGCTCCGGCTACAGCCTGCGG

GCCAAGGTGCAGTCTGAAGGGCAGCAGGAAGCCCTGGAAGAATTCAAAGCCTTCGTG

GACCTGACCTTCCCCGGCTCTGTGCTGGAAGATGAGCACCAGGGAATGGTGCACTAC

CATCTGCCTGGCAGGGACCTGTCCTGGGCCAAAGTGTTTGGCATCCTGGAAAAGGCC

AAAGAGAAGTACGGCGTGGACGATTACAGCGTGTCCCAGATCAGCCTGGAACAGGTG

TTCCTGTCCTTTGCCCATCTGCAGCCCCCTACCGCCGAAGAGGGAAGAACGCGTACG

CGACCGCTCGAGCAGAAACTCATCTCAGAAGAGGATCTGGCAGCAAATGATATCCTG

GATTACAAGGATGACGACGATAAGGTTTGACCTCGCCCCGGACCTGCCCTCCCGCCA

GGTGCACCCACCTGCAATAAATGCAGCGAAGCCGGGAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAATT

13) SEQ ID NO: 13
Summary: a codon optimizad ABCA3 mRNA saquanca with a 5′ CYBA UTR and a 3′ CYBA UTR (SEQ ID NO: 13).
AGACCGCGCCUAGCAGUGUCCCAGCCGGGUUCGUGUC*GCCGCCACCAUGG*CCGUG

CUGAGACAGCUGGCUCUGCUGCUGUGGAAGAACUACACCCUGCAGAAACGGAAGG

UGCUCGUGACCGUGCUGGAACUGUUCCUGCCCCUGCUGUUCAGCGGCAUCCUGAU

CUGGCUGCGGCUGAAGAUCCAGAGCGAGAACGUGCCCAACGCCACCAUCUACCCC

GGCCAGAGCAUCCAGGAACUGCCCCUGUUCUUCACCUUCCCCCCACCCGGCGAUA

CCUGGGAGCUGGCCUAUAUCCCUAGCCACAGCGACGCCGCCAAGACCGUGACAGA

GACAGUGCGGAGAGCCCUCGUGAUCAACAUGAGAGUGCGGGGCUUCCCCAGCGAG

AAGGACUUCGAGGACUACAUCAGAUACGACAACUGCAGCAGCAGCGUGCUGGCCGC

CGUGGUGUUUGAGCACCCCUUCAACCACAGCAAAGAGCCCCUGCCUCUGGCCGUG

AAGUACCACCUGAGAUUCAGCUACACCCGGCGGAACUACAUGUGGACCCAGACCGG

CUCAUUCUUCCUGAAAGAGACAGAGGGCUGGCACACCACCAGCCUGUUCCCUCUGU

-continued

| LISTING OF SEQUENCES |
|---|
| UCCCCAACCCUGGCCCCAGAGAGCCUACAUCUCCUGACGGCGGCGAGCCCGGCUA |
| UAUCAGAGAAGGAUUCCUGGCCGUGCAGCACGCCGUGGACAGAGCCAUCAUGGAA |
| UACCACGCCGAUGCCGCCACCCGGCAGCUGUUUCAGAGACUGACCGUGACCAUCAA |
| GCGGUUCCCUUACCCCCCUUUAUCGCCGACCCUUUCCUGGUGGCCAUCCAGUAC |
| CAGCUGCCACUCCUCCUGCUGCUGAGCUUUACCUACACCGCCCUGACAAUCGCCAG |
| AGCCGUGGUGCAGGAAAAAGAGCGGCGGCUGAAAGAGUACAUGCGGAUGAUGGGC |
| CUGUCCAGCUGGCUGCAUUGGAGCGCCUGGUUUCUGCUGUUCUUCCUGUUCCUGC |
| UGAUCGCCGCCAGCUUCAUGACACUGCUGUUUUGCGUGAAAGUGAAGCCCAACGU |
| GGCAGUGCUGAGCCGCAGCGAUCCUAGCCUGGUGCUGGCCUUCCUGCUGUGCUUC |
| GCCAUCAGCACCAUCAGCUUCAGCUUUAUGGUGUCCACCUUCUUCAGCAAGGCCAA |
| CAUGGCCGCUGCCUUCGGCGGCUUCCUGUACUUCUUUACCUAUAUUCCCUACUUC |
| UUCGUGGCCCCUCGGUACAACUGGAUGACCCUGAGCCAGAAGCUGUGCAGCUGCC |
| UGCUGAGCAACGUGGCCAUGGCUAUGGGAGCCCAGCUGAUCGGCAAGUUCGAGGC |
| CAAGGGCAUGGGCAUCCAGUGGCGGGAUCUGCUGAGCCCCGUGAACGUGGACGAC |
| GACUUCUGCUUCGGCCAGGUGCUGGGCAUGCUGCUGCUGGACUCCGUGCUGUAU |
| GGCCUCGUGACCUGGUAUAUGGAAGCCGUGUUCCCUGGCCAGUUCGGCGUGCCCC |
| AGCCCUGGUACUUCUUCAUCAUGCCUAGCUAUUGGUGCGGCAAGCCCAGGGCCGU |
| GGCCGGCAAAGAGGAAGAGGAUAGCGACCCCGAGAAGGCCCUGCGGAACGAGUAC |
| UUUGAGGCCGAGCCCGAGGAUCUGGUGGCCGGAAUCAAGAUCAAGCACCUGAGCA |
| AGGUGUUCCGCGUGGGCAACAAGGAUAGAGCCGCUGUGCGGGACCUGAACCUGAA |
| UCUGUACGAGGGCCAGAUCACCGUGCUGCUGGGCCAUAAUGGCGCCGGAAAGACC |
| ACCACCCUGAGCAUGCUGACCGGCCUGUUUCCCCCAACAAGCGGCAGGGCCUACA |
| UCAGCGGCUACGAGAUCAGCCAGGACAUGGUGCAGAUCCGGAAGUCCCUGGGCCU |
| GUGCCCCCAGCACGACAUCCUGUUCGACAACCUGACCGUGGCCGAGCACCUGUAC |
| UUUUACGCUCAGCUGAAGGGCCUGAGCCGGCAGAAAUGCCCCGAGGAAGUGAAGC |
| AGAUGCUGCACAUCAUCGGCCUGGAAGAUAAGUGGAACAGCCGGUCCCGGUUCCU |
| GUCCGGCGGAAUGAGAAGAAAGCUGAGCAUCGGAAUCGCCCUGAUUGCCGGCAGC |
| AAGGUGCUGAUCCUGGACGAGCCUACCAGCGGCAUGGACGCCAUCUCCAGAAGGG |
| CCAUCUGGGACCUGCUGCAGCGGCAGAAGUCCGACAGAACCAUCGUGCUGACCAC |
| CCACUUCAUGGACGAGGCCGACCUGCUGGGCGACCGGAUCGCUAUUAUGGCCAAG |
| GGGGAGCUGCAGUGCUGCGGCAGCAGCCUGUUUCUGAAGCAGAAAUACGGCGCUG |
| GCUACCACAUGACCCUCGUGAAAGAGCCUCACUGCAACCCCGAGGACAUCUCCCAG |
| CUGGUGCACCACCACGUGCCAAAUGCCACCCUGGAAAGCUCUGCCGGCGCUGAGC |
| UGAGCUUCAUCCUGCCCAGAGAGAGCACCCACAGAUUCGAGGGCCUGUUCGCCAA |
| GCUGGAAAAGAAACAGAAAGAGCUGGGCAUUGCCAGCUUCGGCGCCAGCAUCACAA |
| CAAUGGAAGAGGUGUUCCUGAGAGUGGGCAAGCUGGUGGACAGCUCCAUGGACAU |
| CCAGGCUAUCCAGCUGCCCGCCCUGCAGUAUCAGCACGAGAGAAGGGCUAGCGAC |
| UGGGCCGUGGACUCCAAUCUGUGCGGCGCCAUGGAUCCCUCCGAUGGAAUCGGCG |
| CCCUGAUCGAAGAGGAACGGACCGCCGUGAAGCUGAACACAGGACUGGCCCUGCA |

-continued

| LISTING OF SEQUENCES |
|---|

CUGCCAGCAGUUCUGGGCCAUGUUCCUGAAGAAAGCCGCCUACAGCUGGCGCGAG

UGGAAAAUGGUGGCCGCACAGGUGCUGGUGCCCCUGACCUGUGUGACACUGGCAC

UGCUGGCCAUCAACUACAGCAGCGAGCUGUUCGACGACCCCAUGCUGAGACUGACA

CUGGGCGAGUACGGCAGGACCGUGGUGCCUUUUUCUGUGCCCGGCACCUCACAGC

UGGGCCAGCAGCUGUCUGAACACCUGAAGGAUGCCCUGCAGGCCGAAGGCCAGGA

ACCCAGAGAAGUGCUGGGCGAUCUGGAAGAGUUCCUGAUCUUCCGGGCCAGCGUG

GAAGGCGGCGGAUUCAACGAGAGAUGCCUGGUGGCUGCCUCCUUCCGGGAUGUGG

GCGAGAGAACAGUCGUGAACGCCCUGUUCAACAAUCAGGCCUACCACAGCCCCGCC

ACCGCUCUGGCUGUGGUGGACAACCUGCUGUUUAAGCUGCUGUGUGGCCCCCACG

CCUCCAUCGUGGUGUCCAAUUUCCCCCAGCCCAGAAGCGCUCUGCAGGCUGCCAA

GGACCAGUUCAACGAGGGCCGGAAGGGCUUCGACAUUGCUCUGAAUCUGCUGUUU

GCCAUGGCCUUUCUGGCCUCCACCUUCAGCAUCCUGGCUGUGUCCGAGAGAGCCG

UGCAGGCCAAGCACGUGCAGUUUGUGUCUGGCGUGCACGUGGCCAGCUUUUGGCU

GUCUGCCCUGCUGUGGGACCUGAUCAGCUUCCUGAUCCCCAGCCUCCUGCUGCUG

GUGGUGUUCAAGGCCUUCGACGUGCGGGCCUUCACCAGGGAUGGACACAUGGCCG

ACACCUUGUUGUUGCUGCUGCUGUACGGCUGGGCCAUCAUCCCCCUGAUGUACCU

GAUGAACUUCUUCUUCCUGGGCGCUGCCACCGCCUACACCAGACUGACCAUCUUCA

ACAUCCUGAGCGGGAUCGCCACCUUCCUGAUGGUCACAAUCAUGCGGAUCCCUGC

CGUGAAACUGGAAGAACUGAGCAAGACCCUGGACCAUGUGUUUCUGGUGCUGCCC

AACCACUGCCUGGGCAUGGCCGUGUCUAGCUUCUACGAGAACUACGAGACACGGC

GGUACUGCACCUCCAGCGAAGUGGCCGCCCACUACUGCAAGAAGUAUAACAUCCAG

UAUCAGGAAAACUUCUACGCUUGGAGCGCACCCGGCGUGGGCAGAUUUGUGGCCU

CUAUGGCCGCCAGCGGCUGCGCCUAUCUGAUCCUGCUGUUCCUGAUCGAGACUAA

CCUGCUGCAGAGACUGAGAGGCAUCCUGUGCGCCCUGCGGCGGAGAAGAACACUG

ACCGAGCUGUACACCCGGAUGCCCGUGCUGCCUGAGGACCAGGAUGUGGCCGACG

AGCGGACAAGAAUCCUGGCCCCUAGCCCCGAUAGCCUGCUGCACACCCCCCUGAUC

AUCAAAGAACUGUCCAAGGUGUACGAGCAGCGGGUGCCACUGCUGGCUGUGGACA

GACUGAGUCUGGCUGUGCAGAAAGGCGAGUGCUUCGGACUGCUGGGCUUCAACGG

CGCAGGCAAGACCACAACCUUCAAGAUGCUGACAGGCGAGGAAAGCCUGACCUCCG

GCGACGCCUUUGUGGGCGGACACAGGAUCUCUUCCGAUGUGGGCAAAGUGCGGCA

GCGGAUCGGCUACUGCCCUCAGUUCGACGCCCUGCUGGAUCACAUGACCGGCAGG

GAAAUGCUCGUGAUGUACGCCCGGCUGAGGGGCAUCCCCGAGAGACACAUUGGCG

CCUGCGUGGAAAACACCCUGCGGGGCCUGCUGCUGGAACCCCACGCUAACAAACU

CGUGCGGACCUACAGCGGCGGCAACAAGAGAAAGCUGUCUACCGGCAUUGCACUG

AUCGGCGAGCCAGCCGUGAUCUUUCUGGAUGAGCCCAGCACAGGCAUGGACCCCG

UGGCUCGGAGACUGCUGUGGGAUACAGUGGCCAGAGCCAGAGAGUCCGGCAAGGC

CAUCAUUAUCACCAGCCACAGCAUGGAAGAGUGCGAGGCCCUGUGUACAAGACUGG

CAAUUAUGGUGCAGGGACAGUUCAAGUGUCUGGGCAGCCCUCAGCACCUGAAGUC

-continued

LISTING OF SEQUENCES

CAAGUUCGGCUCCGGCUACAGCCUGCGGGCCAAGGUGCAGUCUGAAGGGCAGCAG

GAAGCCCUGGAAGAAUUCAAAGCCUUCGUGGACCUGACCUUCCCCGGCUCUGUGC

UGGAAGAUGAGCACCAGGGAAUGGUGCACUACCAUCUGCCUGGCAGGGACCUGUC

CUGGGCCAAAGUGUUUGGCAUCCUGGAAAAGGCCAAAGAGAAGUACGGCGUGGAC

GAUUACAGCGUGUCCCAGAUCAGCCUGGAACAGGUGUUCCUGUCCUUUGCCCAUC

UGCAGCCCCCUACCGCCGAAGAGGGAAGAACGCGUACGCGACCGCUCGAGCAGAA

ACUCAUCUCAGAAGAGGAUCUGGCAGCAAAUGAUAUCCUGGAUUACAAGGAUGACG

ACGAUAAGGUUUGACCUCGCCCCGGACCUGCCCUCCCGCCAGGUGCACCCACCUG

CAAUAAAUGCAGCGAAGCCGGGAAAAAAAAAAAAAAAAAAAAAAAAAAAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAUU

14) SEQ ID NO: 14
Summary: mRNA countarpart of SEQ ID NO: 1
CGCGCCUAGCAGUGUCCCAGCCGGGUUCGUGUCGCC 15) SEQ ID NO: 15
Summary: mRNA countarpart of SEQ ID NO: 2
CCUCGCCCCGGACCUGCCCUCCCGCCAGGUGCACCCACCUGCAAUAAAUGCAGCG

AAGCCGGGA

16) SEQ ID NO: 16
Summary: mRNA countarpart of SEQ ID NO: 5
UCUUCUGGUCCCCACAGACUCAGAGAGAAC 17) SEQ ID NO: 17
Summary: Transcript TTX-ABCA3-RNA-018
Black-flanking sequences
italic, underlined-*Kozak sequence*
Blue-codon-optimized ABCA3
Red-c-myc-tag
Green-FLAG-tag,
Highlighted red-stop codon
Orange - poly(A) tail
gggagacccaagctggctagcgtttaaacttaagcttggcaatccggtactgttggtaaa*gccaccatgg*ccgtgctgagaca gctggctctgctgctgtggaagaactacaccctgcagaaacggaaggtgctcgtgaccgtgctggaactgttcctgcccctgct gttcagcggcatcctgatctggctgcggctgaagatccagagcgagaacgtgcccaacgccaccatctaccccggccagag catccaggaactgcccctgttcttcaccttcccccacccggcgatacctgggagctggcctatatccctagccacagcgacgc cgccaagaccgtgacagagacagtgcggagagccctcgtgatcaacatgagagtgcggggcttccccagcgagaaggact tcgaggactacatcagatacgacaactgcagcagcagcgtgctggccgccgtggtgtttgagcaccccttcaaccacagcaa agagcccctgcctctggccgtgaagtaccacctgagattcagctacacccggcggaactacatgtggacccagaccggctca ttcttcctgaaagagacagagggctggcacaccaccagcctgttccctctgttccccaaccctggccccagagagcctacatct cctgacggcggcgagcccggctatatcagagaaggattcctggccgtgcagcacgccgtggacagagccatcatggaatac cacgccgatgccgccacccggcagctgtttcagagactgaccgtgaccatcaagcggttcccttacccccccttatcgccgac cctttcctggtggccatccagtaccagctgccactcctcctgctgctgagctttacctacaccgccctgacaatcgccagagccgt ggtgcaggaaaaagagcggcggctgaaagagtacatgcggatgatgggcctgtccagctggctgcattggagcgcctggttt ctgctgttcttcctgttcctgctgatcgccgccagcttcatgacactgctgttttgcgtgaaagtgaagcccaacgtggcagtgctga gccgcagcgatcctagcctggtgctggccttcctgctgtgcttcgccatcagcaccatcagcttcagotttatggtgtccaccttcttc agcaaggccaacatggccgctgccttcggcggcttcctgtacttctttacctatattccctacttcttcgtggcccctcggtacaact ggatgaccctgagccagaagctgtgcagctgcctgctgagcaacgtggccatggctatgggagcccagctgatcggcaagtt -continued

LISTING OF SEQUENCES cgaggccaagggcatgggcatccagtggcgggatctgctgagccccgtgaacgtggacgacgacttctgcttcggccaggtg ctgggcatgctgctgctggactccgtgctgtatggcctcgtgacctggtatatggaagccgtgttccctggccagttcggcgtgcc ccagccctggtacttcttcatcatgcctagctattggtgcggcaagcccagggccgtggccggcaaagaggaagaggatagc gaccccgagaaggccctgcggaacgagtactttgaggccgagcccgaggatctggtggccggaatcaagatcaagcacct gagcaaggtgttccgcgtgggcaacaaggatagagccgctgtgcgggacctgaacctgaatctgtacgagggccagatcac cgtgctgctgggccataatggcgccggaaagaccaccaccctgagcatgctgaccggcctgtttcccccaacaagcggcag ggcctacatcagcggctacgagatcagccaggacatggtgcagatccggaagtccctgggcctgtgcccccagcacgacat cctgttcgacaacctgaccgtggccgagcacctgtacttttacgctcagctgaagggcctgagccggcagaaatgccccgagg aagtgaagcagatgctgcacatcatcggcctggaagataagtggaacagccggtcccggttcctgtccggcggaatgagaa gaaagctgagcatcggaatcgccctgattgccggcagcaaggtgctgatcctggacgagcctaccagcggcatggacgcca tctccagaagggccatctgggacctgctgcagcggcagaagtccgacagaaccatcgtgctgaccacccacttcatggacga ggccgacctgctgggcgaccggatcgctattatggccaagggggagctgcagtgctgcggcagcagcctgtttctgaagcag aaatacggcgctggctaccacatgaccctcgtgaaagagcctcactgcaaccccgaggacatctcccagctggtgcaccac cacgtgccaaatgccaccctggaaagctctgccggcgctgagctgagcttcatcctgcccagagagagcacccacagattcg agggcctgttcgccaagctggaaaagaaacagaaagagctgggcattgccagcttcggcgccagcatcacaacaatggaa gaggtgttcctgagagtgggcaagctggtggacagctccatggacatccaggctatccagctgcccgccctgcagtatcagca cgagagaagggctagcgactgggccgtggactccaatctgtgcggcgccatggatccctccgatggaatcggcgccctgatc gaagaggaacggaccgccgtgaagctgaacacaggactggccctgcactgccagcagttctgggccatgttcctgaagaaa gccgcctacagctggcgcgagtggaaaatggtggccgcacaggtgctggtgcccctgacctgtgtgacactggcactgctgg ccatcaactacagcagcgagctgttcgacgaccccatgctgagactgacactgggcgagtacggcaggaccgtggtgcctttt tctgtgcccggcacctcacagctgggccagcagctgtctgaacacctgaaggatgccctgcaggccgaaggccaggaaccc agagaagtgctgggcgatctggaagagttcctgatcttccgggccagcgtggaaggcggcggattcaacgagagatgcctgg tggctgcctccttccgggatgtgggcgagagaacagtcgtgaacgccctgttcaacaatcaggcctaccacagccccgccac cgctctggctgtggtggacaacctgagtttaagctgctgtgtggcccccacgcctccatcgtggtgtccaatttcccccagccca gaagcgctctgcaggctgccaaggaccagttcaacgagggccggaagggcttcgacattgctctgaatctgctgtttgccatgg cctttctggcctccaccttcagcatcctggctgtgtccgagagagccgtgcaggccaagcacgtgcagtttgtgtctggcgtgcac gtggccagcttttggctgtctgccctgctgtgggacctgatcagcttcctgatccccagcctcctgctgctggtggtgttcaaggcctt cgacgtgcgggccttcaccagggatggacacatggccgacaccttgttgttgctgctgctgtacggctgggccatcatcccctg atgtacctgatgaacttcttcttcctgggcgctgccaccgcctacaccagactgaccatcttcaacatcctgagcgggatcgcca ccttcctgatggtcacaatcatgcggatccctgccgtgaaactggaagaactgagcaagaccctggaccatgtgtttctggtgct gcccaaccactgcctgggcatggccgtgtctagcttctacgagaactacgagacacggcggtactgcacctccagcgaagtg gccgcccactactgcaagaagtataacatccagtatcaggaaaacttctacgcttggagcgcacccggcgtgggcagatttgt ggcctctatggccgccagcggctgcgcctatctgatcctgctgttcctgatcgagactaacctgctgcagagactgagaggcatc ctgtgcgccctgcggcggagaagaacactgaccgagctgtacacccggatgcccgtgctgcctgaggaccaggatgtggcc gacgagcggacaagaatcctggcccctagccccgatagcctgctgcacaccccccctgatcatcaaagaactgtccaaggtgt acgagcagcgggtgccactgctggctgtggacagactgagtctggctgtgcagaaaggcgagtgcttcggactgctgggcttc aacggcgcaggcaagaccacaaccttcaagatgctgacaggcgaggaaagcctgacctccggcgacgcctttgtgggcgg acacaggatctcttccgatgtgggcaaagtgcggcagcggatcggctactgccctcagttcgacgccctgctggatcacatga ccggcagggaaatgctcgtgatgtacgcccggctgaggggcatccccgagagacacattggcgcctgcgtggaaaacacc -continued

LISTING OF SEQUENCES ctgcggggcctgctgctggaaccccacgctaacaaactcgtgcggacctacagcggcggcaacaagagaaagctgtctacc ggcattgcactgatcggcgagccagccgtgatctttctggatgagcccagcacaggcatggaccccgtggctcggagactgct gtgggatacagtggccagagccagagagtccggcaaggccatcattatcaccagccacagcatggaagagtgcgaggccc tgtgtacaagactggcaattatggtgcagggacagttcaagtgtctgggcagccctcagcacctgaagtccaagttcggctccg gctacagcctgcgggccaaggtgcagtctgaagggcagcaggaagccctggaagagttcaaagccttcgtggacctgacctt ccccggctctgtgctggaagatgagcaccagggaatggtgcactaccatctgcctggcagggacctgtcctgggccaaagtgt ttggcatcctggaaaaggccaaagagaagtacggcgtggacgattacagcgtgtcccagatcagcctggaacaggtgttcct gtcctttgcccatctgcagccccctaccgccgaagagggaagaacgcgtacgcggccgctcgagcagaaactcatctcaga agaggatctggcagcaaatgatatcctggattacaaggatgacgacgataaggttttaagaattctgcagAAAAAAAAAA

AAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAGC

18) SEQ ID NO: 18
Summary: Transcript TTX-ABCA3-RNA-019
Black-flanking sequences
Gray-5' UTR human alpha globin
italic, underlined-*Kozak sequence*
Blue-codon-optimized ABCA3
Red-c-myc-tag
Green-FLAG-tag
Highlighted red-stop codon
Orange-poly(A) tail
GGGAGACTCTTCTGGTCCCCACAGACTCAGAGAGAAC*GCCACCATG*GCCGTGCTGAG

ACAGCTGGCTCTGCTGCTGTGGAAGAACTACACCCTGCAGAAACGGAAGGTGCTCGT

GACCGTGCTGGAACTGTTCCTGCCCCTGCTGTTCAGCGGCATCCTGATCTGGCTGCG

GCTGAAGATCCAGAGCGAGAACGTGCCCAACGCCACCATCTACCCCGGCCAGAGCAT

CCAGGAACTGCCCCTGTTCTTCACCTTCCCCCCACCCGGCGATACCTGGGAGCTGGC

CTATATCCCTAGCCACAGCGACGCCGCCAAGACCGTGACAGAGACAGTGCGGAGAG

CCCTCGTGATCAACATGAGAGTGCGGGGCTTCCCCAGCGAGAAGGACTTCGAGGACT

ACATCAGATACGACAACTGCAGCAGCAGCGTGCTGGCCGCCGTGGTGTTTGAGCACC

CCTTCAACCACAGCAAAGAGCCCCTGCCTCTGGCCGTGAAGTACCACCTGAGATTCA

GCTACACCCGGCGGAACTACATGTGGACCCAGACCGGCTCATTCTTCCTGAAAGAGA

CAGAGGGCTGGCACACCACCAGCCTGTTCCCTCTGTTCCCCAACCCTGGCCCCAGAG

AGCCTACATCTCCTGACGGCGGCGAGCCCGGCTATATCAGAGAAGGATTCCTGGCCG

TGCAGCACGCCGTGGACAGAGCCATCATGGAATACCACGCCGATGCCGCCACCCGG

CAGCTGTTTCAGAGACTGACCGTGACCATCAAGCGGTTCCCTTACCCCCCCTTTATCG

CCGACCCTTTCCTGGTGGCCATCCAGTACCAGCTGCCACTCCTCCTGCTGCTGAGCTT

TACCTACACCGCCCTGACAATCGCCAGAGCCGTGGTGCAGGAAAAAGAGCGGCGGC

TGAAAGAGTACATGCGGATGATGGGCCTGTCCAGCTGGCTGCATTGGAGCGCCTGGT

TTCTGCTGTTCTTCCTGTTCCTGCTGATCGCCGCCAGCTTCATGACACTGCTGTTTTGC

GTGAAAGTGAAGCCCAACGTGGCAGTGCTGAGCCGCAGCGATCCTAGCCTGGTGCT

GGCCTTCCTGCTGTGCTTCGCCATCAGCACCATCAGCTTCAGCTTTATGGTGTCCACC

TTCTTCAGCAAGGCCAACATGGCCGCTGCCTTCGGCGGCTTCCTGTACTTCTTTACCT

ATATTCCCTACTTCTTCGTGGCCCCTCGGTACAACTGGATGACCCTGAGCCAGAAGCT

-continued

LISTING OF SEQUENCES

```
GTGCAGCTGCCTGCTGAGCAACGTGGCCATGGCTATGGGAGCCCAGCTGATCGGCA
AGTTCGAGGCCAAGGGCATGGGCATCCAGTGGCGGGATCTGCTGAGCCCCGTGAAC
GTGGACGACGACTTCTGCTTCGGCCAGGTGCTGGGCATGCTGCTGCTGGACTCCGTG
CTGTATGGCCTCGTGACCTGGTATATGGAAGCCGTGTTCCCTGGCCAGTTCGGCGTG
CCCCAGCCCTGGTACTTCTTCATCATGCCTAGCTATTGGTGCGGCAAGCCCAGGGCC
GTGGCCGGCAAAGAGGAAGAGGATAGCGACCCCGAGAAGGCCCTGCGGAACGAGTA
CTTTGAGGCCGAGCCCGAGGATCTGGTGGCCGGAATCAAGATCAAGCACCTGAGCAA
GGTGTTCCGCGTGGGCAACAAGGATAGAGCCGCTGTGCGGGACCTGAACCTGAATCT
GTACGAGGGCCAGATCACCGTGCTGCTGGGCCATAATGGCGCCGGAAAGACCACCA
CCCTGAGCATGCTGACCGGCCTGTTTCCCCCAACAAGCGGCAGGGCCTACATCAGCG
GCTACGAGATCAGCCAGGACATGGTGCAGATCCGGAAGTCCCTGGGCCTGTGCCCC
CAGCACGACATCCTGTTCGACAACCTGACCGTGGCCGAGCACCTGTACTTTTACGCTC
AGCTGAAGGGCCTGAGCCGGCAGAAATGCCCCGAGGAAGTGAAGCAGATGCTGCAC
ATCATCGGCCTGGAAGATAAGTGGAACAGCCGGTCCCGGTTCCTGTCCGGCGGAATG
AGAAGAAAGCTGAGCATCGGAATCGCCCTGATTGCCGGCAGCAAGGTGCTGATCCTG
GACGAGCCTACCAGCGGCATGGACGCCATCTCCAGAAGGGCCATCTGGGACCTGCT
GCAGCGGCAGAAGTCCGACAGAACCATCGTGCTGACCACCCACTTCATGGACGAGGC
CGACCTGCTGGGCGACCGGATCGCTATTATGGCCAAGGGGGAGCTGCAGTGCTGCG
GCAGCAGCCTGTTTCTGAAGCAGAAATACGGCGCTGGCTACCACATGACCCTCGTGA
AAGAGCCTCACTGCAACCCCGAGGACATCTCCCAGCTGGTGCACCACCACGTGCCAA
ATGCCACCCTGGAAAGCTCTGCCGGCGCTGAGCTGAGCTTCATCCTGCCCAGAGAGA
GCACCCACAGATTCGAGGGCCTGTTCGCCAAGCTGGAAAAGAAACAGAAAGAGCTGG
GCATTGCCAGCTTCGGCGCCAGCATCACAACAATGGAAGAGGTGTTCCTGAGAGTGG
GCAAGCTGGTGGACAGCTCCATGGACATCCAGGCTATCCAGCTGCCCGCCCTGCAGT
ATCAGCACGAGAGAAGGGCTAGCGACTGGGCCGTGGACTCCAATCTGTGCGGCGCC
ATGGATCCCTCCGATGGAATCGGCGCCCTGATCGAAGAGGAACGGACCGCCGTGAA
GCTGAACACAGGACTGGCCCTGCACTGCCAGCAGTTCTGGGCCATGTTCCTGAAGAA
AGCCGCCTACAGCTGGCGCGAGTGGAAAATGGTGGCCGCACAGGTGCTGGTGCCCC
TGACCTGTGTGACACTGGCACTGCTGGCCATCAACTACAGCAGCGAGCTGTTCGACG
ACCCCATGCTGAGACTGACACTGGGCGAGTACGGCAGGACCGTGGTGCCTTTTTCTG
TGCCCGGCACCTCACAGCTGGGCCAGCAGCTGTCTGAACACCTGAAGGATGCCCTGC
AGGCCGAAGGCCAGGAACCCAGAGAAGTGCTGGGCGATCTGGAAGAGTTCCTGATCT
TCCGGGCCAGCGTGGAAGGCGGCGGATTCAACGAGAGATGCCTGGTGGCTGCCTCC
TTCCGGGATGTGGGCGAGAGAACAGTCGTGAACGCCCTGTTCAACAATCAGGCCTAC
CACAGCCCCGCCACCGCTCTGGCTGTGGTGGACAACCTGCTGTTTAAGCTGCTGTGT
GGCCCCCACGCCTCCATCGTGGTGTCCAATTTCCCCCAGCCCAGAAGCGCTCTGCAG
GCTGCCAAGGACCAGTTCAACGAGGGCCGGAAGGGCTTCGACATTGCTCTGAATCTG
CTGTTTGCCATGGCCTTTCTGGCCTCCACCTTCAGCATCCTGGCTGTGTCCGAGAGAG
```

-continued

LISTING OF SEQUENCES

CCGTGCAGGCCAAGCACGTGCAGTTTGTGTCTGGCGTGCACGTGGCCAGCTTTTGGC

TGTCTGCCCTGCTGTGGGACCTGATCAGCTTCCTGATCCCCAGCCTCCTGCTGCTGG

TGGTGTTCAAGGCCTTCGACGTGCGGGCCTTCACCAGGGATGGACACATGGCCGACA

CCTTGTTGTTGCTGCTGCTGTACGGCTGGGCCATCATCCCCCTGATGTACCTGATGAA

CTTCTTCTTCCTGGGCGCTGCCACCGCCTACACCAGACTGACCATCTTCAACATCCTG

AGCGGGATCGCCACCTTCCTGATGGTCACAATCATGCGGATCCCTGCCGTGAAACTG

GAAGAACTGAGCAAGACCCTGGACCATGTGTTTCTGGTGCTGCCCAACCACTGCCTG

GGCATGGCCGTGTCTAGCTTCTACGAGAACTACGAGACACGGCGGTACTGCACCTCC

AGCGAAGTGGCCGCCCACTACTGCAAGAAGTATAACATCCAGTATCAGGAAAACTTCT

ACGCTTGGAGCGCACCCGGCGTGGGCAGATTTGTGGCCTCTATGGCCGCCAGCGGC

TGCGCCTATCTGATCCTGCTGTTCCTGATCGAGACTAACCTGCTGCAGAGACTGAGAG

GCATCCTGTGCGCCCTGCGGCGGAGAAGAACACTGACCGAGCTGTACACCCGGATG

CCCGTGCTGCCTGAGGACCAGGATGTGGCCGACGAGCGGACAAGAATCCTGGCCCC

TAGCCCCGATAGCCTGCTGCACACCCCCCTGATCATCAAAGAACTGTCCAAGGTGTAC

GAGCAGCGGGTGCCACTGCTGGCTGTGGACAGACTGAGTCTGGCTGTGCAGAAAGG

CGAGTGCTTCGGACTGCTGGGCTTCAACGGCGCAGGCAAGACCACAACCTTCAAGAT

GCTGACAGGCGAGGAAAGCCTGACCTCCGGCGACGCCTTTGTGGGCGGACACAGGA

TCTCTTCCGATGTGGGCAAAGTGCGGCAGCGGATCGGCTACTGCCCTCAGTTCGACG

CCCTGCTGGATCACATGACCGGCAGGGAAATGCTCGTGATGTACGCCCGGCTGAGG

GGCATCCCCGAGAGACACATTGGCGCCTGCGTGGAAAACACCCTGCGGGGCCTGCT

GCTGGAACCCCACGCTAACAAACTCGTGCGGACCTACAGCGGCGGCAACAAGAGAAA

GCTGTCTACCGGCATTGCACTGATCGGCGAGCCAGCCGTGATCTTTCTGGATGAGCC

CAGCACAGGCATGGACCCCGTGGCTCGGAGACTGCTGTGGGATACAGTGGCCAGAG

CCAGAGAGTCCGGCAAGGCCATCATTATCACCAGCCACAGCATGGAAGAGTGCGAGG

CCCTGTGTACAAGACTGGCAATTATGGTGCAGGGACAGTTCAAGTGTCTGGGCAGCC

CTCAGCACCTGAAGTCCAAGTTCGGCTCCGGCTACAGCCTGCGGGCCAAGGTGCAGT

CTGAAGGGCAGCAGGAAGCCCTGGAAGAATTCAAAGCCTTCGTGGACCTGACCTTCC

CCGGCTCTGTGCTGGAAGATGAGCACCAGGGAATGGTGCACTACCATCTGCCTGGCA

GGGACCTGTCCTGGGCCAAAGTGTTTGGCATCCTGGAAAAGGCCAAAGAGAAGTACG

GCGTGGACGATTACAGCGTGTCCCAGATCAGCCTGGAACAGGTGTTCCTGTCCTTTG

CCCATCTGCAGCCCCCTACCGCCGAAGAGGGAAGAacgcgtacgcggccgctcgagcagaaactc atctcagaagaggatctggcagcaaatgatatcctggattacaaggatgacgacgataaggtttaagaattctgcagAAAAA

AAAAAAAAAAAAAAAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAAAAGC

19) SEQ ID NO: 19
Summary: Codon optimizad ABCA3 saquanca without any tags (-FLAG and Myc tags)
gggagacccaagctggctagcgtttaaacttaagcttggcaatccggtactgttggtaaagccaccatggccgtgctgagaca gctggctctgctgctgtggaagaactacaccctgcagaaacggaaggtgctcgtgaccgtgctggaactgttcctgcccctgct gttcagcggcatcctgatctggctgcggctgaagatccagagcgagaacgtgcccaacgccaccatctaccccggccagag catccaggaactgccccctgttcttcaccttcccccacccggcgatacctgggagctggcctatatccctagccacagcgacgc

-continued

| LISTING OF SEQUENCES |
| --- |

cgccaagaccgtgacagagacagtgcggagagccctcgtgatcaacatgagagtgcggggcttccccagcgagaaggact tcgaggactacatcagatacgacaactgcagcagcagcgtgctggccgccgtggtgtttgagcaccccttcaaccacagcaa agagcccctgcctctggccgtgaagtaccacctgagattcagctacacccggcggaactacatgtggacccagaccggctca ttcttcctgaaagagacagagggctggcacaccaccagcctgttccctctgttccccaaccctggccccagagagcctacatct cctgacggcggcgagcccggctatatcagagaaggattcctggccgtgcagcacgccgtggacagagccatcatggaatac cacgccgatgccgccacccggcagctgtttcagagactgaccgtgaccatcaagcggttcccttaccccccctttatcgccgac cctttcctggtggccatccagtaccagctgccactcctcctgctgctgagctttacctacaccgccctgacaatcgccagagccgt ggtgcaggaaaaagagcggcggctgaaagagtacatgcggatgatgggcctgtccagctggctgcattggagcgcctggttt ctgctgttcttcctgttcctgctgatcgccgccagcttcatgacactgctgttttgcgtgaaagtgaagcccaacgtggcagtgctga gccgcagcgatcctagcctggtgctggccttcctgctgtgcttcgccatcagcaccatcagcttcagctttatggtgtccaccttcttc agcaaggccaacatggccgctgccttcggcggcttcctgtacttctttacctatattccctacttcttcgtggcccctcggtacaact ggatgaccctgagccagaagctgtgcagctgcctgctgagcaacgtggccatggctatgggagcccagctgatcggcaagtt cgaggccaagggcatgggcatccagtggcgggatctgctgagccccgtgaacgtggacgacgacttctgcttcggccaggtg ctgggcatgctgctgctggactccgtgctgtatggcctcgtgacctggtatatggaagccgtgttccctggccagttcggcgtgcc ccagccctggtacttcttcatcatgcctagctattggtgcggcaagcccagggccgtggccggcaaagaggaagaggatagc gaccccgagaaggccctgcggaacgagtactttgaggccgagcccgaggatctggtggccggaatcaagatcaagcacct gagcaaggtgttccgcgtgggcaacaaggatagagccgctgtgcgggacctgaacctgaatctgtacgagggccagatcac cgtgctgctgggccataatggcgccggaaagaccaccaccctgagcatgctgaccggcctgtttcccccaacaagcggcag ggcctacatcagcggctacgagatcagccaggacatggtgcagatccggaagtccctgggcctgtgcccccagcacgacat cctgttcgacaacctgaccgtggccgagcacctgtacttttacgctcagctgaagggcctgagccggcagaaatgccccgagg aagtgaagcagatgctgcacatcatcggcctggaagataagtggaacagccggtcccggttcctgtccggcggaatgagaa gaaagctgagcatcggaatcgccctgattgccggcagcaaggtgctgatcctggacgagcctaccagcggcatggacgcca tctccagaagggccatctgggacctgctgcagcggcagaagtccgacagaaccatcgtgctgaccacccacttcatggacga ggccgacctgctgggcgaccggatcgctattatggccaagggggagctgcagtgctgcggcagcagcctgtttctgaagcag aaatacggcgctggctaccacatgaccctcgtgaaagagcctcactgcaaccccgaggacatctcccagctggtgcaccac cacgtgccaaatgccaccctggaaagctctgccggcgctgagctgagcttcatcctgcccagagagagcacccacagattcg agggcctgttcgccaagctggaaaagaaacagaaagagctgggcattgccagcttcggcgccagcatcacaacaatggaa gaggtgttcctgagagtgggcaagctggtggacagctccatggacatccaggctatccagctgcccgccctgcagtatcagca cgagagaagggctagcgactgggccgtggactccaatctgtgcggcgccatggatccctccgatggaatcggcgccctgatc gaagaggaacggaccgccgtgaagctgaacacaggactggccctgcactgccagcagttctgggccatgttcctgaagaaa gccgcctacagctggcgcgagtggaaaatggtggccgcacaggtgctggtgcccctgacctgtgtgacactggcactgctgg ccatcaactacagcagcgagctgttcgacgaccccatgctgagactgacactgggcgagtacggcaggaccgtggtgcctttt tctgtgcccggcacctcacagctgggccagcagctgtctgaacacctgaaggatgccctgcaggccgaaggccaggaaccc agagaagtgctgggcgatctggaagagttcctgatcttccgggccagcgtggaaggcggcggattcaacgagagatgcctgg tggctgcctccttccgggatgtgggcgagagaacagtcgtgaacgccctgttcaacaatcaggcctaccacagccccgccac cgctctggctgtggtggacaacctgctgtttaagctgctgtgtggcccccacgcctccatcgtggtgtccaatttcccccagccca gaagcgctctgcaggctgccaaggaccagttcaacgagggccggaagggattcgacattgctctgaatctgctgtttgccatgg cctttctggcctccaccttcagcatcctggctgtgtccgagagagccgtgcaggccaagcacgtgcagtttgtgtctggcgtgcac -continued

| LISTING OF SEQUENCES |
|---|
| **gtggccagcttttggctgtctgacctgctgtgggacctgatcagattactgatccccagcctcctgctgctggtggtgttcaaggcctt** |
| **cgacgtgcgggccttcaccagggatggacacatggccgacaccttgttgttgctgctgctgtacggctgggccatcatcccctg** |
| **atgtacctgatgaacttattattcctgggcgctgccaccgcctacaccagactgaccatcttcaacatcctgagcgggatcgcca** |
| **ccttcctgatggtcacaatcatgcggatccctgccgtgaaactggaagaactgagcaagaccctggaccatgtgtttctggtgct** |
| **gcccaaccactgcctgggcatggccgtgtctagcttctacgagaactacgagacacggcggtactgcacctccagcgaagtg** |
| **gccgcccactactgcaagaagtataacatccagtatcaggaaaacttctacgcttggagcgcacccggcgtgggcagatttgt** |
| **ggcctctatggccgccagcggctgcgcctatctgatcctgctgttactgatcgagactaacctgctgcagagactgagaggcatc** |
| **ctgtgcgccctgcggcggagaagaacactgaccgagctgtacacccggatgcccgtgctgcctgaggaccaggatgtggcc** |
| **gacgagcggacaagaatcctggcccctagccccgatagcctgctgcacacccccctgatcatcaaagaactgtccaaggtgt** |
| **acgagcagagggtgccactgctggctgtggacagactgagtctggctgtgcagaaaggcgagtgcttcggactgctgggcttc** |
| **aacggcgcaggcaagaccacaaccttcaagatgctgacaggcgaggaaagcctgacctccggcgacgcctttgtgggcgg** |
| **acacaggatctcttccgatgtgggcaaagtgcggcagcggatcggctactgccctcagttcgacgccctgctggatcacatga** |
| **ccggcagggaaatgctcgtgatgtacgcccggctgaggggcatccccgagagacacattggcgcctgcgtggaaaacacc** |
| **ctgcggggcctgctgctggaaccccacgctaacaaactcgtgcggacctacagcggcggcaacaagagaaagctgtctacc** |
| **ggcattgcactgatcggcgagccagccgtgatctttctggatgagcccagcacaggcatggaccccgtggctcggagactgct** |
| **gtgggatacagtggccagagccagagagtccggcaaggccatcattatcaccagccacagcatggaagagtgcgaggccc** |
| **tgtgtacaagactggcaattatggtgcagggacagttcaagtgtctgggcagccctcagcacctgaagtccaagttcggctccg** |
| **gctacagcctgcgggccaaggtgcagtctgaagggcagcaggaagccctggaagagttcaaagccttcgtggacctgacctt** |
| **ccccggctctgtgctggaagatgagcaccagggaatggtgcactaccatctgcctggcagggacctgtcctgggccaaagtgt** |
| **ttggcatcctggaaaaggccaaagagaagtacggcgtggacgattacagcgtgtcccagatcagcctggaacaggtgttcct** |
| **gtcctttgcccatctgcagcccccctaccgccgaagagggaaga** |

What is claimed is:

1. A composition comprising a modified polyribonucleotide, wherein the modified polyribonucleotide comprises an untranslated region derived from a cytochrome b-245 alpha polypeptide gene, wherein the untranslated region comprises (a) a 5' untranslated region comprising the nucleotide sequence SEQ ID NO: 14 or a sequence having 1 to 4 substitutions in comparison to SEQ ID NO: 14, and/or (b) a 3' untranslated region comprising the nucleotide sequence SEQ ID NO: 15 or a sequence having 1 to 7 substitutions in comparison to SEQ ID NO: 15, wherein upon translation the modified polyribonucleotide yields an ABCA3 protein, a functional fragment thereof, or a functional homolog thereof.

2. The composition of claim 1, wherein the modified polyribonucleotide includes a codon sequence that is optimized for translation within cells of a subject exposed to the modified polyribonucleotide.

3. The composition of claim 1, wherein the composition is formulated with cationic polymers and comprises a ratio of moles of amine groups of cationic polymers to moles of phosphate groups of the modified polyribonucleotide of about 8.

4. The composition of claim 1, wherein the modified polyribonucleotide comprises a combination of unmodified and modified nucleotides.

5. The composition of claim 1, wherein the modified polyribonucleotide further comprises a 3' or 5' noncoding region flanking the untranslated region derived from a cytochrome b-245 alpha polypeptide gene, wherein the noncoding region aids in enhanced expression of the ABCA3 protein, a functional fragment thereof, or a functional homolog thereof in cells.

6. The composition of claim 1, wherein the modified polyribonucleotide is formulated in a nanoparticle or nanocapsule, or
wherein the modified polyribonucleotide is formulated in a cationic lipid, cationic polymer, or nanoemulsion.

7. The composition of claim 1, wherein the modified polyribonucleotide comprises analogues of uridine or analogues of cytidine.

8. The composition of claim 7, wherein the modified polyribonucleotide comprises 5% to 50% analogues of uridine or 5% to 50% analogues of cytidine;
wherein the analogues of uridine are selected from the group consisting of pseudouridine, 2-thiouridine, 5-iodouridine, and 5-methyluridine;
wherein the analogues of cytidine are selected from the group consisting of 5-methylcytidine, 2'-amino-2'-deoxycytidine, 2'-fluoro-2'-deoxycytidine, and 5-iodocytidine; or
wherein the modified polyribonucleotide comprises (i) uridine and cytidine; and
(ii) analogues of the uridine and cytidine.

9. The composition of claim 1, wherein the modified polyribonucleotide comprises analogues of adenosine or analogues of guanosine.

10. The composition of claim 9, wherein the modified polyribonucleotide comprises (i) adenosine or guanosine; and (ii) analogues of the adenosine or guanosine.

11. The composition of claim 1, wherein the modified polyribonucleotide comprises less than 50% analogues of adenosine or guanosine.

12. The composition of claim 7, wherein the modified polyribonucleotide comprises 15% to 30% analogues of uridine or 15% to 30% analogues of cytidine.

13. The composition of claim 7, wherein the modified polyribonucleotide comprises 5-methylcytidine or pseudouridine.

14. The composition of claim 1, wherein the modified polyribonucleotide comprises the 5' untranslated region and the 3' untranslated region.

15. A method of treating a disease or condition associated with surfactant dysfunction comprising administering to a subject in need thereof a composition of claim 1.

16. A method of treating a disease or condition associated with an ABCA3 defect or malfunction of the eye comprising administering to a subject in need thereof a composition of claim 1.

* * * * *